US007129037B2

(12) United States Patent
Albert et al.

(10) Patent No.: US 7,129,037 B2
(45) Date of Patent: Oct. 31, 2006

(54) METHODS FOR USE OF APOPTOTIC CELLS TO DELIVER ANTIGEN TO DENDRITIC CELLS FOR INDUCTION OR TOLERIZATION OF T CELLS

(75) Inventors: Matthew L. Albert, Paris (FR); Nina Bhardwaj, West Orange, NJ (US); Ralph M. Steinman, Westport, CT (US); Kayo Inaba, Kyoto (JP); Robert Darnell, Pelham, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 10/014,877

(22) Filed: Dec. 11, 2001

(65) Prior Publication Data

US 2002/0146396 A1 Oct. 10, 2002

Related U.S. Application Data

(63) Continuation of application No. 09/251,896, filed on Feb. 19, 1999, now Pat. No. 6,602,709.

(60) Provisional application No. 60/101,749, filed on Sep. 24, 1998, provisional application No. 60/077,095, filed on Mar. 6, 1998, provisional application No. 60/075,356, filed on Feb. 20, 1998.

(51) Int. Cl.
*C12Q 1/00* (2006.01)
*G01N 33/53* (2006.01)
*C12N 5/08* (2006.01)
*C12N 5/00* (2006.01)

(52) U.S. Cl. .................. 435/4; 435/7.24; 435/372; 435/373

(58) Field of Classification Search ............... 435/372, 435/4, 372.1–373, 7.24
See application file for complete search history.

(56) References Cited

U.S. PATENT DOCUMENTS

| 4,861,589 A | 8/1989 | Ju |
| 5,643,599 A | 7/1997 | Lee et al. |

FOREIGN PATENT DOCUMENTS

| EP | 546 787 A2 | 6/1993 |
| EP | 563 485 A1 | 10/1993 |
| WO | 91/13632 | 9/1991 |
| WO | 93/20185 | 10/1993 |
| WO | 94/02156 | 2/1994 |
| WO | WO 9402156 A1 * | 2/1994 |
| WO | 95/15340 | 6/1995 |
| WO | 95/28479 | 10/1995 |
| WO | 95/34638 | 12/1995 |
| WO | 97/29182 | 8/1997 |
| WO | 99/58645 | 11/1999 |

OTHER PUBLICATIONS

Abbas, et al., "Uptake & Processing of Extracellular Protein Antigens by Antigen-Presenting Cells," W.B. Saunders Co. 1991 AT 124-126.
Abbas, et al., "Antigen Presentation and T Cell Antigen Recognition", *Cellular and Molecular Immunology*, W.B. Saunders Co. Philadelphia AT 123, 1991.
Aichele, et al., "Antiviral Cytotoxic T Cell Response Induced by In Vivo Priming with a Free Synthetic Peptide," *J. Exp. Med*, 171:1815-1820, May 1990.
Albert et al., "Resurrecting the Dead: DCS Cross-Present Antigen Derived From Apoptotic Cells on MHC 1", *Immunologist*, vol. 6, No. 5, pp. 194-198, 1998.
Albert et al., "Dendritic Cells Acquire Antigen From Apoptotic Cells and Induce Class I-Restricted CTLS," *Nature*, vol. 392, pp. 86-89, Mar. 1998.
Albert, et al., "Immature Dendritic Cells Phogocytose Apoptotic Cells Via $\alpha_v\beta_5$ and CD36, and Cross-Present Antigens to Cytotoxic T Lymphocytes," *Journal. Exp. Med.*, 188, 1359-1368, Oct. 5, 1998.
Albert, et al., "Tumor-Specific Killer Cells in Paraneoplastic Cerebellar Degeneration," *Nature Medicine*, vol. 4, No. 11, pp. 1321-1324, Nov. 1998.
Amigorena, S., "Anti-Tumor Immunotherapy Using Dendritic-Cell-Derived Exosomes," *Res Immunol.*, 149, 661-662, 1998.
Anderson, et al., "Bovine PAS-6/7 Binds $\alpha_v\beta_5$ Integrin and Anionic Phospholipids Through Two Domains," *Biochemistry*, 36:5441-5446, 1997.
Arnold, et al., "Cross-Priming of Minor Histocompatibility Antigen-Specific Cytotoxic T Cells Upon Immunization with the Heat Shock Protein GP [96]," *J. Exp. Med.*, 182, 885-889, Sep. 1995.
Arregaard, et al., "Characterization of Glycoprotein PAS-6/7 From Membranes of Bovine Milk Fat Globules," *Eur. J.BioChem*, 240:628-636, 1996.
Auchincloss, et al., "Antigen Processing and Presentation in Transplantation," *Curr. Opin. Imumunol.*, 8, 681-687, Oct. 1996.

(Continued)

*Primary Examiner*—Gary B. Nickol
(74) *Attorney, Agent, or Firm*—Klauber & Jackson

(57) ABSTRACT

This invention relates to methods and compositions useful for delivering antigens to dendritic cells which are then useful for inducing antigen-specific cytotoxic T lymphocytes and T helper cells. This invention also provides assays for evaluating the activity of cytotoxic T lymphocytes. According to the invention, antigens are targeted to dendritic cells by apoptotic cells which may also be modified to express non-native antigens for presentation to the dendritic cells. The dendritic cells which are primed by the apoptotic cells are capable of processing and presenting the processed antigen and inducing cytotoxic T lymphocyte activity or may also be used in vaccine therapies.

6 Claims, 41 Drawing Sheets

OTHER PUBLICATIONS

Badley, A.D., "Macrophase-Dependent Apoptosis of CD4 + T Lymphocytes from HIV-Infected Individuals is Mediated by FASL and Tumor Necrosis Factor," *J. Exp. Med.*, 185, 55-64, Jan. 1997.

Bakker, et al., "Generation of Antimelanoma Cytotoxic T Lymphocytes From Healthy Donors After Presentation of Melanoma-Associated Antigen-Derived Eptiopes by Dendritic Cells *In Vitro*," *Cancer Research*, vol. 55, pp. 5330-5334, Nov. 15, 1995.

Banchereau, et al., "Dendritic Cells and the Control of Immunity", *Nature*, 392, 245-252, Mar. 1998.

Bellone, et al., "Processing of Engulfed Apoptotic Bodies Yields T Cell Epitopes," *The Journal of Immunology*, 159, pp. 5391-5399.

Bender, et al., "The Distinctive Features of Influenza Virus Infection of Dendritric Cells," *Immunobiology*, 198, 552-567, 1997/98.

Bender, et al., "Improved Methods for the Generation of Dendritic Cells From Nonproliferating Progenitors in Human Blood," *J. Immunol Methods.*, vol. 196, pp. 121-135, 1996.

Bender, et al., "Inactivated Influenza Virus, When Presented on Dendritic Cells, Elicit Human CD8+ Cytolytic T Cell Responses," *J. Exp. Med.*, vol. 182, pp. 1663-1671, Dec. 1995.

Bender, et al., "Effect of Granulocyte/Macrophage Colony-Stimulating Factor on Human Monocytes Infected with Influenza a Virus," *J. Immunol.*, 151, 5416-5424, Nov. 15, 1993.

Bennett, et al. Induction of a CD8+ Cytotoxic T Lymphocyte Response by Cross-Priming Requires Cognate CD4+ T Cell Help, *J. Exp. Med.*, 186, 65-70, Jul. 7, 1997.

Bennet, et al., "Help for Cytotoxic-T-Cell Responses is Mediated by CD40 Signalling," *Nature*, 393, 478-480, Jun. 4, 1998.

Benichou, et al., "Donor Major Histocompatibility Complex (MHC) Peptides are Presented by Recipient MHC Molecules During Graft Rejection," *J. Exp. Med.*, 175, 305-308, Jan. 1992.

Bevan, M.J., "Cross-Priming for a Secondary Cytotoxic Response to Minor H Antigens with H-2 Congenic Cells Which do not Cross-React in the Cytotoxic Assay," *J. Exp. Med.*, 143, 1283-1288, 1976.

Bevan, M.J., "Priming for a Cytotoxic Response to Minor Histocompatibility Antigens: Antigen Specificity and Failure to Demonstrate a Carrier Effect," *Journal of Immunology*, 118, 1370-1374, Apr. 1977.

Bhardwaj, et al., "Influenza Virus-Infected Dendritic Cells Stimulate Strong Proliferative and Cytolytic Responses from Human CD8+ T Cells," *J. Clin. Invest.* vol. 94, pp. 797-807, Aug. 1994.

Bhardwaj, et al., "Il-12 in Conjunction with Dendritic Cells Enhances Anti-Viral, CD8+ CTL Responses In Vitro," *J. Clin Invest.*, vol. 98, No. 3, pp. 715-722, Aug. 1996.

Bhardwaj, "Interactions of Viruses with Dendritic Cells: a Double-Edged Sword," *J. Exp. Med.*, vol. 186, No. 6, pp. 795-799, Sep. 15, 1997.

Bhardwaj, et al., "Dendritic Cells are Potent Antigen-Presenting Cells FO Microbial Superantigens," *J. Exp. Med.*, 175, 267-273, Jan. 1992.

Blystone, et al., "Integrin Alpha V Beta 3 Differentially Regulates Adhesive and Phagocytic Functions of the Fibronectin Receptor Alpha 5 Beta 1," *Journal of Cell Biology*, 127, 1129-1137, Nov. 1994.

Boog, et al., "Abolition of Specific Immune Response Defect by Immunization with Dendritic Cells," *Nature*, vol. 318, pp. 59-62, Nov. 7, 1985.

Boon, et al., "Tumor Antigens Recognized by T Lymphocytes," *Annual Review of Immunology*, vol. 12, pp. 337-365, 1994.

Boon, et al., "Tumor Antigens Recognized by Cytolytic T Lymphocytes: Present Perspectives for Specific Immunotherapy," *Int.J. Cancer*, vol. 54, pp. 177-180, 1993.

Britz, et al., "Specialized Antigen-Presenting Cells, Splenic Dendritic Cells and Peritoneal-Exudate Cells Induced by Mycobacteria Activate Effector T Cells that are Resistant to Suppression," *J. Exp. Med.*, vol. 155, pp. 1344-1356, May, 1982.

Bujdoso, et al., "Characterization of Sheep Afferent Lymph Dendritic Cells and Their Role in Antigen Carriage," *J. Exp. Med.*, vol. 170, pp. 1285-1302, Oct., 1989.

Carbone, et al., "Induction of Cytotoxic T Lymphocytes by Primary In Vitro Stimulation with Peptides," *J. Exp. Med.*, 167, 1767-1779, Jun. 1988.

Carmichael, et al., "Quantitative Analysis of the Human Immunodeficiency Virus Type 1 (HIV-1)-Specific Cytotoxic T Lymphocyte (CTL) Response at Different Stages of HIV-1 Infection: Diferential CTL Responses to HIV-1 and Epstein-Barr Virus in Late Disease," , *J. Exp. Med*, 177: 249-256, Feb. 1993.

Caux, et al., "Human Dendritic Langerhans Cells Generated In Vitro from CD34+ Progenitors can Prime Naive CD4+ T Cells and Process Soluble Antigen," *J. Immunology*, vol. 155, pp. 5427-5435, 1995.

Caux, et al., "CD34+ Hematopoietic Progenitors from Human Cord Blood Differentiate Along Two Independent Dendritic Cell Pathways in Response to GM-CSF+ TNFα," *J. Exp. Med.* vol. 184, pp. 695-706, Aug., 1996.

Caux, et al., "GM-CSF and TNF-α Cooperate in the Generation of Dendritic Langerhans Cells,"*Nature*, vol. 360, pp. 258-261, Nov. 19, 1992.

Caux, C., et al., "Activation of Human Dendritic Cells Through CD40 Cross-Linking," *J. Exp. Med.*, 180, 1263-1272, Oct. 1994.

Cella M, et al., "Ligation of CD40 on Dendritic Cells Triggers Production of High Levels of Interleukin-12 and Enhances T Cell Stimulatory Capacity: T-T Help Via APC Activation," *J Exp Med.*, 184:747-752, Aug. 1996.

Cella, M. et al., "Inflammatory Stimuli Induce Accumulation of MHC Class II Complexes on Dendritic Cells," *Nature*, 388, 782-787, Aug. 1997.

Cella, et al., "Origin, Maturation and Antigen Presenting Function of Dendritic Cells," *Curr. Opin. Immunol*, 9, 10-16, 1997.

Chicz, R. M., et al., "Predominant Naturally Processed Peptides Bound to HLA-DR1 are Derived from MHC-Related Molecules and are Heterogeneous in Size," *Nature*, 358, 764-768, Aug. 27, 1992.

Cohen, et al., "Murine Epidermal Langerhans Cells and Splenic Dendritic Cells Present Tumor-Associated Antigens to Primed T Cells," *Eur. J. Immunol.*, vol. 24, pp. 315-319, 1994.

Cohen, "Caspases:The Executioners of Apoptosis," *Biochem, J.*, 326, pp. 1-16, 1997.

Cohen, J.J., "Apoptosis," *Immunol. Today*, 14, 126-130, 1993.

Crowley, et al., "Dendritic Cells are the Principal Cells in Mouse Spleen Bearing Immunogenic Fragments of Foreign Proteins," *J. Exp. Med.*, vol. 172, No. 1, 99. 383-386, Jul. 1990.

De Bruijn, et al., "Mechanisms of Induction of Primary Virus-Specific Cytotoxic T Lymphocyte Responses," *Eur. J. Immunol.*, vol. 22, pp. 3013-3020, 1992.

Depanfilis, G., et al., "The S-100β Protein Presumably Represents a New Marker for the T Suppressor Cells," *Journal of Investigative Dermatology*, 87, 1986.

Depanfilis, G., et al, "An in Situ Immunogold Method Applied to the Identification of Plasma Membrane-Associated Antigens of Skin-Infiltrating Cells," *Journal of Investigative Dermatology*, 510-514, 1986.

De Saint-Vis, et al., A Novel Lysosome-Associated Membrane Glycoprotein, DC-Lamp, Induced Upondcmaturation, Is Transiently Expressed in MHC Class II Compartment, *Immunity.*, 9,325-336, Sep. 1998.

De Smedt T, et al., "Regulation of Dendritic Cell Numbers and Maturation by Lipopolysaccharide In Vivo," *J Exp Med.*, 184:1413-1424, Oct. 1996.

De Tongi, et al., "Abnormal Development of Peripheral Lymphoid Organs in Mice Deficient in Lymphotoxin," *Science*, 264, 703-706, Apr. 29, 1994.

Devitt, et al., "Human CD14 Mediates Recognition and Phagocytosis of Apoptopic Cells," *Nature*, 392, 505-509, Apr. 2, 1998.

Diaz-Gonzelez, F., et al., "Trans-Dominant Inhibition of Integrin Function," *Molecular Biology of the Cell*, 7, 1939-1951, Dec. 1996.

Dranoff, et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity," *Prac. Natl. Acad. Sci.. USA*, vol. 90, No. 8, pp. 3539-3543, Apr. 1993.

Disis, et al., "In Vitro Generation of Human Cytolytic T-Cells Specific for Peptides Derived from the Her-2/NEU Protooncogene Protein", *Cancer Research*, vol. 54, Feb. 15, 1994, pp. 1071-1076.

Dranoff, et al., "Vaccination with Irradiated Tumorcells Engineered to Secrete Murine Granulocyte-Macrophage Colony-Stimulating Factor Stimulates Potent, Specific, and Long-Lasting Anti-Tumor Immunity", *Prac. Natl. Acad. Sci.. USA*, vol. 90, No. 8, Apr. 1993, pp. 3539-3543.

Duvall, E,M, et al., "Death and the Cell," *Immunol. Today*, 7, 115-119, 1986.

Fadok, V.A., et al., "Different Populations of Macrophages use Either the Vitronectin Receptor or the Phosphatidylserine Receptor to Recognize and Remove Apoptotic Cells," *J. Immunol.*, 149, 4029-4035, Dec. 15, 1992.

Fadok, V.A., et al., "Macrophages that have Ingested Apoptotic Cells In Vitro Inhibit Proinflammatory Cytokine Production Through Autocrine/Paracrine Mechanisms Involving TGF-β, PGE2, and PAF," *J. Clin. Invest.*, 101, 890-898, Feb. 1998.

Fangmann, J., et al., "Rejection of Skin Allografts by Indirect Allorecognition of Donor Class I Major Histocompatibility Complex Peptides," *J. Exp. Med.*, 175, 1521-1529, Jun. 1992.

Faustman, et al., "Prevention of Rejection of Murine Islet Allografts by Pretreatment with Anti-Dendritic Cell Antibody," *Proc. Natl. Acad. Sci. USA*, vol. 81, pp. 3864-3868, Jun. 1984.

Fenteany, G., et al., "Inhibition of Proteasome Activities and Subunit-Specific Amino-Terminal Threonine Modification by Lactacystin," *Science*, 268, 726-731, May 5, 1995.

FESQ, H., et al., "Programmed Cell Death (Apoptosis) in Human Monocytes Infected by Influenza Virus," *Immunobiol.*, 190, 175-182, 1994.

Finnemann, S.C., et al., "Phagocytosis of Rod Outer Segments by Retinal Pigment Epithelial Cells Requires Alpha (V) Beta5 Intergrin for Binding but not for Internalization," *PNAS*, 94, 12932-12937, Nov. 1997.

Fisher, et al., "Neoplastic Cells Obtained from Hodgkin's Disease Function as Accessory Cells for Mitogen-Induced Human T Cell Proliferative Responses," *J. Immunol.*, vol. 132, No. 5, pp. 2672-2677, May, 1984.

Flamand, et al., "Murine Dendritic Cells Pulsed In Vitro with Tumor Antigen Induce Tumor Resistance In Vivo," *Eur. J. Immunol.*, vol. 24, pp. 605-610, 1994.

Flamand, et al., "Vaccination with Tumor Antigen-Pulsed Dendritic Cells Induces In Vivo Resistance to a B Cell Lymphoma," *Adv. Exp. Med. Biol.*, vol. 329, pp. 611-615, 1993.

Fossum, et al., "The Roles of the Interdigitating Cells and Natural Killer Cells in the Rapid Rejection of Allogeneic Lymphocytes," *Eur. J. Immunol.*, 16, 440-450, 1986.

Forster, I., et al., "Peripheral Tolerance of CD4 T Cells Following Local Activation in Adolescent Mice," *Eur. J. Immunol.*, 26, 3194-3202, 1996.

Friedlander, M., et al., "Definition of Two Angiogenic Pathways by Distinct $\alpha_v$ Integrins," *Science*, 270, 1500-1502, Dec. 1, 1995.

Gao, X., et al., "Priming of Influenza Virus-Specific Cytotoxic T Lymphocytes Vivo by Short Synthetic Peptides," *J. Immunol.*, 147:3268-3273, Nov. 15, 1991.

Gao, Y., et al., "Antiinflammatory Effects of CD95 Ligand (FASL)-Induced Apoptosis," *J. Exp. Med.*, 188, 887-896, Sep. 7, 1998.

Godman, G.C.,et al., "Action of Cytochalasin D on Cells of Established Lines. Zeiosis and Movements at the Cell Surface," *J Cell Biology*, 64, 644-667, 1975.

Gotch, F., et al., "Cytotoxic T Lymphocytes Recognize a Fragment of Influenza Virus Matrix Protein in Association with HLA-A2," *Nature*, 326, 881-882, Apr. 30, 1987.

Heath, W.R., et al., "Cross-Tolerance: a Pathway for Inducing Tolerance to Pheripheral Tissue Antigens," *J. Exp. Med.*, 187, 1549-1553, May 18, 1998.

Heemels, M., et al., "Generation, Translocation, and Presentation of MHC Class I-Restricted Peptides," *H. Annual Review of Biochemistry*, 64, 463-491, 1995.

Hess, K.L., et al., "A Novel Flow Cytometric Method for Quantifying Phagocytosis of Apoptotic Cells," *Cytometry*, 27, 145-152, 1997.

Hill, A.V.S., et al., "Molecular Analysis of the Association of HLA-B53 and Resistance to Severe Malaria," *Nature* 360:434-439, Dec. 3, 1992.

Hirst, G.K., "The Quantitative Determination of Influenza Virus and Antibodies by Means of Red Cell Agglutination," *J. Exp. Med.*, 75, 49-64, 1942.

Hofman, P., et al., "Susceptibility of Mononuclear Phagocytes to Influenza a Virus Infection and Possible Role in the Antiviral Response," *J. Leuk. Biol.*, 61, 408-414, Apr. 1997.

Hosaka, et al., "Entry of Heat-Inactivated Influenza Virus and Induction of Target Susceptibility of Cytotoxic T Cell-Mediated Lysis," *Virus Res.*, Suppl. 1, p. 56, 1985.

Hsu, et al., "Vaccination of Patients with B-Celllymphoma Using Autologous Antigen-Pulsed Dendritic Cells," *Nature Medicine*, vol. 2, No. 1, pp. 52-58, Jan. 1996.

Huang, et al., "Role of Bone Marrow-Derived Cells in Presenting MHC Class I-Restricted Tumor Antigens," *Science*, 264, 961-965, May 13, 1994.

Hughes, et al., "Integrin Affinity Modulation," *Trends Cell Biol.*, 8:359-364, Sep. 1998.

Hunt, D.F., et al., "Peptides Presented to the Immune System by the Murine Class II Major Histocompatibility Complex Molecule 1-$A^d$, " *Science*, 256, 1817-1820, Jun. 26, 1992.

Ignatowicz, L., et al., "The Repertoire of T Cells Shaped by a Single MHC/Peptide Ligand," *Cell*, 84, 521-529, Feb. 23, 1996.

Inaba, K., et al., "Efficient Presentation of Phagocytosed Cellular Fragments on the Major Histocompatibility Complex Class II Products of Dendritic Cells," *J. Exp. Med.*, vol. 188, No. 11, pp. 2163-2173, Dec. 7, 1998.

Inaba, K., et al., "The Tissue Distribution of the B7-2 Costimultor in Mice: Abundant Expression on Dendritic Cells in Situ and During Maturation In Vitro," *J. Exp. Med.*, 180, 1849-1860, Nov. 1994.

Inaba, K., et al., "High Levels of a Major Histocompatibility Complex II-Self Peptide Complex on Dendritic Cells from the T Cell Areas of Lymph Nodes," *Journal of Experimental Medicine*, vol. 186, No. 5, pp. 665-672, Aug. 29, 1997.

Inaba, K., et al., "Dendritic Cell Progenitors Phagocytose Particulates, Including Bacillus Calmette-Guerin Organisms, and Sensitize Mice to Mycobacterial Antigens In Vivo, " *J. Exp. Med.*, 178, 479-488, Aug. 1993.

Inaba, K., et al., "Dendritic Cells as Antigen Presenting Cells In Vivo," *Intern. Rev. Immunol.*, , 6, 197-206, 1990.

Inaba, et al., "Dendritic Cells Pulsed with Protein Antigens In Vitro can Prime Antigen-Specific, MHC-Restricted T Cells in Situ," *J. Exp. Med.*, vol. 172, pp. 631-640, Aug. 1990.

Inaba, et al., "Dendritic Cells are Critical Accessory Cells for Thymus-Dependent Antibody Responses in Mouse and in Man," *Proc. Natl Acad. Sci. USA*, 80:6041-6045, 1983.

Inaba, et al., "Protein Specific Helper T-Lymphocyte Formation Initiated by Dendritic Cells," *Science*, vol. 229, No. 4713, pp. 475-479, Aug. 2, 1985.

Inaba, et al., "Clustering of Dendritic Cells, Helper T Lymphocytes, and Histocompatible B Cells During Primary Antibody Responses In Vitro," *J. Exp. Med.*, vol. 160, No. 3, pp. 858-876, Sep. 1984.

Inaba, et al., "Generation of Large Numbers of Dendritic Cells from Mouse Bone Marrow Cultures Supplemented with Granulocyte/Macrophage Colony-Stimulating Factor," *J. Exp. Med.*, vol. 176, No. 6, pp. 1693-1702, Dec., 1992.

Janeway et al., *Immunobiology*, Garland Publishing Inc., Third Edition, pp. 7:10-7:14, 1997.

Johnson, R.P., et al., "Identification of Overlapping HLA Class I-Restricted Cytotoxic T Cell Epitopes in a Conserved Region of the Human Immunodeficiency Virus Type 1 Envelope Glycoprotein: Definition of Minimum Epitopes and Analysis of the Effects of Sequence Variation," *J. Exp. Med*, 175:961-971, Apr. 1992.

Jondal, et al., "MHC Class-I Restricted CTL Responses to Exogenous Antigens," *Immunity*, 5:295-302, Oct. 1996.

Khanna, R., et al., "Hierarchy of Epstein-Barr Virus-Specific Cytotoxic T-Cell Responses in Individuals Carrying Different Subtypes of an HLA Allele: Implications for Epitope-Based Antiviral Vaccines," *J. Virol*, 71(10):7429-7435, Oct. 1997.

Kovacsovics-Bankowski, et al., "A Phagosome-to-Cytosol Pathway for Exogenous Antigens Presented on MHC Class I Molecules," *Science*, 267, 243-246, Jan. 13, 1995.

Kurts, et al., "Constitutive Class I-Restricted Exogenous Presentation of Self Antigens In Vivo," *J. Exp. Med.*, 184, 923-930, Sep. 1996.

Kurts, C., et al., "Class I-Restricted Cross-Presentation of Exogenous Self Antigens Leads to Deletion of Autoreactive CD8+ T Cells," *J. Exp. Med.*, 186, 239-245, Jul. 21, 1997.

Kurts, C., et al., "The Peripheral Deletion of Autoreactive CD8+ T Cells Induced by Cross-Presentation of Self-Antigens Involves Signaling Through CD95 (FAS, APO-1)," *J. Exp. Med.*, 188, 415-420, Jul. 20, 1998.

Kuzu, H., et al., "In Vivo Priming Effect During Various Stages of Ontogeny of an Influenza a Virus Nucleoprotein Peptide," *Eur. J. Immunol.*, 23:1397-1400, 1993.

Larhammar, D., et al., "Alpha Chain of HLA-DR Transplantation Antigens is a Member of the Same Protein Superfamily as the Immunoglobulins," *Cell*, 30, 153-161, Aug. 1982.

Larooca, D., et al., "A $M_r$ 46,000 Human Milk Fat Globule Protein that is Highly Expressed in Human Breast Tumors Contains Factor VIII-Like Domains," *Cancer. Res*, 51, 4994-4998, Sep. 15, 1991.

Li, et al., "Priming with Recombinant Influenza Virus Followed by Administration of Recombinant Vaccinia Virus Induces CD8+ T-Cell-Mediated Protective Immunity Against Malaria," *Proc. Natl Acad. Sci. USA*, vol. 90, pp. 5214-5218, Jun. 1993.

Liu, Z., et al., "Indirect Recognition of Donor HLA-DR Peptides in Organ Allograft Rejection," *J. Clin. Invest.*, 98, 1150-1157, Sep. 1996.

Liu, Z., et al., "T Cell Recognition of Self-Human Histocompatibility Leukocyte Antigens (HLA)-DR Peptides in Context of Syngeneic HLA-DR Molecules," *J. Exp. Med.*, 175, 1663-1668, Jun. 1992.

Macatonia, et al., "Primary Stimulation by Dendritic Cells Induces Antiviral Proliferative and Cytotoxic T Cell Responses In Vitro," *Journal of Experimental Medicine*, vol. 169, pp. 1255-1264, Apr. 1989.

Macatonia, et al., "Localization of Antigen on Lymph Node Dendritic Cells After Exposure to the Contact Sensitizer Fluorescein Isothiocyanate," *J. Exp. Med.*, vol. 166, p. 1654-1667, Dec. 1987.

Macpherson, et al., "Endotoxin-Mediated Dendritic Cell Release from the Intestine: Characterization of Released Dendritic Cells and TNF Dependence," *J. Immunol.* vol. 154, 1317-1322, Feb. 1995.

Mather, I.H., et al., "Membranes of Mammary Gland. Loosely Associated Proteins and Compositional Heterogeneity of Bovine Milk Fat Globule Membrane," *J. Diary Sci.*, 60:394-402, Mar. 1977.

Matzinger, P., et al., "Does T-Cell Tolerance Require a Dedicated Antigen-Presenting Cell?," *Nature*, 338, 74-76, Mar. 2, 1989.

McClean, et al., "CDNA Sequence of the Human Integrin $\beta_5$ Subunit," *Journal of Biological Chemistry*, 265, 17126-17131, 1990.

McMichael, A.J., et al., "Influenza Virus-Specific Cytotoxic T Cells in Man; Induction and Properties of the Cytotoxic Cell," *Eur. J. Immunol.*, 8:705-711, 1978.

Miller, "The Role of the Caspase Family of Cysteine Proteases in Apoptosis," *Sem. Immunol*, 5:35-49, 1997.

Moore, M.W., et al., "Introduction of Soluble Protein into the Class I Pathway of Antigen Processing and Presentation," *Cell*, 54:777-785, Sep. 9, 1988.

Moses, R.D., et al., "Xenogenic Proliferation and Lymphokine Production are Dependent on CD4+ Helper T Cells and Self Antigen-Presenting Cells in the Mouse," *J. Exp. Med.*, 172, 567-575, Aug. 1990.

Mukherji, et al., "Induction of Antigen-Specific Cytolytic T Cells in Situ in Human Melanoma by Immunization with Synthetic Peptide-Pulsed Autologous Antigen Presenting Cells," *Proc. Natl Acad. Sci., USA*, vol. 92, pp. 8078-8082, Aug. 1995.

Nair, et al., "Induction of Primary, Antiviral; Cytotoxic and Proliferative Responses with Antigens Administered Via Dendritic Cells," *Virol*, 67:4062-4069, Jul. 1993.

Nair, et la., "Soluble Proteins Delivered to Dendritic Cells Via PH-Sensitive Liposomes Induce Primary Cytotoxic T Lymphocyte Responses In Vitro," *J. Exp. Med.*, 175:609-612, Feb. 1992.

Nonacs, et al., "Mechanisms of Mouse Spleen Dendritic Cell Function in the Generation of Influenza-Specific, Cytolytic T Lymphocytes," *J. Exp. Med.*, vol. 176, pp. 519-529, Aug. 1992.

Norbury, C.C., et al., "Constitutive Macropinocytosis Allows Tap-Dependent Major Histocompatibility Complex Class I Presentation of Exogenous Soluble Antigen by Bone Marrow-Derived Dendritic Cells," *Eur. J. Immunol.*, 27, 280-288, 1997.

Nussenzweig, M.C., et al., "Studies of the Cell Surface of Mouse Dendritic Cells and Other Leukocytes," *J. Exp. Med.*, 154, pp. 168-187, Jul. 1981.

O'Doherty, et al., "Human Blood Contains Two Subsets of Dendritic Cells, One Immunologically Mature and the Other Immature," *Immunology*, vol. 82, pp. 487-493, 1994.

Osband, et al., "Problems in the Investigational Study and Clinical Use of Cancer Immunotherapy," *Immunology Today*, vol. 11. No. 6, pp. 103-105, 1990.

Paglia, P., et al., "Murine Dendritic Cells Loaded In Vitro with Soluble Protein Prime Cytotoxic T Lymphocytes Against Tumor Antigen In Vitro," *J. Exp. Med.*, 183, 317-322, Jan. 1996.

Paglia, et al., "Immortalized Dendritic Cell Line Fully Competent in Antigen Presentation Initiates Primary T Cell Responses In Vivo," *J. Exp. Med.*, vol. 178, pp. 1893-1901, Dec., 1993.

Patton, S., et al., "The Milk Fat Globule Membrane," *Biochim Biophys Acta*, 415:273-309, 1975.

Peace, et al., "Lysis of RAS Oncogene-Transformed Cells by Specific Cytotoxic T Lymphocytes Elicited by Primary In Vitro Immunization with Mutated RAS Peptide," *J. Exp. Med.*, vol. 179, pp. 473-479, Feb., 1994.

Peterson, J.A., et al., "Glycoproteins of the Human Milk Fat Globule in the Protection of the Breast-Fed Infant Against Infections," *Biol. Neonate*, 74:143-162, 1998.

Pettengell, et al., "Peripheral Blood Progenitor Cell Transportation in Lymphoma and Leukemia Using a Single Apheresis," *Blood*, vol. 82, No. 12, pp. 3770-3777, Dec. 15, 1993.

Pierre, P., et al., "Developmental Regulation of MHC Class II Transport in Mouse Dendritic Cells," *Nature*, 388, 787-792, Aug. 21, 1997.

Pfeifer, J.D., et al., "Phagocytic Processing of Bacterial Antigens for Class I MHC Presentation to T Cells," *Nature*, 361, 359-362, Jan. 1993.

Platt, N., et al., "Recognizing Death: the Phagocytosis of Apoptotic Cells," *Trends Cell Biol.*, 8, 365-372, Sep. 1998.

Pope, M., et al, "Low Levels of HIV-1 Infection in Cut Aneous Dendritic Cells Promote Extensive Viral Replication Upon Binding to Memory CD4+ T Cells," *J. Exp. Med.*, 182, 2045-2056, Dec. 1995.

Porgador, A. and Gilboa, E., "Bone Marrow-Generated Dendritic Cells Pulsed with a Class I-Restricted Peptide are Potent Inducers of Cytotoxic T Lymphocytes," *J. Exp. Med.*, 182, 255-260, Jul. 1995.

Raposo, et al., "B Lymphocytes Secrete Antigen-Presenting Vesicles," *J. Exp. Med.*, 183: 1161-1172, Mar. 1996.

Reis E Sousa, C., et al., "Phagocytosis of Antigens by Langerhans Cells In Vitro," *J. Exp. Med.*, 178, 509-519, Aug. 1993.

Reis E Sousa, C., et al., "Major Histocompatibility Complex Class I Presentation of Peptides Derived from Soluble Exogenous Antigen by a Subset of Cells Engaged in Phagocytosis," *J. Exp. Med.*, 182, 841-851, Sep. 1995.

Ren, Y., et al., "CD36 Gene Transfer Confers Capacity for Phagocytosis of Cells Undergoing Apoptosis," *J. Exp. Med.*, 181, 1857 (ABSTRACT), May 1995.

Rescigno, M., et al., Bacteria-Induced Neo-Biosynthesis, Stabilization, and Surface Expression of Functional Class I Molecules in Mouse Dendritic Cells, *PNAS* 95, 5229-5234, Apr. 1998.

Riddell, et al., "Restoration of Viral Immunity of Immunodeficient Humans by the Adoptive Transfer of T Cell Clones," *Science*, vol. 257, pp. 238-241, Jul. 10, 1992.

Ridge, J.P., et al., "A Conditioned Dendritic Cell can be a Temporal Bridge Between a CD4+ T-Helper and a T-Killer Cell," *Nature*, 393, 474-478, Jun. 1998.

Rieser, C., et al., "Prostaglandin E2 and Tumor Necrosis Factor α Cooperate to Activate Human Dendritic Cells: Synergistic Activation of Interleukin 12 Production," *J. Exp. Med.*, 186, 1603-1608, Nov. 3, 1997.

Roake, et al., "Dendritic Cell Loss from Non-Lymphoid Tissues After Systemic Administration of Lipopolysaccharide, Tumor Necrosis Factor, and Interleukin-1," *J. Exp. Med.* vol. 181, pp. 2237-2247, Jun. 1995.

Romani, et al., "Generation of Mature Dendritic Cells from Human Blood:An Improved Method with Special Regard to Clinical Applicability," *J. Immunological Methods*, vol. 196, pp. 137-151, 1996.

Romani N., et al., "Presentation of Exogenous Protein Antigens by Dendritic Cells to T Cell Clones: Intact Protein is Presented Best by Immature Epidermal Langerhans Cells," *J. Exp. Med.*, 169, 1169-1178, 1989.

Casciola-Rosen, et al., "Autoantigens Targeted in Systemic Lupus Erythematosus are Clustered in Two Poulations of Surface Structures on Apoptotic Keratinocytes," *J. Exp. Med.*, 179, 1317-1330, Apr. 1994.

Casciola-Rosen, et al., "Ultraviolet Light-Induced Keratinocyte Apoptosis:A Potential Mechanism for the Iduction of Skin Lesions and Autoantibody Production in LE," *Lupus*, vol. 6, No. 2, pp. 175-180, 1997.

Casciola-Rosen, et al., "Surface Blebs on Apoptotic Cells are Sites of Enhanced Procoagulant Activity:Implications for Coagulation Events and Antigenic Spread in Systemic Lupus Erythematosus," *Proc. Natl. Acad. Sci. USA*, vol. 93, pp. 1624-1629, Feb. 1996.

Rosen, et al., "Autoantigens as Substrates for Apoptotic Proteases:Implications for the Pathogenesis of Systemic Autoimmune Disease," *Cell Death and Differentiation*, vol. 6.No. 1, pp. 6-12, Jan. 1999.

Rosen, et al., "Novel Packages of Viral and Self-Antigens are Generated During Apoptosis," *J. Exp. Med.*, vol. 181, No. 4, pp. 1557-1561, Apr. 1995.

Rovere, et al., "Cutting Edge: Bystander Apoptosis Triggers Dendritic Cell Maturation and Antigen-Presenting Function," *The Journal of Immunology*, 161, pp. 4467-4471, 1998.

Rubartelli, et al., "The Selective Engulfment of Apoptotic Bodies by Dendritic Cells is Mediated by the αVβ3 Intergrin and Requires Intracellular and Extracellular Calcium," *Eur. J.Immunol.*, 27:1893-1900, 1997.

Ryeom, S.W., et al., "CD36 Particpates in the Phagocytosis of Rod Outer Segments by Retinal Pigment Epithelium," *Journal of Cell Science*, 109, 387-395, 1996.

Sallusto, et al., "Dendritic Cells use Macropinocytosis and the Mannose Receptor to Concentrate Macromolecules in the Major Histocompatibility Complex Class II Compartment: Downregulation by Cytokines and Bacterial Products," *J. Exp. Med.*, vol. 182, pp. 389-400, Aug. 1995.

Sallusto, et al., "Efficient Presentation of Soluble Antigen by Cultured Human Dendritic Cells is Maintained by Granulocyte/Macrophage Colony-Stimulating Factor Plus Interleukin 4 and Downregulated by Tumor Necrosis Factor α," *J. Exp. Med.*, vol. 179, pp. 1109-1118, Apr. 1994.

Sallusto, F, et al., "Ceramide Inhibits Antigen Uptake and Presentation by Dendritic Cells," *J. Exp. Med.*, 184, 2411-2416, Dec. 1996.

Savill, J., "Phagocytic Docking Without Shocking," *Nature*, 392,442-443, Apr. 1998.

Savill, J., "Recognition and Phagocytosis of Cells Undergoing Apoptosis," *Br. Med. Bull.*, 53, 491-508, 1997.

Savill, J., et al., "Vitronectin Receptor-Mediated Phagocytosis of Cells Undergoing Apoptosis," *Nature*, 343, 170-173, Jan. 11, 1990.

Savill, J. et al., "Thrombospondin Cooperates with CD36 and the Vitronectin Receptor in Macrophage Recognition of Neutrophils Undergoing Apoptosis," *Journal of Clinical Investigation*, 90, 1513-1522, Oct. 1992.

Schamboeck, et al., "Organization of the Transcriptional Unit of a Human Class II Histocompatibility Antigen: HLA-DR Heavy Chain," *Nucl. Acids Res.*, 11, 8663-8675, Dec. 20, 1983.

Schoenberger, S.P., et al., "T-Cell Help for Cytotoxic T Lymphocytes is Mediated by CD40-CD40L Interactions," *Nature*, 393, 480-483, Jun. 1998.

Schulz, et al., "Peptide-Induced Antiviral Protection by Cytotoxic T Cells," *Proc. Natl. Acad. Sci. USA*, 88:991-993, Feb. 1991.

Shen, Z., et al., "Cloned Dendritic Cells can Present Exogenous Antigens on Both MHC Class I and Class II Molecules," *J. Immunol.*, 158, 2723-2730, Mar. 15, 1997.

Silverstein, R.L., et al., "Sense and Antisense CDNA Transfection of CD36 (Glycoprotein IV) in Melanoma Cells. Role of CD36 as a Thrombospondin Receptor," *J. Biological Chemistry*, 267, 16607-16612, Aug. 15, 1992.

Snyder, H.L., et al., "Two Novel Routes of Transporter Associated with Antigen Processing (TAP)-Independent Major Histocompatibility Complex Class I Antigen Processing," *J. Exp. Med.*, 186, 1087-1098, Oct. 6, 1997.

Sornasse, et al., "Loading of Dendritic Cells with Antigen In Vitro or In Vivo by Immunotargeting can Replace the Need for Adjuvant," *Adv. Exp. Med. Biol.*, vol. 329, 1993, pp. 299-303.

Steinman, R.M., et al., "Dendritic Cells in the T Cell Areas of Lymphoid Organs," *Immunol. Rev.*, 156, 25-37, 1997.

Steinman, "The Dendritic Cell System and its Role in Immunogenicity",*Ann. Rev. Immunology*, vol. 9, pp. 271-296, 1991.

Steinkamp, J.A., et al., "Phagocytosis: Flow Cytometric Quantitation with Fluorescent Microspheres," *Science*, 215, 64-66, Jan. 1982.

Sugita, M., et al., "Association of the Invariant Chain with Major Histocompatibility Complex Class I Molecules Directs Trafficking to Endocytic Compartments," *Journal of Biological Chemistry*, 270, 1443-1448, Jan. 20, 1995.

Suss, et al., "A Subclass of Dendritic Cells Kills CD4 T Cells Via FAS/FAS-Ligand-Induced Apoptosis," *J. Exp. Med.*, 183:1789-1796, Apr. 1996.

Suto, et al., "A Mechanism for the Specific Immunogenicity of Heat Shock Protein-Chaperoned Peptides," *Science*, 269, 1585-1588, Sep. 15, 1995.

Szabolcs, et al., "Expansion of Immunostimulatory Dendritic Cells Among the Myeloid Progeny of Human CD34+ Bone Marrow Precursors Cultured With C-Kit Ligand, Granulocyte-Macrophage Colony-Stimulating Factor, and TNF-$\alpha^{1,2}$," *J. Immunol.*, vol. 154, pp. 5851-5861, 1995.

Taylor, M.R., et al., "Lactadherin (Formerly BA46), A Membrane-Associated Glycoprotein Expressed in Human Milk and Breast Carcinomas, Promotes ARG-GLY-ASP (RGD)-Dependent Cell Adhesion," *DNA Cell Biol.*, 16:861-869, Nov. 7, 1997.

Thornberry, N.A., et al., "A Novel Heterodimeric Cycteine Protease is Required in Interleukin-1β Processing in Monocytes," *Nature*, 356, 768-774, Apr. 30, 1992.

Van Der Bruggen, P., et al. "A Gene Encoding an Antigen Recognized by Cytolytic T Lymphocytes on a Human Melanoma," *Science*, 254:1643-1647, Dec. 13, 1991.

Voll, R.E., et al., "Immunosuppressive Effects of Apoptotic Cells," *Nature*, 390, 350-351, Nov. 27, 1997.

Vremec, D., et al., "The Surface Phenotype of Dendritic Cells Purified from Mouse Thymus and Spleen: Investigation of the CD8 Expression by a Subpopulation of Dendritic Cells," *J. Exp. Med.*, 176, 47-58, Jul. 1992.

Wang, et al., "Human Tumor Antigens Recognized by T Lymphocytes: Implications for Cancer Therapy," *Journal of Leukocyte Biology*, vol. 60, pp. 296-309, Sep. 1996.

Watts, C., "Capture and Processing of Exogenous Antigens for Presentation on MHC Molecules," *Annu. Rev. Immunol.*, 15, 821-850, 1997.

Wong, B.R., et al., "Transce (Tumor Necrosis-Factor [TNF]-Related Activation-Induced Cytokine), A New TNF Family Member Predominately Expressed in T Cells, is a Dendritic Cell Specific Survival Factor," *J. Exp. Med.*, 186, 2075-2080, Dec. 15, 1997.

Wraith, et al., "Antigen Recognition in Autoimmune Encephalomyelitis and the Potential for Peptide-Mediated Immunotherapy," *Cell*, vol. 59, pp. 247-255, 1989.

Wraith, et al., "Influenza Virus-Specific Cytotoxic T-Cell Recognition: Stimulation of Nucleoprotein-Specific Clones with Intact Antigen", *Immunology*, vol. 59, pp. 173-180, 1986.

Wyllie, "Apoptosis and Carcinogenesis," *European Journal of Cell. Biol.*, 73:189-197, Jul. 1997.

Wyllie, A.H., "Glucocorticoid-Induced Thymocyte Apoptosis is Associated with Endogenous Endonuclease Activation,"*Nature*, 284, 555-556, Apr. 1980.

Wysocka, et al., "Identification of Overlapping Class I and Class II H-$2^d$- Restricted T Cell Determinants of Influenza Virus N1 Neuraminidase that Require Infectious Virus for Presentation," *Virol.*, vol. 201: 86-94, 1994.

Young, et al., "Dendritic Cells as Adjuvants for Class I Major Histocompatibility Complex-Restricted Antitumor Immunity," *J. Exp. Med.*, vol. 183, pp. 7-11, Jan. 1996.

Young, et al., "Dendritic Cells Stimulate Primary Human Cytolytic Lymphocyte Responses in the Absence of CD4+ Helper T Cells," *Journal of Experimental Medicine*, vol. 171, pp. 1315-1332, Apr. 1990.

Zal, T., et al., "Mechanisms of Tolerance Induction in Major Histocompatibility Complex Class II-Restricted T Cells Specific for a Blood-Borne Self-Antigen," *J. Exp. Med.*, 180, 2089-2099, Dec. 1994.

Zhou, F., et al., "Liposome-Mediated Cytoplasmic Delivery of Proteins: An Effective Means of Accessing the MHC Class 1-Restricted Antigen Presentation Pathway," *Immunomethods*, 4:229-235, 1994.

Zhou, et al., "Human Blood Dendritic Cells Selectively Express CD83, A Member of the Immunoglobulin Superfamily," *The Journal of Immunology*, vol. 154, pp. 3821-3835, 1995.

Zitvogel, L., et al, "Therapy of Murine Tumors with Tumor Peptide Pulsed Dendritic Cells: Dependence on T-Cells, B7 Costimulation, and T Helper Cell 1-Associated Cytokines," *J. Exp. Med.*, in Press, vol. 183,87-97, Jan. 1996.

Zoochi, M.R., et al., "The RGD-Containing Domain of Exogenous HIV-1 TAT Inhibits the Engulfment of Apoptotic Bodies by Dendritic Cells," *AIDS*, 11:1227-1235, Aug. 1997.

* cited by examiner

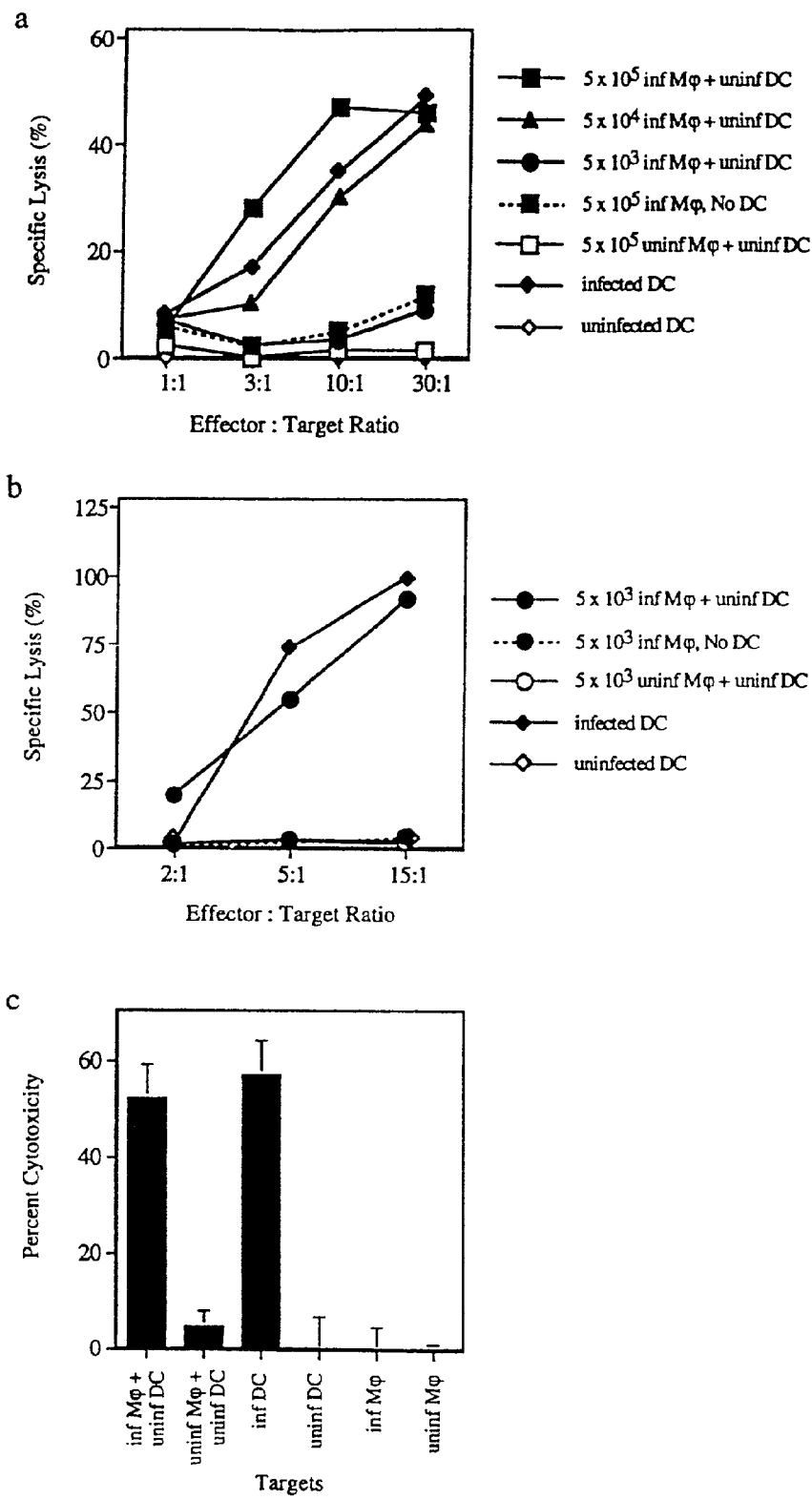
FIG. 1A-C

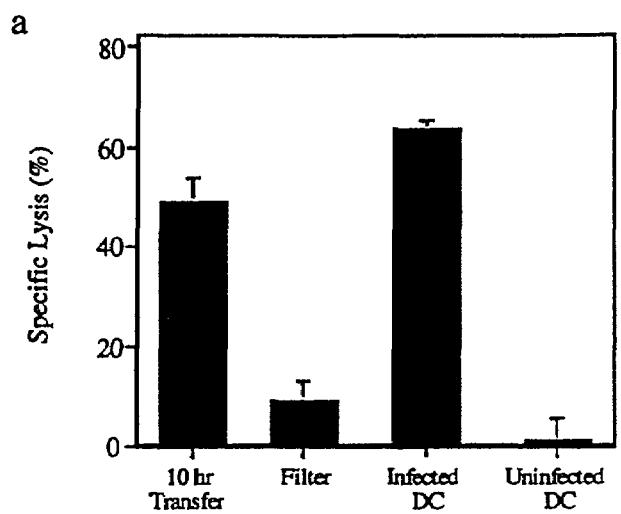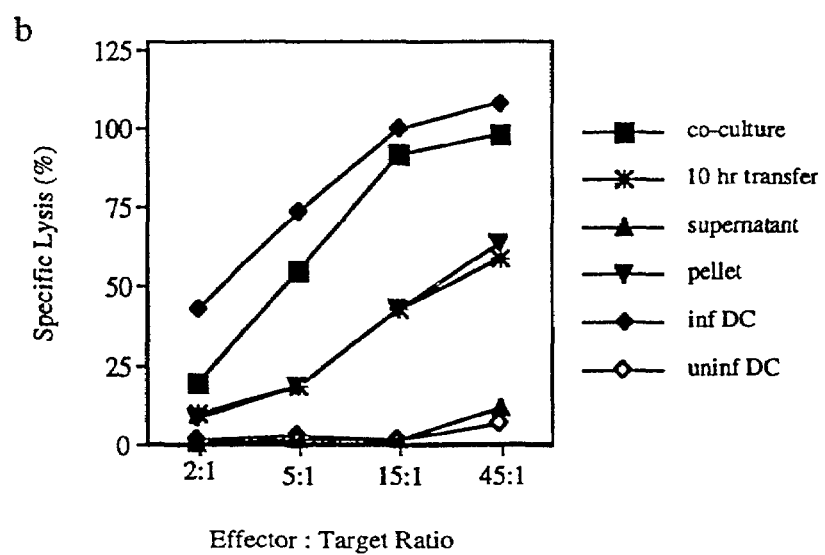
FIGS. 2A-B

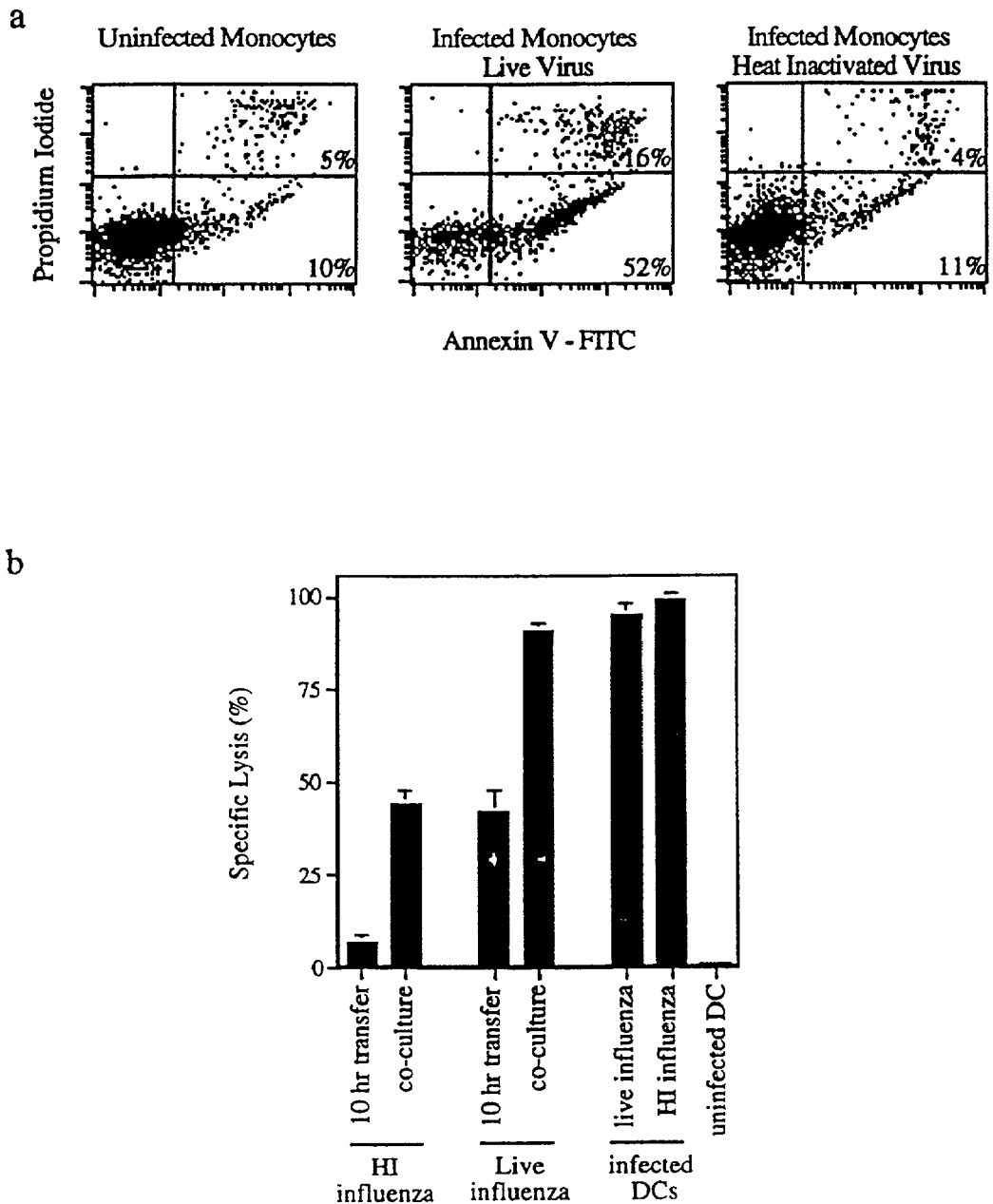
FIGS. 3A-B

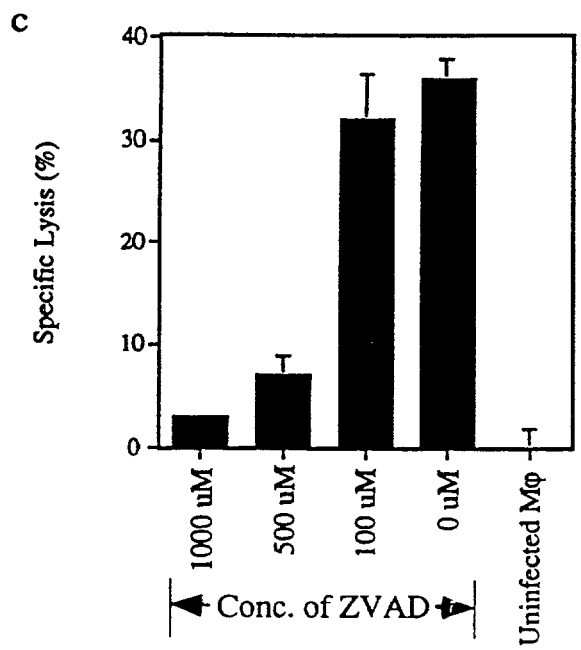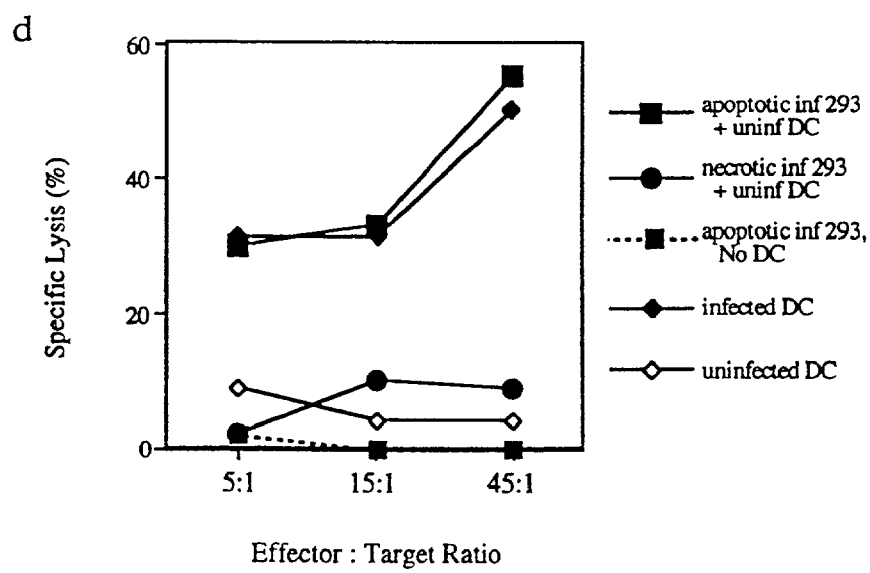
FIGS. 3C-D

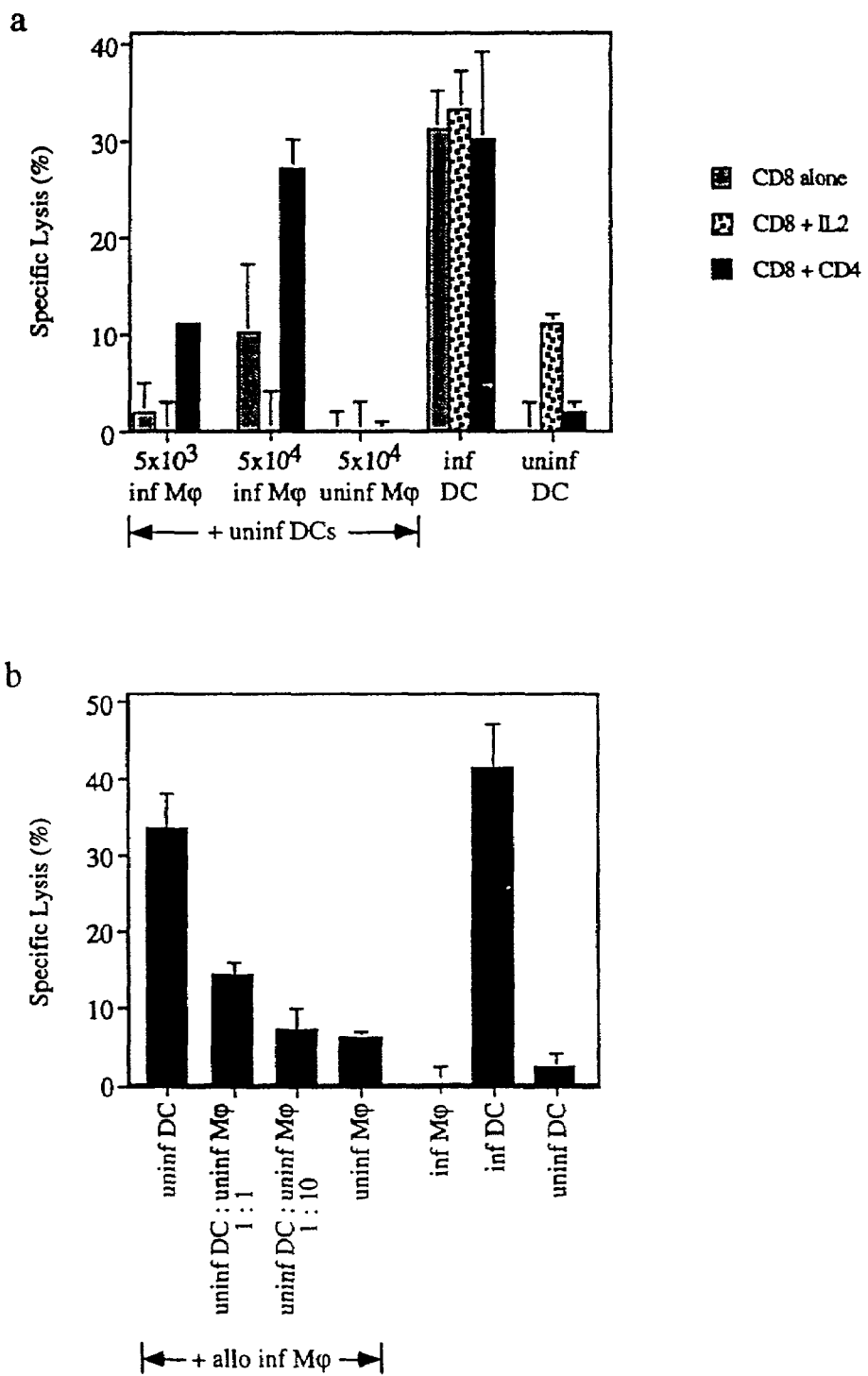
FIG. 4A-B

A
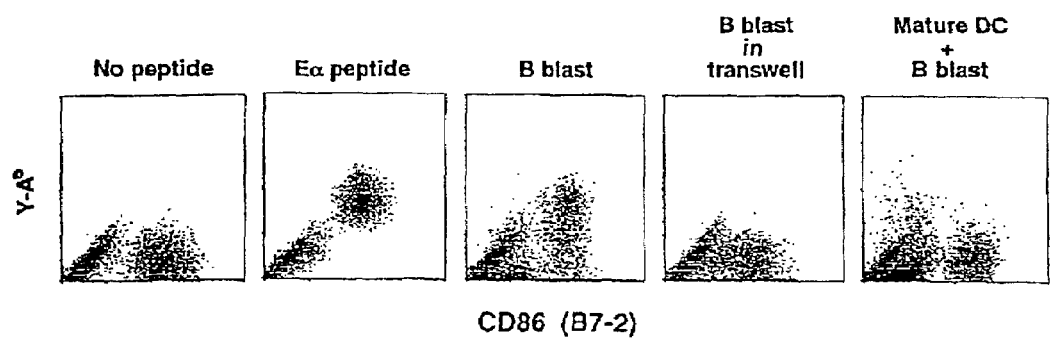
B
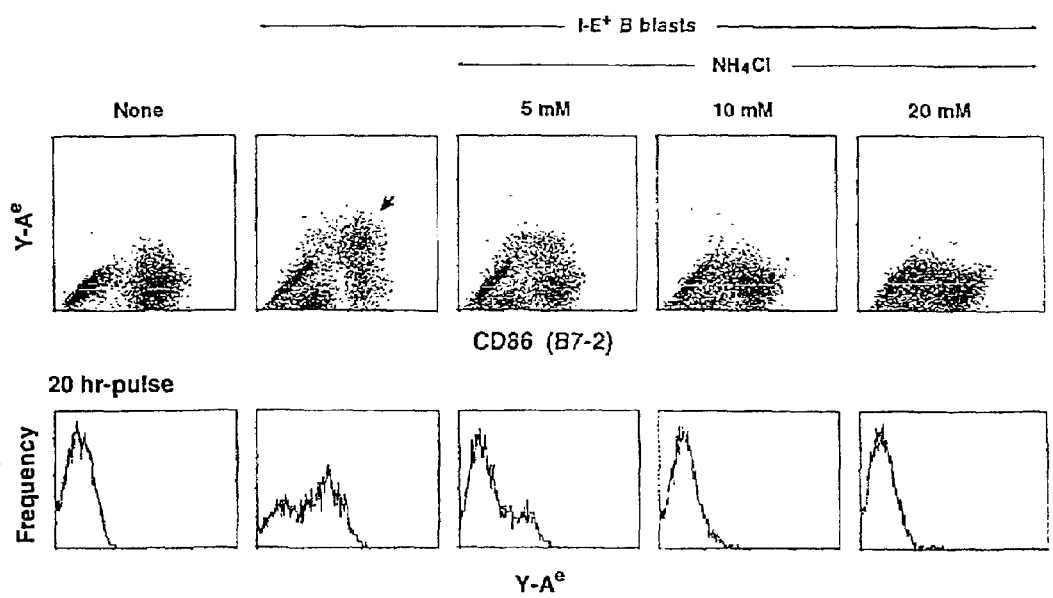
FIGS. 11A-B

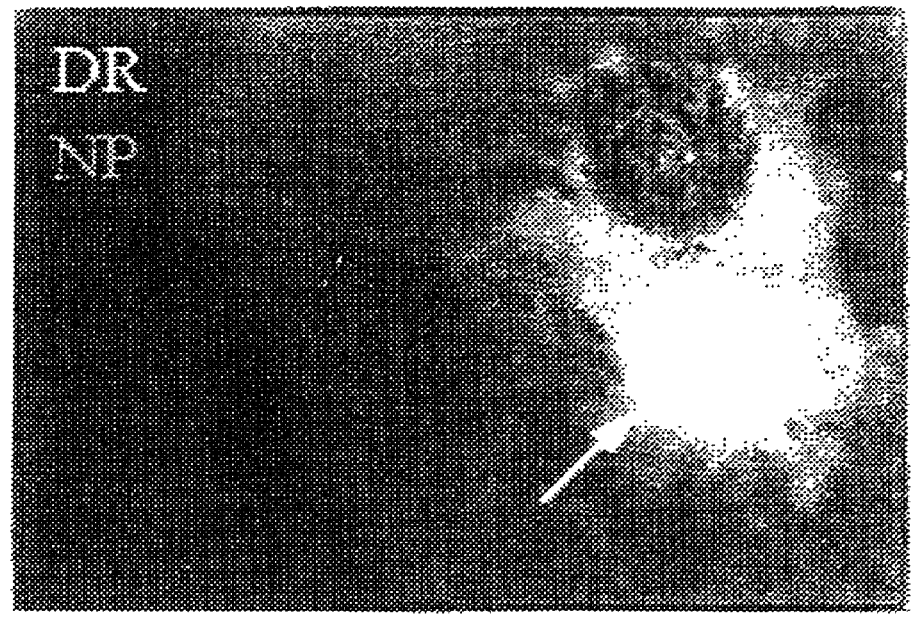
FIG. 16

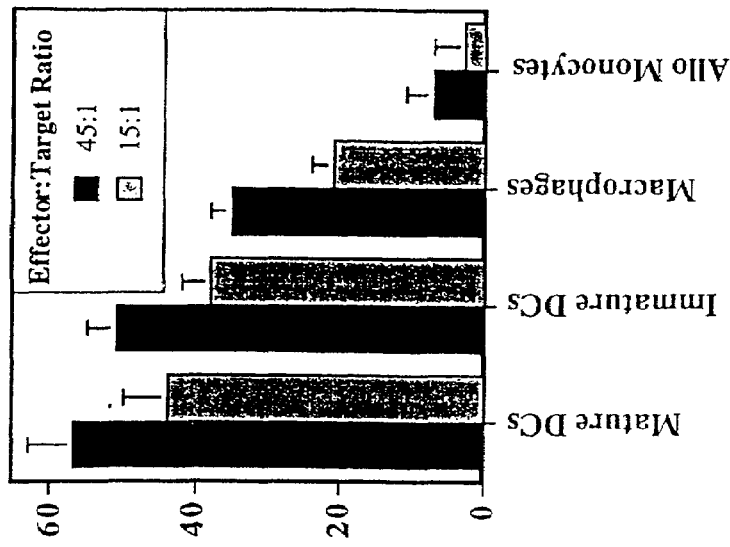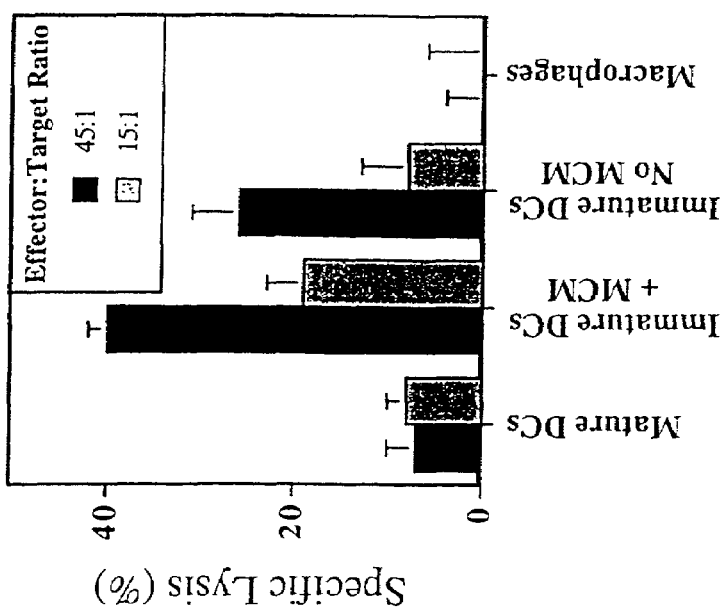
FIGS. 17A-B

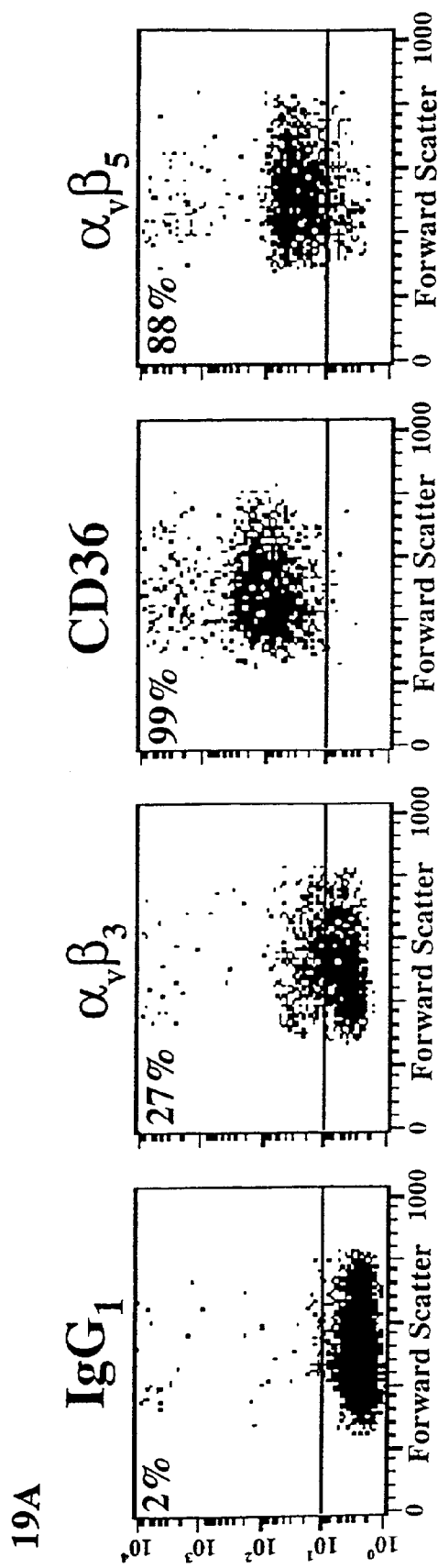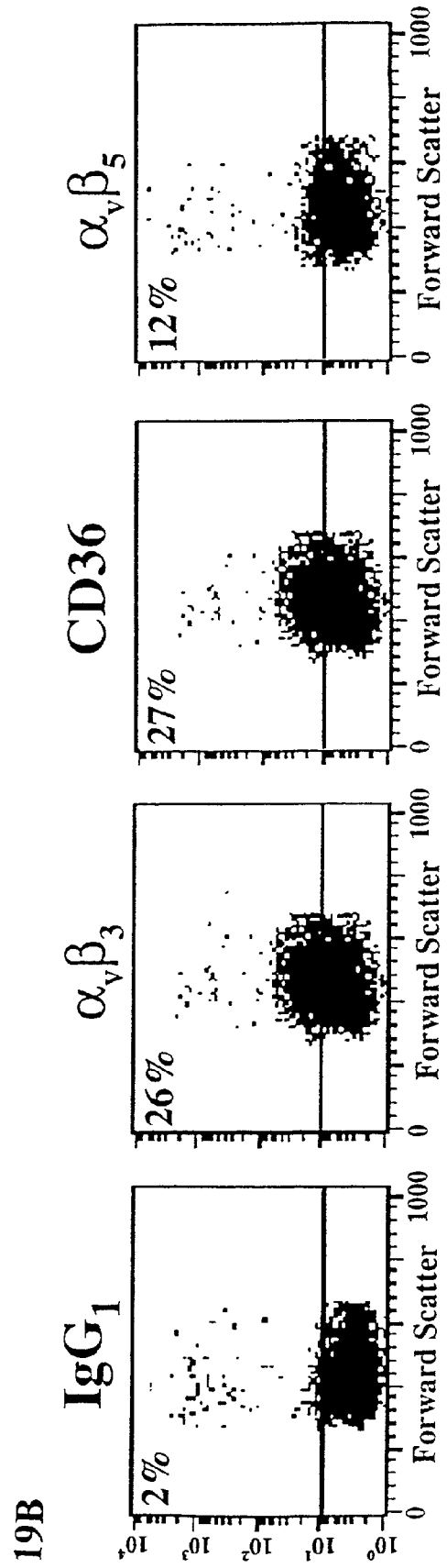
FIGS. 19A-B

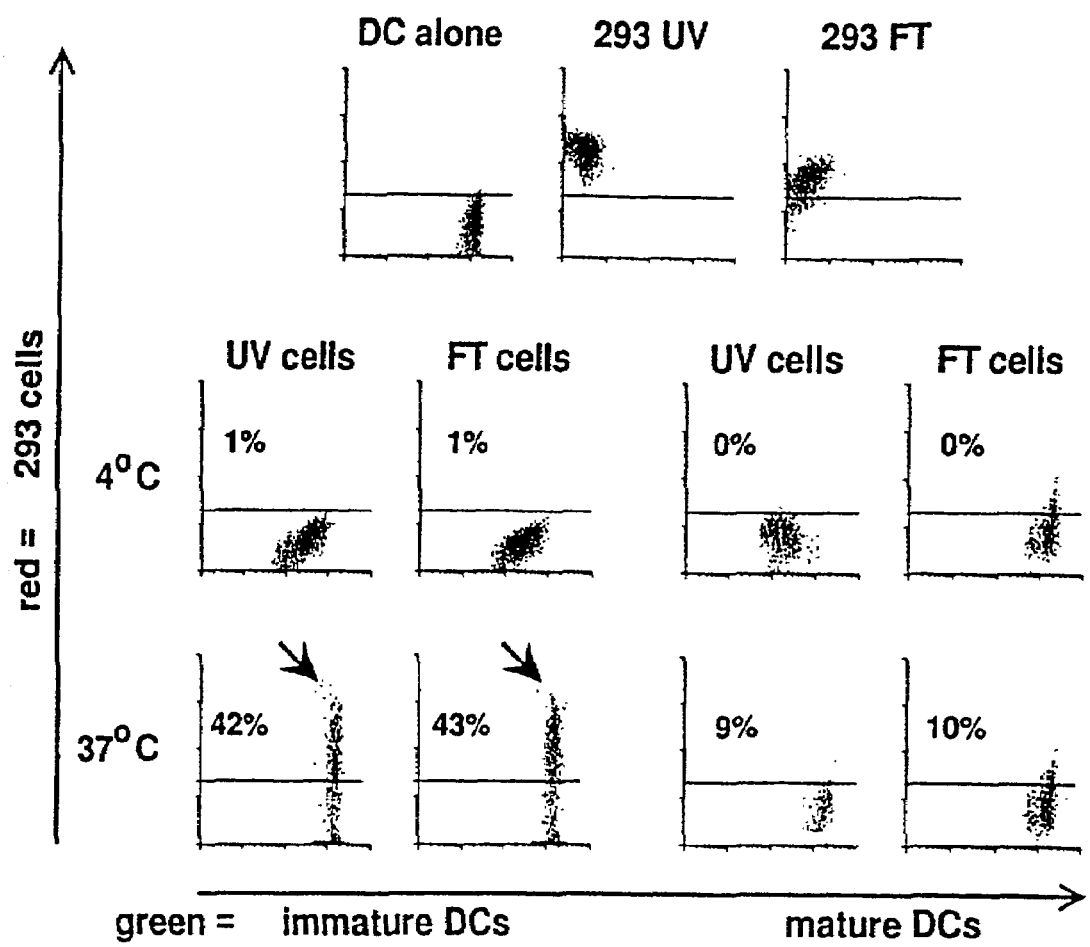

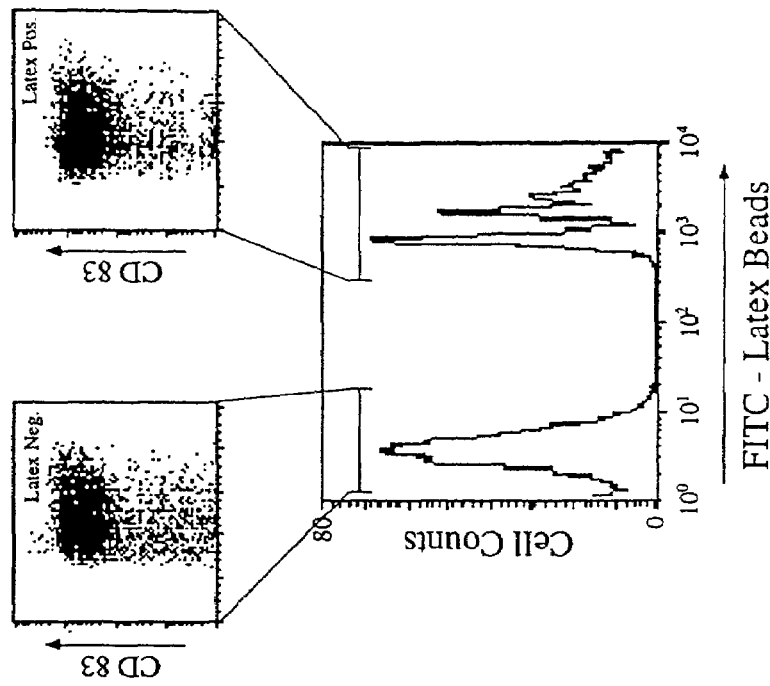
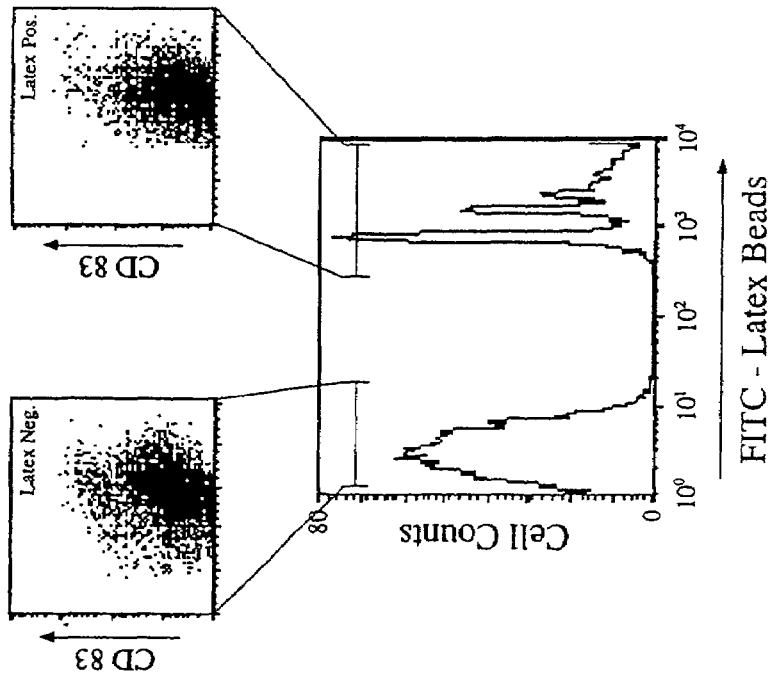
FIGS. 21D-E

METHODS FOR USE OF APOPTOTIC CELLS TO DELIVER ANTIGEN TO DENDRITIC CELLS FOR INDUCTION OR TOLERIZATION OF T CELLS

This application is a continuation of U.S. application Ser. No. 09/251,896, filed Feb. 19, 1999, now U.S. Pat. No. 6,602,709, which claims priority to U.S. provisional applications Ser. No. 60/075,356, filed Feb. 20, 1998; Ser. No. 60/077,095, filed Mar. 6, 1998; and Ser. No. 60/101,749, filed Sep. 24, 1998, all of which are incorporated herein by reference in their entireties.

This invention was made with United States Government support under National Institutes of Health grant AI-39516, AI-13013 and AI 39672. The United States Government has certain rights in this invention.

FIELD OF THE INVENTION

This invention relates to targeted antigen presentation in the immune system. In particular, this invention relates to the use of apoptotic cells to deliver antigens to dendritic cells for induction or tolerization of antigen-specific T cell responses. The apoptotic cell-mediated antigen delivery system described herein has a wide range of preventive, diagnostic and therapeutic applications.

BACKGROUND OF THE INVENTION $CD8^+$ cytotoxic T lymphocytes (CTLs) play a critical role in immune defense against infectious agents, tumors and transplants. Class I-restricted $CD8^+$ T cells have been implicated in the recognition and destruction of such clinically important targets as HIV-1 (1–3), Influenza A (4), malaria (5), cytomegalovirus infected cells (6), Epstein-Barr virus (7), and human melanoma cells (8–9). Therefore, establishing methods for inducing and expanding populations of antigen-specific $CD8^+$ CTLs remains an important objective in the development of therapeutic treatments against infectious disease and cancer.

$CD8^+$ CTLs are activated by antigens which have been processed and presented on major histocompatibility (MHC) class I molecules on the surface of specialized antigen presenting cells. A number of antigen presenting cells have been identified which activate T cells including macrophages/monocytes, B cells and bone marrow derived dendritic cells. Of these, dendritic cells are recognized as playing a pivotal role in the initiation of $CD8^+$ CTL responses (10).

An important feature of dendritic cells is their ability to efficiently process and present antigens on MHC class I and/or class II molecules. Depending on the antigen processing pathway, dendritic cells are capable of activating distinct populations of CTLs. In the case of influenza virus, for example, it is known that the class I pathway for inducing $CD8^+$ CTLs requires adequate delivery of infectious viral antigen into the cytoplasm, whereas the purely endocytic pathway delivers noninfectious virions for presentation only to $CD4^+$ T helper cells (U.S. Ser. No. 08/282,966). Thus, although dendritic cells efficiently activate class I-restricted CTLs, access to the MHC class I pathway for induction of $CD8^+$ T cells normally requires endogenous synthesis of antigen. Accordingly, it is important to identify antigen delivery systems which efficiently mediate access of exogenous antigen to the MHC class I-restricted antigen presentation pathway in order to generate antigen-specific $CD8^+$ T cell responses.

Recently, a number of approaches have been reported for delivery of exogenous antigen to the MHC I processing pathway of dendritic cells. These methods include coupling antigens to potent adjuvants (11–15), osmotic lysis of pinosomes after pinocytic uptake of soluble antigen (16), or insertion of antigen in pH-sensitive liposomes (17). However, these prior approaches still pose a number of limitations on the development of effective therapeutic treatments. For example, Nair et al. report that dendritic cells do not efficiently internalize antigen-containing liposomes in vivo (18). Further, osmotic lysis of dendritic cell pinocytic vesicles may be difficult to perform in vivo, and may result in inefficient antigen delivery to the MHC class I processing compartment. Also, the use of powerful adjuvants may be undesirable for some clinical applications.

Pulsing dendritic cells directly with exogenous antigen using whole cells in viable or irradiated forms, membrane preparations, or antigens purified from natural sources or expressed as recombinant products has also been previously reported (WO 94/02156). These prior methods, however, do not recognize forms of cell death or the processing pathways antigens from dead or dying cells access in the dendritic cell system.

Rubartelli et al. report that dendritic cells, unlike macrophages, fail to take up opsonized particles or necrotic cells in vitro, but can efficiently engulf cells undergoing apoptotic programmed cell death (19). The mechanism of internalization of apoptotic cells by dendritic cells, however, is different than in macrophages, indicating that results in the macrophage system are not necessarily predictive of dendritic cell responses. In addition, Rubartelli et al. does not show presentation of engulfed material and therefore speculates as to the fate of such material.

SUMMARY OF THE INVENTION

This invention provides highly efficient methods for delivering exogenous antigens to dendritic cells and inducing antigen-specific T cell activation. In particular, the methods described in this invention are directed toward developing therapies for increasing patient immunity to chronic infections and tumors by 1) inducing tumor or infected cells to undergo apoptosis, 2) having the apoptotic tumor or infected cells gain access to phagocytic, maturing dendritic cells, and 3) exposing the apoptotic cell-primed dendritic cells expressing antigen of interest to T cells, in vivo or in vitro, for induction of antigen-specific T cell responses.

This invention further provides that the population of donor cells expressing said antigen can be induced to undergo apoptosis using a variety of methods including, but not limited to, viral infection, irradiation with ultraviolet light, gamma radiation, cytokine treatment, or depriving donor cells of nutrients in the cell culture medium. It is also contemplated by this invention that the dendritic cells can be exposed to a preparation of donor apoptotic cell fragments, blebs or bodies rather than whole apoptotic cells.

In another embodiment of this invention, the donor cells can be transfected, transduced or transformed to express foreign antigens prior to induction of apoptosis. A variety of such antigens may be expressed by the donor cells including, but not limited to, viral antigens, tumor antigens, toxins, microbial antigens, and autoimmune antigens.

Accordingly, this invention also provides a method of generating antigen-specific cytotoxic T lymphocytes comprising providing a population of apoptotic cells, or membrane containing fragments thereof, expressing said antigen, exposing dendritic cells to said apoptotic cells for a time sufficient to allow said antigen to be internalized and processed by the dendritic cells, and exposing T lymphocytes in vivo to said dendritic cells for a time sufficient to induce said lymphocytes to become antigen-specific T lymphocytes. This invention further contemplates induction of antigen-specific T lymphocytes in vitro.

In another embodiment of this invention apoptotic cells expressing an antigen to be presented by dendritic cells are administered to an individual in an amount and in a location so as to prime dendritic cells in vivo.

Methods of preventing and treating disease are also provided by this invention which comprises administering to an individual in need of treatment, a therapeutically effective amount of dendritic cells which have been primed by apoptotic cells.

In addition to the methods of this invention, this invention also provides dendritic cells which have been primed by apoptotic cells, and in particular, human dendritic cells which are prepared according to the methods of this invention. This invention further provides transformed apoptotic cells, or a preparation of transformed apoptotic cell fragments, and in particular, human apoptotic cells which are prepared according to the methods of this invention.

In another embodiment of this invention the apoptotic cell delivery system is reconstituted in vitro using liposomes comprising antigen and apoptotic cell proteins, factors or ligands which enhance uptake and processing of antigen in dendritic cells.

Based on the results disclosed herein, one may include in a liposome ligands for integrin receptors, including, but not limitd to the $\alpha_v\beta_5$ and $\alpha_v\beta_3$ integrin receptors for enhancing uptake and processing of antigens in dendritic cells. An example of such a ligand is lactadherin. Other examples of proteins which may enhance uptake of apoptotic particles include thrombospondin. Similarly, ligands which bind CD36 may also be used. In a preferred embodiment ligands for both integrin and CD36 would be used.

Heat shock proteins (HSP) may also be included to facilitate antigen uptake by dendritic cells. For example, HSP 70 family members, especially HSP 70, and HSP 90 members, especially HSP 84 and GP 96 may be used. Certain antigens obtained from infectious sources may already be bound to HSPs. Alternatively, antigens may be complexed to HSP ex vivo.

The identification of the $\alpha_v\beta_5$ integrin receptor as mediating antigen uptake by dendritic cells provides one with a means of modulating that antigen uptake by either increasing or decreasing the activity of the $\alpha_v\beta_5$ receptor. Accordingly, this invention provides means for enhancing antigen uptake and processing by dendritic cells in vitro or in vivo, by adding an $\alpha_v\beta_5$ ligand to the dendritic cells in conjunction with the antigen to be taken up and processed. Alternatively, one could attenuate the antigen uptake activity of the dendritic cells by blocking the $\alpha_v\beta_5$ receptor, or other receptors which are involved in medrating antigen uptake by the dendritic cells.

This invention also includes pharmaceutical compositions for charging dendritic cells comprising a ligand which activates antigen uptake, such as an $\alpha_v\beta_5$ ligand, with or without an antigen to be processed and presented by dendritic cells. As used in this invention such ligands may be considered to function as immunoadjuvants.

This invention also provides methods for modulating T cell responses in vivo or in vitro to induce immunity or tolerance by controlling DC maturation.

In one embodiment, T cell immunity can be induced when immature DCs are caused to mature by the addition of appropriate maturation factors after the uptake of apoptotic particles. Examples of maturation factors that can be used in this invention include monocyte conditioned medium, TNF-$\alpha$, IL-1$\beta$, IL6, PGE$_2$, IFN-$\alpha$, CD40 ligand, and necrotic cells.

In another embodiment, tolerance can be induced to self or foreign antigens by maintaining DCs in their immature state in the absence of a maturation signal.

It is a general object of this invention to provide a method of using apoptotic cells, or apoptotic cell fragments, to efficiently deliver specific antigens to dendritic cells which then process and present said processed antigens on their surface for stimulation or tolerization of cytotoxic T lymphocytes.

It is another object of this invention to generate antigen-specific cytotoxic T lymphocytes either in vivo or in vitro by using the dendritic cells generated by the methods described herein.

It is also an object of this invention to provide a method of prophylactic or therapeutic treatment for a variety of cancers, autoimmune diseases, and pathogens using the dendritic cells described herein.

DESCRIPTION OF FIGURES

FIGS. 1a, 1b and 1c: Dendritic cells acquire antigen from influenza-infected cells and induce class I-restricted CTLs. FIGS. 1a, 1b. Varying doses of influenza-infected syngeneic monocytes [FIG. 1a] and allogeneic HLA-A2.1$^-$ monocytes were co-cultured with DCs and T cells for 7 days. After 8 to 10 hours, 10$^6$ T-cells and 3.3×10$^4$ DCs derived from HLA-A2.1$^+$ were added. On day 7, cytolytic activity was tested using syngeneic influenza-infected macrophages [FIG. 1a] or T2 cells, a HLA-A2.1$^+$ cell line which lacks the transporters of antigen processing or TAP, pulsed with the immunodominant influenza matrix peptide (35,36) [FIG. 1b] as targets. Influenza-infected DCs served as a control in all experiments in order to measure the donor's CTL responsiveness to influenza. Responses varied as a function of the individual's prior exposure to influenza. Background lysis ranged from 0–5% for the uninfected monocytes and 0–20% for the unpulsed T2 cells. FIG. 1c. Uninfected syngeneic DCs were co-cultured with influenza-infected allogeneic monocytes for 2 days prior to being used as targets for CTLs. Control targets included influenza-infected syngeneic DCs and influenza-infected allogeneic monocytes. Effector:target ratio=45:1. These results in FIGS. 1a, 1b and 1c are representative of 8 experiments and the values shown represent the mean from triplicate wells.

FIGS. 2a and 2b: Antigen transfer is not due to live influenza virus or free peptide. [FIG. 2a]. 5×10$^4$ infected allogeneic HLA-A2.1$^-$ monocytes were cultured for 10 hours, after which the media from the wells containing infected monocytes was removed and added to fresh wells containing HLA-A2.1$^+$ T-cells and DCs [10 hr transfer]. Media from the infected monocyte was also passed through a 0.45 micron filter, prior to addition to wells containing HLA-A2.1$^+$1 T cells and DCs [filter]. Effector:target ration=30:1. [FIG. 2b]. 5×10$^3$ infected allogeneic (HLA-A2.1 mismatched) monocytes were cultured for 10 hours, after which T-cells and DCs were added to the wells [filled squares]. Alternatively, the medium from the wells containing infected monocytes (HLA-A2.1 mismatched) was removed and transferred to fresh wells containing T-cells and DCs [stars]. Other cultures were established in which the medium was first spun at 250×g in a GH-3.8 Beckman Rotor for 10 minutes. The resulting supernatant fraction [up triangle] versus the pellet [down triangle] was added to the T cell and DC containing cultures. After 7 days, cytolytic activities in the T cell populations were determined. T2 cells pulsed with the influenza matrix peptide were used as targets. These results are representative of 3 experiments and the values shown represent the mean from triplicate wells.

FIGS. 3a, 3b, 3c and 3d: Apoptosis is required for delivery of antigen to DCs. [FIG. 3a]. Monocytes were infected with live and heat-inactivated influenza virus. After overnight culture, cells were stained with annexin V-FITC [ann V] and propidium iodide [PI], and analyzed by flow cytofluoremetry (FACscan®). Early apoptotic cells are defined by the ann $V^+$, $PI^-$ population (37). [FIG. 3b]. Allogeneic HLA-A2.1$^-$ monocytes were infected with either heat-inactivated, non-replicating influenza virus (15) or with live influenza virus. $5 \times 10^3$ monocytes were cultured for 10 hours, after which the media from the wells containing the infected monocytes was removed and added to fresh wells containing T cells and uninfected DCs [10 transfer]. Alternatively, the infected monocytes were co-cultured with the T cells and DCs [co-culture]. Heat-inactivated influenza and live influenza-infected DCs 1 served as the positive controls for the experiment. After 7 days, T cells were tested for cytolytic activity using T2 cells as targets. [FIG. 3c]. Apoptosis of influenza-infected monocytes was inhibited using Z-VAD-CHO, an irreversible peptide-aldehyde inhibitor of caspases, the enzymes that are involved in the apoptotic pathway. $1 \times 10^4$ infected monocytes were exposed to varying doses of Z-VAD and cultured for 10 hours. The media from these wells was then transferred to fresh wells containing $2 \times 10^5$ T cells and $6.67 \times 10^3$ DCs. Cytolytic activity was determined as in [FIG. 3b]. [FIG. 3d]. Cells of the human kidney epithelial 293 cell line (ATCC), were infected with influenza virus, and cultured for 10 hours at 37° C. Apoptosis was then induced by exposure to 60 mJ/cm$^2$ of UVB irradiation. Necrosis was achieved by incubating the 293 cells in a hypotonic solution for 30 minutes at 37° C., as determined by incorporation of trypan blue. Apoptotic or necrotic 293 cells were co-cultured with T cells and uninfected DCs for 7 days. Cytolytic activity was determined as in [FIG. 3b]. Uninfected 293 cells cultured with T cells and DCs failed to induce virus-specific CTLs [data not shown]. These results in FIGS. 3a–3d are representative of 9 experiments and the values shown represent the mean from duplicate or triplicate wells.

FIGS. 4a and 4b: Generation of CD8+ CTLs requires CD4+ T-cell help and dendritic cells. [FIG. 4a]. $5 \times 10^4$ influenza-infected allogeneic monocytes were co-cultured with DCs and CD8$^+$ T cells. Highly purified CD8$^+$ T cells (13) were cultured either alone, 50 U/ml human IL-2 or with CD4$^+$ T cells. IL-2 was added on days 0 and 3. The ratio of CD8$^+$:CD4$^+$ T cells was 1:3, matching the ratio in peripheral blood. Cytolytic activities were determined using T2 cells pulsed with the influenza matrix peptide as targets. Effector:target ratio=10:1. This data is representative of 3 experiments, each testing various doses of apoptotic monocytes. [FIG. 4b]. Influenza-infected syngeneic monocytes were co-cultured with various APCs and bulk T cells. Uninfected DCs, uninfected monocytes and mixtures of both were used as the APCs. Infected monocytes alone and infected DCs served as controls for the experiment. Cytolytic responses were measured as described. Effector:target ratio=30:1.

[FIG. 5a]. Cells were stained by immunofluorescence with anti-CD8 [isotype control] or anti-p55 followed by goat anti-mouse-FITC and incubation with 4'6' diamidino-2-phenylindole (DAPI) [Sigma]. The nucleus of the DCs [arrows] are lobulated and euchromatic as compared with the pyknotic, fragmented nucleus of apoptotic cells [open arrows]. DAPI$^+$ material from an apoptotic cell appears to be within the cytoplasm of a p55$^+$ DC. [FIG. 5b]. Electron microscopy revealed apoptotic material and apoptotic cells [AC] within the cytoplasm of glutaraldehyde fixed DCs (38). [FIG. 5c]: DCs are identified by immuno-electron microscopy with anti-CD83 visualized by 10 nm gold beads. Inset 1 shows the localization of CD83 [arrows] on the processes of the DC. Note the double membrane in inset 2 [arrowheads], which reveals an apparently intact plasma membrane of the cell. After immuno-labeling the paraformaldehyde fixed DCs, the cell pellet was augmented with glutaraldehyde fixed tumor cells [*].

[FIG. 9a]. Various populations of HLA-A2.1+ professional antigen presenting cells (APCs) were co-cultured with HLA-A2.1– influenza infected monocytes. [FIG. 9b]. Influenza infected CD83$^+$ DCs serve as better targets in a CTL than infected CD83–DCs or CD14$^+$ macrophages. Controls included infected and uninfected APCs. HLA-A2.1– monocytes were also tested as targets to demonstrate the absence of lysis when using a mis-matched target. Effector:Target Ratios=45:1 and 15:1.

[FIG. 10A]: C57BL/6, I-1$^b$ DCs were cultured 20 hrs with no peptide, with 10 µM preprocessed peptide, or with $2 \times 10^6$ B blasts from H-2d BALB/C [I-E$^+$] or H-2b C57BL/6 [I-E$^-$] mice. The cultures were labeled with biotin Y-Ae antibody that recognizes the complex of I-Ab and I-E peptide [y-axis] and CD86 costimulator. The CD86-rich DCs [black arrows] acquire I-E peptide. No labeling is seen with an IgG2b isotype control to Y-Ae [bottom row].

[FIG 10B]: As in FIG 10a, but DC-BALB/C blast co-cultures [top] or DCs only [bottom] were labeled with other mAbs to show that CD11c$^+$ I-Ab$^+$ I-Ad$^-$ DCs selectively acquired Y-Ae [arrows].

[FIG. 10C]: As in FIG. 10a, C57BL/6 DCs were cultured for the indicated times with different doses of I-Eα peptide or $2 \times 10^6$ B blasts from BALB/C mice and double labeled for Y-Ae and CD86. Y-Ae signals [Mean Fluorescence Index] are shown for CD86$^+$ mature DCs.

[FIG. 10D]: As in FIG. 10a, but graded doses of B blasts [4 days LPS stimulation] and small B cells were compared as a source of I-Eα peptide.

[FIG. 10E]: As in FIG. 10a, but the DCs were sorted from the 20 hr cultures of DCs with peptide or B blasts and used to stimulate IL-2 production [3H-thymidine uptake] from a T-T hybridoma specific for a comparable epitope to the Y-Ae monoclonals.

FIGS. 11A, 11B, 11C and 11D: Antigen transfer requires cellular processing and occurs from xenogenic cells.

[FIG. 11A]: To rule out transfer of peptide from B cells to DCs, B blasts were separated from immature DCs [6 day mouse bone marrow cultures] by a Transwell filter or added to mature DCs, isolated as single nonadherent cells from day 8 mouse marrow cultures [methods].

[FIG. 11B]: Y-Ae epitope formation is blocked by $NH_4Cl$. DCs were cultured 20 h with B blasts with or without $NH_4Cl$ at 5–20 mM. The cultures were stained for Y-Ae and CD86.

[FIG. 11C]: EBV-transformed human B cell lines [0, 0.5 or 5 cells/DC; frequency plots, top] or human monocytes [3 cells/DC; dot blots bottom] serve as a source of I-Eα peptide. The monocytes were untreated, subject to freeze thawing, or induced to apoptose by infection with influenza [monocytes-flu] or by UV light [not shown].

[FIG. 11D]: Development of MHC-peptide complexes consisting of a B cell-derived I-Eα peptide and DC-derived, $I-A^b$ MHC II products. EBV-transformed human B cells lines (3 cells/DC; necrotic and apoptotic) served as a source of I-Eα peptide for mouse DCs. An isotype-matched IgG2b antibody was used as a control for the specific Y-AE labeling that developed on the CD86-rich DCs.

[FIG. 12C]. Same as FIG. 12A, but the sorted DCs were used to stimulate IL-2 release from a T-T hybrid specific for the $I-A^b$/Ep complex [IL-2 monitored by DNA synthesis in test T blasts]. If the DCs were cultured with B blasts in the absence of $NH_4Cl$ [ ], there is strong T cell stimulation, even if the DCs were fixed. However, if the DCs were cultured with B blasts and $NH_4Cl$ [ ], then there is regeneration of the T cell epitope if the DCs are not fixed prior to the 24 hr culture with T cells [compare left and right].

[FIG. 13A]: 2×10$^6$ mature, marrow-derived, H-2d DCs were injected into the foot pads of H-2b mice. 2 days later, sections of the popliteal nodes were stained for Y-Ae [blue] and B220 B cell marker [brown] and photographed at low and high power [50 and 200×]. Blue dendritic profiles were scattered throughout the T cell areas.

[FIG. 13B]: As in FIG. 13A, but cell preparations enriched in DCs were examined by FACS. Several mouse strains were tested as donors and recipients of the marrow-derived DCs. F1 mice [left column] were used as a positive control. The cells were double labeled for Y-Ae or isotype matched control mAb [y-axis] and for different markers [x-axis]. Y-Ae$^+$ DCs [black] and B cells [white] are arrowed.

Freshly isolated, blood monocytesu were infected with live influenza A, PR/8 [Spafas Inc.], labeled with the PKH26-GL fluorescent cell linker compound [Sigma Biosciences], and incubated at 37° C. for 6–8 hours allowing apoptosis to occur. Macrophages, immature DCs and mature DCs were dyed with PKH67-GL and added to the culture wells containing the apoptotic monocytes at a ratio of 1:1. Cells were analyzed by FACScan® where double positive cells indicate uptake of the apoptotic cells by the various APCs [panels iii., vi., ix]. We used the various APCs alone to establish the proper settings [panels i., iv., vii.] Note, as the forward scatter of the APCs increased, the dying monocytes were excluded from the established region [panels ii., v., viii.]. After 2 hr., 80% of the macrophages 50% of the immature DCs, and less than 10% if the mature DCs had engulfed the apoptotic monocytes [A]. In an independent experiment, macrophages [squares], immature DCs [diamonds] and mature DCs [circles] were prepared and co-cultures with apoptotic monocytes were established as described above, and FACS® was performed at various time points. Percent phagocytosis was calculated based on the number of double positive cells [B].

Figure 15:
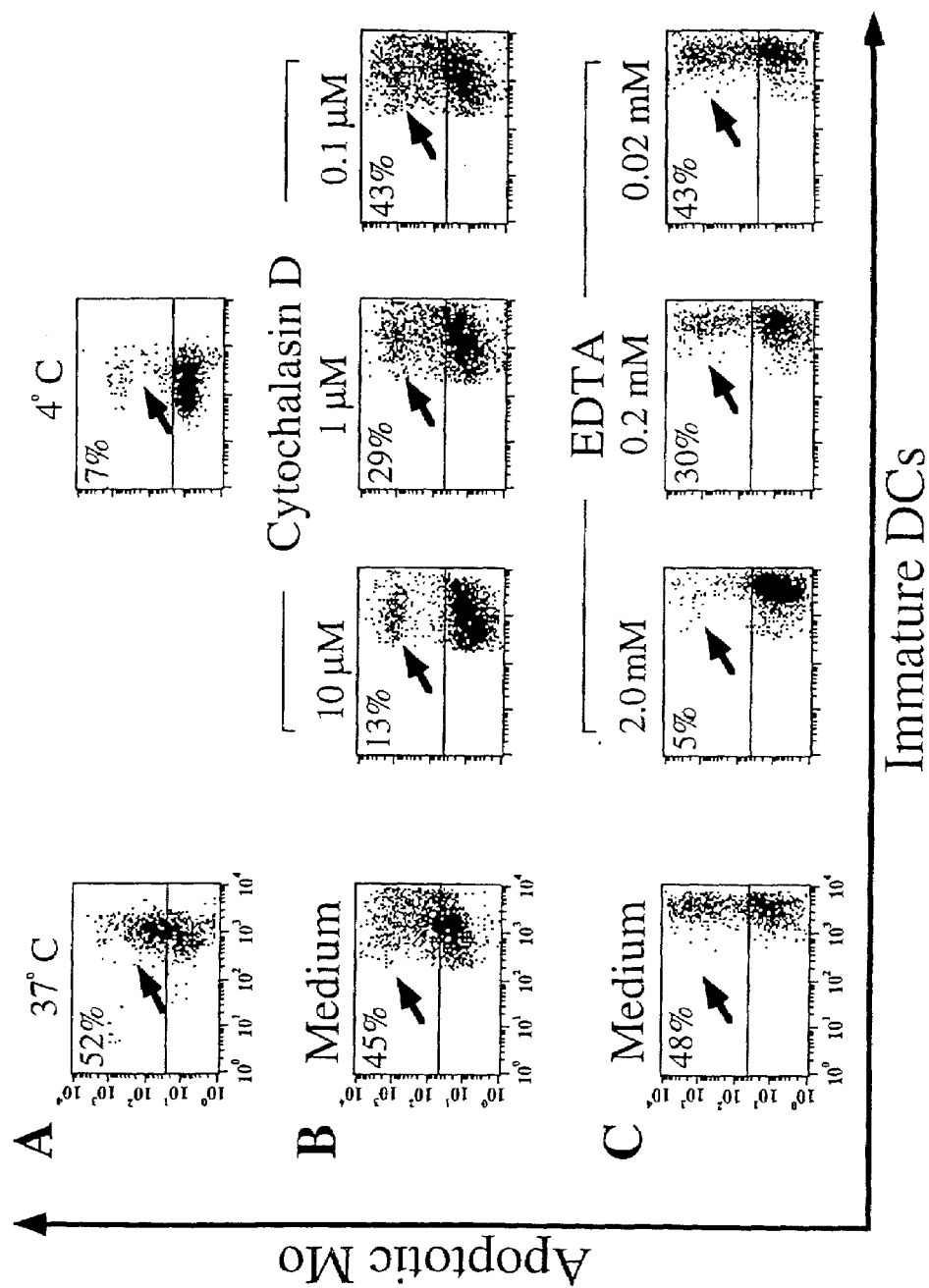

FIG. 15: Low temperature, Cytochalasin D and ETDA block phagocytosis of apoptotic cells by immature DCs.

Apoptotic monocytes and immature DCs were prepared as described. Immature DCs were pre-incubated at 4° C. [A], in the presence of varying concentrations of Cytochalasin D [B], or EDTA [C] for 30 minutes. Apoptotic monocytes were then added to the DC cultures at 4° C. [A] or 37° C. [B,C]. FACS® analysis was performed after 1–2 hrs. Data shown in FIG. 2 are representative of 5 independent experiments in which influenza infected monocytes or UVB irradiated HeLa cells were sources of apoptotic food for the immature DCs. Percent inhibition +/− standard deviation for these experiments were: 4° C., 85%+/−7%; 10 µM Cytochalasin D, 69%+/−3%; and 2 mM EDTA, 76%+/−14%.

FIG. 16: Immature DCs engulf influenza infected monocytes.

Influenza infected apoptotic monocytes were co-cultured with immature DCs for 1 hr after which the cells were adhered to a cover slip and fixed with acetone. Immunofluorescence was performed with anti-influenza nucleoprotein antibodies [NP] and Texas red conjugated goat anti-mouse IgG; and biotinylated anti-HLA-DR [DR] followed by FITC conjugated streptavidin. Large arrowhead indicates apoptotic cell outside the DC prior to engulfment. Small arrows indicate apoptotic material derived from the influenza infected monocytes within DR$^+$ vesicles of the DC. These image were not generated on a confocal scope, so the structures of the DC underlying the apoptotic cell can be seen.

FIGS. 17A and 17B: Immature DCs but not mature DCs nor macrophages cross-present antigenic material derived from apoptotic cells.

Various populations of HLA-A2.1$^+$ antigen presenting cells [APCs] were co-cultured with HLA-A2.1$^-$ influenza infected monocytes. After 12 hrs, the APCs were loaded with $^{51}$Cr and used as targets for HLA-A2.1$^+$ influenza-reactive CTL lines. Mature DCs were isolated by labeling with the DC-restricted marker CD83, followed by cell sorting on the FACSort® [Becton Dickinson]. Immature DCs were CD14$^-$ and sorted by FACSort® as a CD83$^-$ population. Mature macrophages were generated by culturing an adherent mononuclear cell fraction in a Teflon beaker for 9 days. Effector:Target Ratios=45:1 and 15:1 [A]. Controls included infected and uninfected mature DCs, immature DCs and macrophages. The HLA-A2.1$^-$ monocytes used as a source of apoptotic material were also tested as targets to demonstrate the absence of lysis when using a mis-matched target. Effector:Target Ratios=45:1 and 15:1. Results are representative of 3 experiments and the values shown represent the mean of triplicate wells [B].

Figure 18A:
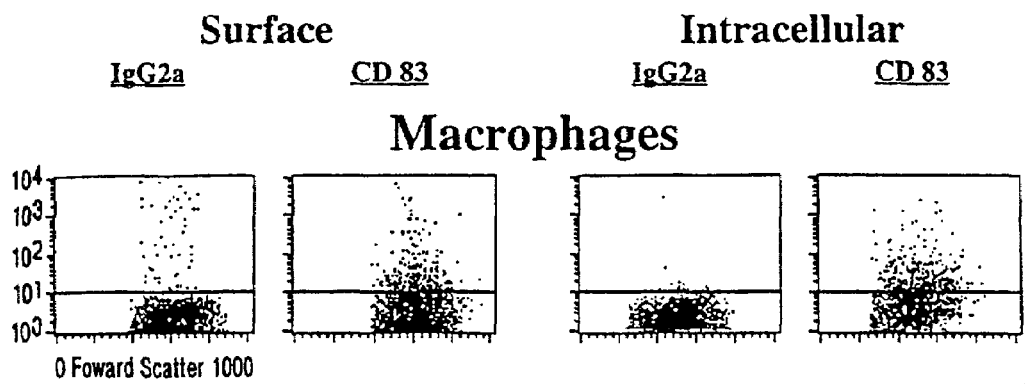
Figure 18B:
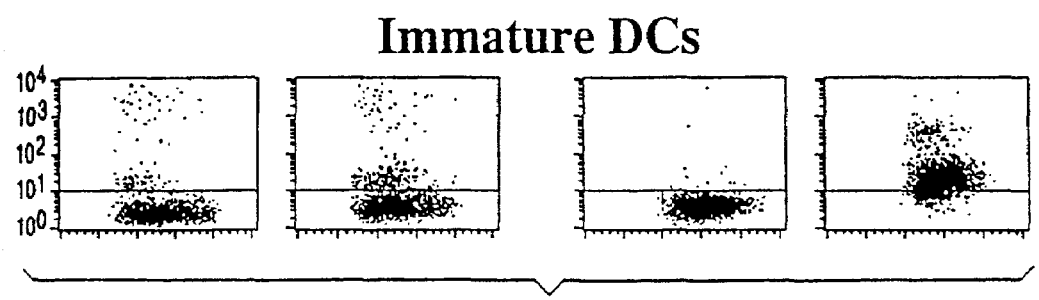
Figure 18C:
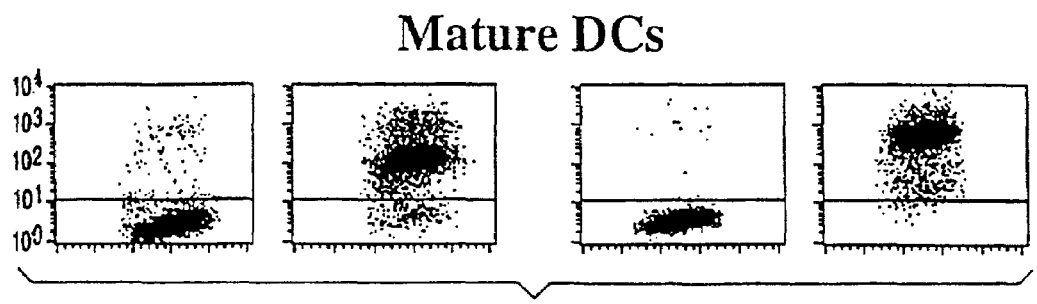

FIG. 18: Intracellular but not extracellular CD83 expression distinguishes immature DCs from mature DCs and macrophages.

Macrophages [A], immature DCs [B] and mature DCs [C] were prepared as previously described. Cells were incubated with anti-CD83, a DC maturation marker, either untreated or post-saponin treatment. The latter permeablized the cells allowing for intracellular staining. Cells were then labeled using a PE-conjugated GAM-Ig [Biosciences] A control isotype matched antibody was used.

Figure 19C:
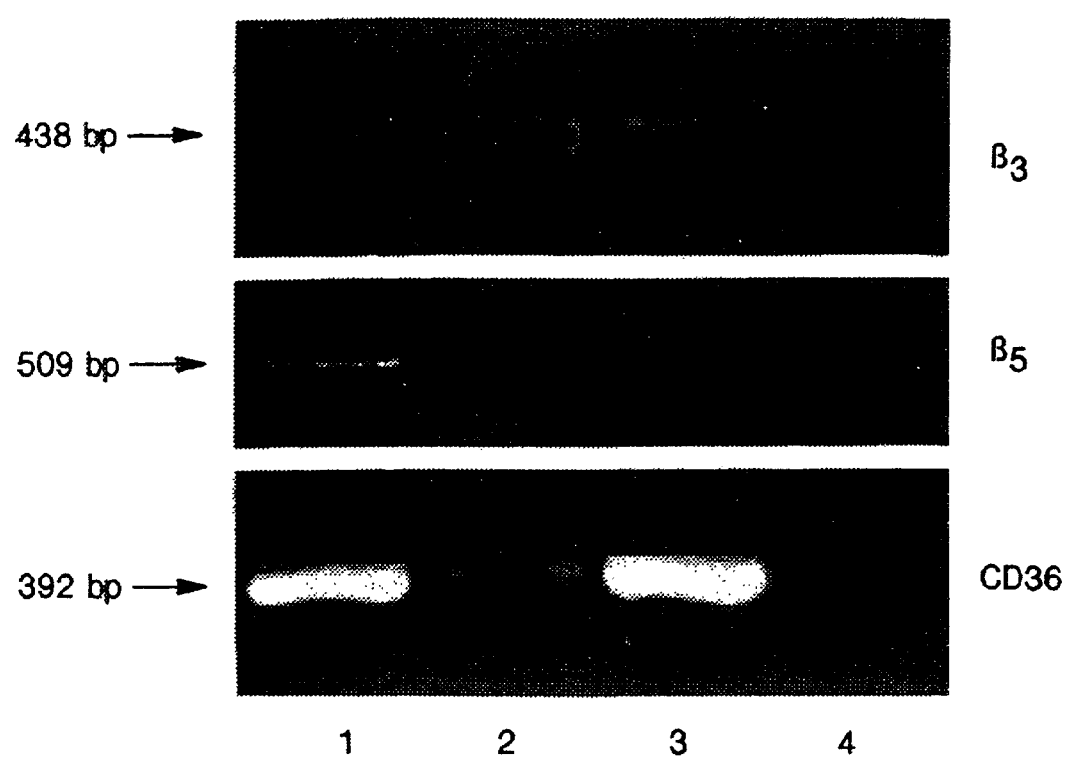

FIGS. 19A, 19B, and 19C: Protein and mRNA expression of $\alpha_v\beta_5$ and CD36 are down regulated during DC maturation.

Immature DCs [A] and mature DCs [B] were incubated with anti-$\alpha_v\beta_3$ [clone 23C6, Pharmingen], anti-CD36 [clone FA6, obtained from the Vth international workshop on leukocyte differentiation antigens], or anti-$\alpha_v\beta_5$ [clone P1F6, Chemicon], followed by PE-conjugated GAM-Ig [Biosciences]. All cells were analyzed by FACScan®. [C] RNA was purified from highly purified sorted cell populations of immature and mature DCs as previously described. RT-PCR was carried out and after 30 cycles of PCR the distinct bands for $\beta_3$, $\beta_5$ and CD36 could be seen in the immature DCs [lane 1]. In mature DCs only a faint band for CD36 and no band for $\beta_5$ could be visualized [lane 2] indicating minimal mRNA. In contrast, a band was evident for $\beta_3$ in the mature DCs. Note, the doublet for $\beta_3$ is an artifact in this particular exposure and does not indicate two unique bands [lane 2]. As a positive control, extracts from Bowes melanoma cells were run, which are known to express $\beta_3$ and CD36 (29) [lane 3]. As negative control, the Bowes melanoma cells were run in the absence of a reverse transcriptase [lane 4].

Figure 20A:
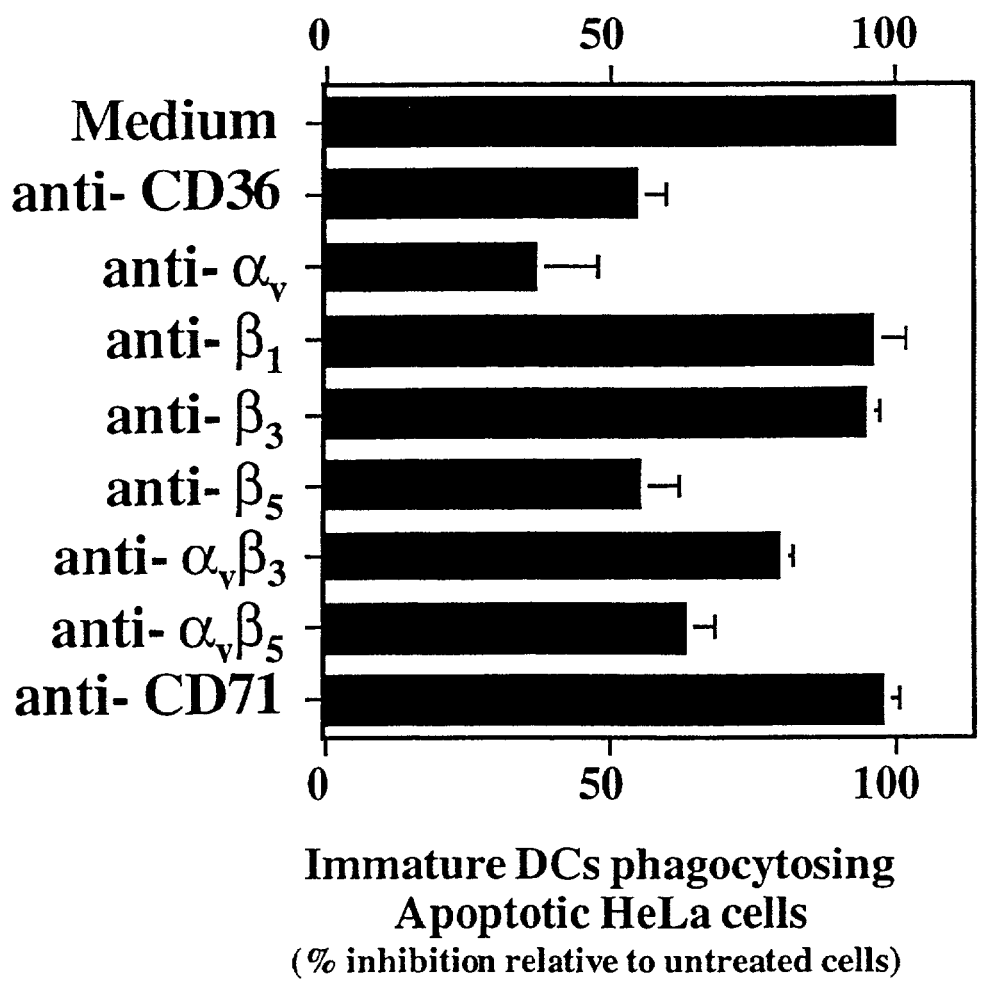

FIGS. 20A and 21B: Direct inhibition of phagocytosis by anti-$\alpha_v\beta_5$ and anti-CD36 antibodies.

HeLa cells were labeled with PKH26-GL, followed by irradiation using a 60UVB lamp [Derma Control Inc.], calibrated to provide 240 mJ cm$^{-2}$ in 2 minutes, sufficient for the induction of apoptosis. After 6–8 hours immature DCs dyed with PKH67-GL and pre-treated with 50 µg/ml of various monoclonal antibodies for 30 minutes were added to the wells containing apoptotic HeLa cells. 45–60 minutes later, cells were analyzed by FACS® for double positive cells. Phagocytic uptake is reported as a percentage of untreated cells. Maximal phagocytosis ranged from 44–52%. Results from three experiments were averaged and means plotted+SD. Similar results [data not shown] were obtained when apoptotic monocytes were used [A]. Immature DCs were incubated with red fluorescent latex beads at 37° C. [squares], 4° C. [diamonds], or at 37° C. in the presence of 50 µg/ml anti-$\alpha_v\beta_5$ [circles], anti-$\alpha_v$ [triangles]. The results shown indicate percent phagocytosis over background [B].

FIGS. 21A, 21B, 21C, 21D and 21E: DCs phagocytose apoptotic cells and necrotic cells. 293 cells were labeled red with the PKH26 GL fluorescent cell linker and induced to undergo apoptosis via UVB irradiation, or necrosis via repeated freezing and thawing. Immature DCs were dyed green with PKH 67-GL and then co-cultured with the apoptotic and necrotic cells for three hours at 4° or 37° C. at a ratio of 1:1. Cells were analysed by FACScan where double positive cells indicate uptake of the apoptotic and necrotic cells by the DCs. Dot blots are gated on the FL1 high positive cells [DCs] thus excluding the dead 293 cells from the analysis. [A] Green dyed DCs and red dyed apoptotic [293 UV] and necrotic [293 FT] cells alone. [B] Uptake of apoptotic and necrotic cells by immature DCs; [C] Uptake of apoptotic and necrotic cells by mature DCs. The results shown are representative of ten different experiments. [D] Uptake of FITC labeled beads and CD83 expression by immature DCs. [E] Uptake of FITC labeled beads by immature DCs which were then induced to mature via MCM.

FIGS. 22A, 22B, 22C, 22D, 22E and 22F: DCs exhibit a mature phenotype following exposure to necrotic but not apoptotic cells. [A] Apoptotic or necrotic BLCL were co-cultured with DCs at ratios of 1:2 or 1:5. After 48 hours, the DCs were stained extracellularly for CD83 and intracellularly for CD83 and DC-LAMP (27). [B,C] DCs were co-cultured with apoptotic or necrotic cells at a ratio of 1:2 for 48 hours and then stained extracellularly for CD83 and intracellularly for DC-LAMP. Values represent the averages of the geometric mean indices from three or more experiments. Arrowbars mark the standard deviation. Isotype matched antibodies served as controls in all experiments [data not shown]. [D] Immature and mature DCs were stained with monoclonal antibodies to CD83, CD86, CD40 and HLA-DR. Apoptotic or necrotic cell lines [E] or their respective supernatants [F] were added to immature DCs. After 48 hours the DC were stained with monoclonal antibodies to CD83, CD86, CD40 and HLA-DR. Values represent the averages of the geometric mean indices from three or more experiments. Arrowbars mark the standard deviation. Isotype matched antibodies served as controls in all experiments [data not shown].

Figure 23A:
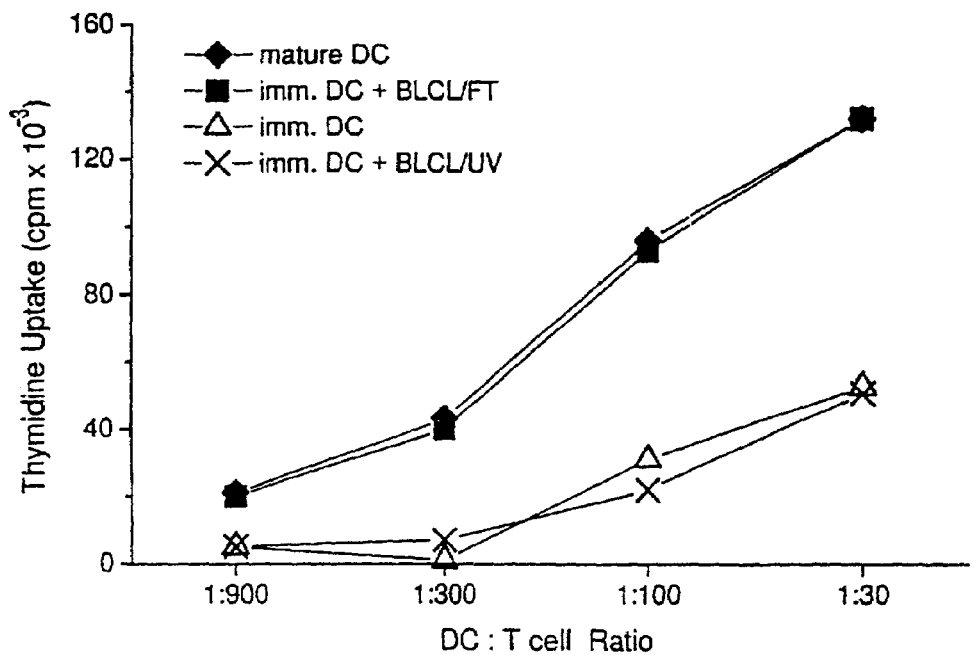
Figure 23B:
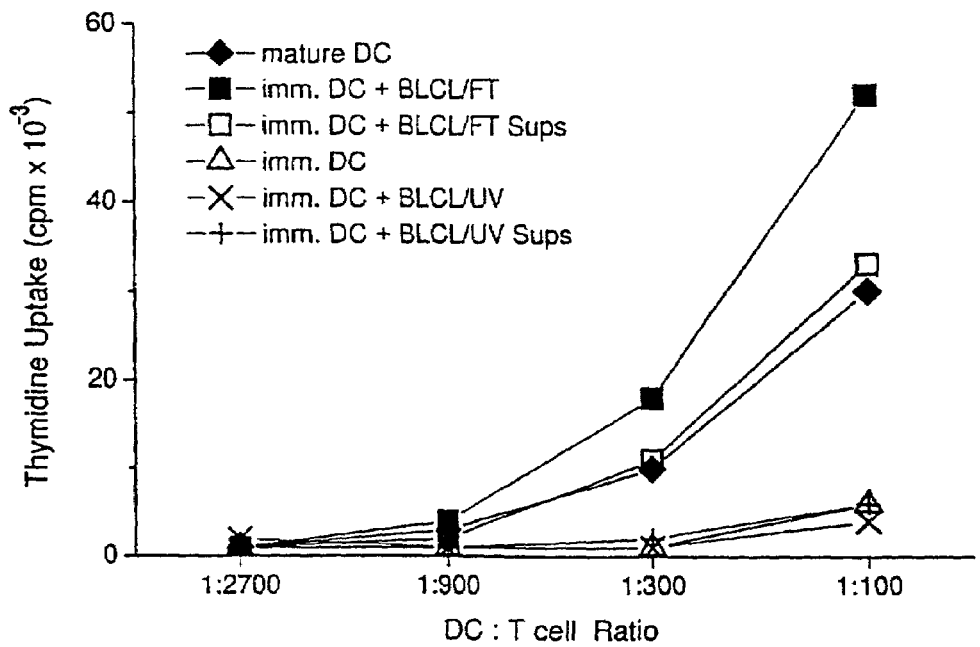

FIGS. 23A and 23B: DCs gain heightened T cell stimulatory capacity after exposure to necrotic but not apoptotic cells. Apoptotic or necrotic cell lines were added at various ratios to day 5 or 6 immature DCs. After 48 hours of co-culture, the DCs were assayed for their T cell stimulatory capacity. [A] DCs were irradiated with 3000 rad using a cesium irradiator [Ce 57] prior to addition to syngeneic T cells and 0.1 ng/ml SEA. After 3 days, 4 µci/ml $^3$H-Thymidine was added for 16 hours. [B] After coculture with apoptotic or necrotic cells, or their respective supernatants, DCs were fixed with 1% paraformaldehyde for 30 min at 4° C., washed extensively, and added in graded doses to 2×10$^5$ allogeneic T cells. After 4 days 4 uci/ml $^3$H-Thymidine was added for 16 hours. Immature and MCM matured DCs served as controls. Results are representative of three or more experiments and the values shown represent the mean of triplicate wells.

DETAILED DESCRIPTION OF THE INVENTION

This invention relates to methods of delivering antigens to dendritic cells for processing and presentation to T lymphocytes. In particular, this invention relates to the use of apoptotic cells for the packaging and delivery of exogenous antigen to the MHC class I presentation pathway of dendritic cells for stimulation or tolerization of class I-restricted CD8+ T cells. The apoptotic cell-activated dendritic cells and antigen-specific T cells produced according to the method of this invention may be used for various immunological interventions for the prevention and treatment of disease.

For the purpose of a more complete understanding of the invention, the following definitions are described herein:

The term "apoptosis" means non-necrotic cell death, which can occur under a variety of conditions including programmed cell death, exposure to ionizing and UV irradiation, activation of fas and other tumor necrosis factor receptor-related pathways, and drugs. Apoptosis is characterized by, inter alia, formation of "blebs" and vesicles at the plasma membrane, cell shrinkage, pyknosis, and increased endonuclease activity (20–21). Specific markers for apoptosis include, but are not limited to, annexin V staining, propidium iodide staining, DNA laddering, staining with dUTP and terminal transferase [TUNEL].

The term "apoptotic cell" means any cell expressing a native or foreign antigen undergoing apoptosis due to any condition, including those which ususally are associated with causing neurosis. Thus, an apoptotic cell is identified based on its characteristics described above rather than any method used leading to cell death. Similarly, the term "apoptotic cell fragments" means apoptotic cell material, bodies, blebs, vesicles, or particles other than whole apoptotic cells which contain antigen.

The term "necrosis" means a form of cell death resulting from irreversible trauma to cells typically caused by osmotic shock or exposure to chemical poison, and is characterized by marked swelling of the mitochondria and cytoplasm, followed by cell destruction and autolysis (22).

The term "donor cell" means the apoptotic cell that delivers antigen to dendritic cells for processing and presentation to T cells.

The phenomenon of "cross-priming" occurs when antigens from donor cells are acquired by the host APCs such as dendritic cells and are processed and presented on MHC molecules at the surface of the APC for activation of antigen-specific T cells.

The phenomenon of "cross-tolerance" occurs when antigens from donor cells are acquired by host dendritic cells and are presented under conditions that are non-inflammatory (lack of inflammation or other maturation stimuli) so as to cause antigen-specific unresponsiveness in T cells.

The term "antigen" means all, or parts thereof, of a protein or peptide capable of causing an immune response in a vertebrate preferrably a mammal. Such antigens are also reactive with antibodies from animals immunized with said protein. The potent accessory function of dendritic cells provides for an antigen presentation system for virtually any antigenic epitope which T lymphocytes are capable of recognizing through their specific receptors. Example 1, infra, demonstrates how dendritic cells can present viral antigen after acquisition from donor cells undergoing apoptosis, and effectively activate CTL responses.

Sources of Dendritic Cells

The dendritic cells used in this invention can be isolated as described herein or by methods known to those skilled in the art. In a preferred embodiment, human dendritic cells are used from an appropriate tissue source, preferably blood or bone marrow.

Mature dendritic cells can also be obtained by culturing proliferating or non-proliferating dendritic cell precursors in a culture medium containing factors which promote maturation of immature dendritic cells to mature dendritic cells. Steinman et al. U.S. Pat. No. 5,851,756 and U.S. applications application Ser. No. 08/600,483 (WO 97/29182) report methods and compositions for obtaining dendritic cells and are incorporated herein by reference.

The dendritic cell precursors, from which the immature dendritic cells for use in this invention are derived, are present in blood as PMBCs. Although most easily obtainable from blood, the precursor cells may also be obtained from any tissue in which they reside, including bone marrow and spleen tissue. When cultured in the presence of cytokines such as a combination of GM-CSF and IL-4 or IL-13 as described below, the non-proliferating precursor cells give rise to immature dendritic cells for use in this invention.

Culture of Pluripotential PMBCs to Produce Immature Dendritic Cells

Dendritic cell development can be divided into 4 stages: 1) a proliferating progenitor that can be either dendritic cell committed or uncommitted and capable of maturing to a nondendritic cell, 2) a non-proliferating precursor like the blood monocyte that does not show dendritic cell properties but is the starting population for many clinical studies, 3) an immature dendritic cell which has properties and commitment to become a dendritic cell, e.g. specialized antigen capture mechanisms including apoptotic cells for presentation, and MHC rich compartments, and 4) finally, the mature T cell stimulatory dendritic cell.

Cultures of immature dendritic cells, i.e. antigen-capturing phagocytic dendritic cells, may be obtained by culturing the non-proliferating precursor cells in the presence of cytokines which promote their differentiation. A combination of GM-CSF and IL-4 at a concentration of each at between about 200 to about 2000 U/ml, more preferably between about 500 and 1000 U/ml, and most preferably about 800 U/ml (GM-CSF) and 1000 U/ml (IL-4) produces significant quantities of the immature, i.e. antigen-capturing phagocytic dendritic cells, dendritic cells. Other cytokines or methods known in the art which efficiently generate immature dendritic cells may be used for purposes of this invention. Examples of other cytokines which promote differentiation of precursor cells into immature dendritic cells include, but are not limited to, IL-13. Maturation of dendritic cells requires the addition to the cell environment, preferably the culture medium,of a dendritic cell maturation factor which may be selected from monocyte conditioned medium and/or factors including TNF-$\alpha$, IL-6, IFN-$\alpha$, and IL-1-$\beta$. Alternatively, a mixture of necrotic cells or necrotic cell lysate may be added to induce maturation.

Co-culture of Dendritic Cells with Apoptotic Cells

Apoptotic cells may be used to deliver antigen to either immature or mature dendritic cells, either freshly isolated or obtained from in vitro culture. In a preferred embodiment, apoptotic cells comprising an antigen are co-cultured with immature dendritic cells for a time sufficient to allow the antigen to be internalized by the immature dendritic cells. These immature dendritic cells are then caused to mature by the addition of a maturation factor to the culture medium. The matured dendritic cells expressing processed antigen on their surface are then exposed to T cells for potent CTL induction.

In another embodiment, apoptotic cells may be used to deliver antigen to mature dendritic cells through surface receptors that enhance internalization of the apoptotic cells.

In another embodiment, apoptotic cells may be used to deliver antigen to immature dendritic cells that are maintained as immature dendritic cells as a means of efficiently modulating T cell tolerance or immunity in situ.

In a preferred embodiment, peripheral blood mononuclear cells [PBMCs] can be isolated from blood by sedimentation techniques. T cell-enriched [ER$^+$] and T cell-depleted [ER$^-$] populations can be prepared by resetting with neuraminidase treated sheep red blood cells. Dendritic cells are prepared from the ER$^-$ cells (Steinman et al. U.S. application Ser. No. 08/600,483) as discussed above and are preferably cultured for 7 days to 10 days in the presence of GM-CSF and IL-4. On about day 7 through 10, apoptotic cells can be co-cultured with the dendritic cells and the dendritic cells caused to mature over the next four days with the addition of monocyte conditioned medium, a signal for maturation.

Besides monocyte conditioned medium, a combination of cytokines may be used to induce maturation of the immature dendritic cells. Examples of cytokines which may be used alone or in combination with each other include, but are not limited to, TNF-α, IL-1β, IL-6, IFN-α and necrotic cells.

The apoptotic cell-activated dendritic cells made according to the method described above are the most efficient for induction of CTL responses. Delivery of antigen to mature dendritic cells, or alternatively, immature dendritic cells that are not caused to mature in vitro, is also within the scope of this invention.

The apoptotic cells useful for practicing the method of this invention should efficiently trigger antigen internalization by dendritic cells, and once internalized, facilitate translocation of the antigen to the appropriate antigen processing compartment.

In a preferred embodiment, the apoptotic cells, or fragments, blebs or bodies thereof, are internalized by the dendritic cells and targeted to an MHC class I processing compartment for activation of class I-restricted $CD8^+$ cytotoxic T cells.

In another embodiment, the apoptotic cells can be used to activate class II-restricted $CD4^+$ T helper cells by targeting antigen via the exogenous pathway and charging MHC class II molecules. Apoptotic cells, blebs and bodies are acquired by dendritic cells by phagocytosis. When a population of CD4+ cells is co-cultured with apoptotic cell-primed dendritic cells, the CD4+ T cells are activated by dendritic cells that have charged their MHC class II molecules with antigenic peptides. The apoptotic cell-charged dendritic cells of this invention activate antigen-specific CD4+ T cells with high efficiency.

For purposes of this invention, any cell type which expresses antigen and is capable of undergoing apoptosis can potentially serve as a donor cell for antigen delivery to the potent dendritic cell system. Examples of antigen that can be delivered to dendritic cells by donor cells include, but are not limited to, viral, bacterial, protozoan, microbial and tumor antigens as well as self-antigens. Preferred antigens for priming dendritic cells in vitro or in vivo are derived from influenza virus, malaria, HIV, EBV human papilloma virus (including both EBV-associated and EBV-unassociated lymphomas), CMV, renal cell carcinoma antigens, and melanoma antigens. In addition, self antigens that are targets of autoimmune responses can be delivered to dendritic cells e.g. insulin, histones, GAD.

For purposes of this invention the population of donor cells expressing antigen can be induced to undergo apoptosis in vitro or in vivo using a variety of methods known in the art including, but not limited to, viral infection, irradiation with ultraviolet light., gamma radiation, cytokines or by depriving donor cells of nutrients in the cell culture medium. Time course studies can establish incubation periods sufficient for optimal induction of apoptosis in a population of donor cells. For example, monocytes infected with influenza virus begin to express early markers for apoptotis by 6 hours after infection. Examples of specific markers for apoptosis include Annexin V, TUNEL+ cells, DNA laddering and uptake of propidium iodide.

Those skilled in the art will recognize that optimal timing for apoptosis will vary depending on the donor cells and the technique employed for inducing apoptosis. Cell death can be assayed by a variety of methods known in the art including, but not limited to, fluorescence staining of early markers for apoptosis, and determination of percent apoptotic cells by standard cell sorting techniques.

In one embodiment, donor cells are induced to undergo apoptosis by irradiation with ultraviolet light. Depending on the cell type, typically exposure to UV light (60 mjules/$cm^2$/sec) for 1 to 10 minutes induces apoptosis. This technique can be applied to any cell type, and may be most suitable for a wide range of therapeutic applications. The apoptotic donor cells expressing an antigen of interest on their surface could then be used to prime dendritic cells in vitro or in vivo.

In another embodiment, donor cells are induced to undergo apoptosis by administering a drug such as which induces apopotosis. This technique can also be applied to any cell type, and is also suitable for a wide range of therapeutic applications.

In another embodiment, donor cells are induced to undergo apoptosis by infection with influenza virus. These apoptotic cells which express viral antigens on their surface could then be used to prime dendritic cells in vitro or in vivo. The apoptotic cell-activated dendritic cells may then be used to activate potent influenza-specific T cells.

In another embodiment, tumor cells may be obtained and caused to undergo apoptosis. These apoptotic tumor cells, or tumor cell lines, could then be used to deliver tumor antigen to dendritic cells in vitro or in vivo. Once isolated, the tumor cells could be treated with collagenase or other enzymes which facilitate cell dissociation for culturing. The apoptotic cell-activated dendritic cells may then be used as cancer therapeutic agents by activating the immune system to specifically target the tumor cells.

In another embodiment of the invention, the donor cells can be transfected, transduced or transformed to express foreign antigens prior to induction of apoptosis. In this manner dendritic cells may be loaded with antigens not typically expressed on the donor cell. In addition, delivery of antigens via xenotransfer is also contemplated. These methods can be accomplished using standard techniques known in the art.

A variety of possible antigens can be used in this invention including, but not limited to, bacterial, parasitic, fungal, viral, and tumor antigens of cellular or viral origin. Preferred antigens include influenza virus, malaria, HIV, EBV, human papilloma virus, CMV, renal cell carcinoma antigens, and melanoma antigens. In addition, self antigens that are targets of autoimmune responses or other antigens for which it is desired to attenuate an immune response can be expressed on donor cells using any of the aforementioned methods.

Once donor cells expressing either native or foreign antigen have been induced to undergo apoptosis they can be contacted with an approprite number of dendritic cells in vitro or in vivo. The ratio of apoptotic cells to dendritic cells may be determined based on the methods disclosed in Example 1 or Example 6, infra. For most antigens a ratio of only about 1–10 donor cells to 100 immature dendritic cells is suitable for priming the dendritic cells. Higher numbers of apoptotic cells are preferred if mature dendritic cells are to be primed, preferably 100 to 1000 donor cells to mature dendritic cells.

The population of apoptotic cells should be exposed to the dendritic cells for a period of time sufficient for the dendritic cells to internalize the apoptotic cell, or apoptotic cell fragments. Efficiency of cross-priming or cross-tolerizing dendritic cells can be determined by assaying T cell cytolytic activity in vitro or using dendritic cells as targets of CTLs. Other methods known to those skilled in the art may be used to detect the presence of antigen on the dendritic cell surface following their exposure to apoptotic donor cells. Moreover, those skilled in the art will recognize that the length of time necessary for an antigen presenting cell to phagocytose apoptotic cells, or cell fragments, may vary depending on the cell types and antigens used.

An important feature of the dendritic cells of this invention is the capacity to efficiently present antigens on both MHC class I and class II molecules. Apoptotic donor cells, blebs, bodies or fragments thereof, are acquired by dendritic cells through the exogenous pathway by phagocytosis and as a result also efficiently charge MHC II molecules. CD4+ T cells may be activated by the dendritic cells presenting antigenic peptide which is complexed with MHC II using the method according to this invention, since it is known in the art that dendritic cells are the most potent inducers of CD4+ helper T cell immunity. CD4+ T cells can provide critical sources of help, both for generating active CD8+ and other killer T cells during the acute response to antigen, and for generating the memory that is required for long term resistance and vaccination. Thus, by using apoptotic cells to charge MHC class I and/or II products, efficient T cell modulation in situ can be achieved.

In a preferred embodiment both apoptotic and necrotic donor cells are used to prime dendritic cells. Preferably immature dendritic cells are contacted with the donor cells and both class I and II MHC receptors become optimally charged with antigen. In addition, the dendritic cells are matured by the presence of the necrotic cells which also contributes to MHC class II loading.

A novel aspect of this invention is the use of apoptotic cells to prime dendritic cells with antigen. An important advantage of the apoptotic cell system is that even poorly defined or undefined antigens can be routed to the appropriate antigen processing compartment of the dendritic cells to generate antigen-specific T cell responses. Moreover, dendritic cells can be charged with multiple antigens on multiple MHCs to yield poly or oligoclonal stimulation of T cells. Thus, since the starting material can be obtained from virtually any tissue, the only requirement for efficient targeting of potentially any antigen to dendritic cells is the packaging of the antigen with apoptotic cells or apoptotic cell material.

Accordingly, the scope of this invention includes an embodiment whereby the apoptotic cell delivery system is reconstituted in vitro using apoptotic cell fragments, or material thereof, including, but not limit to, proteins, phospholipids, carbohydrates and/or glycolipids, which enhance internalization and translocation of antigen to the appropriate antigen processing compartment in the dendritic cells. Thus, it is contemplated that liposomes comprising at least antigen and any combination of the aforementioned apoptotic cell fragments, or materials thereof, may enhance delivery of antigen to dendritic cells. Liposomes enhanced with apoptotic cell fragments, or materials thereof in accordance with this invention, can also be used for delivering antigen in vivo to dendritic cells.

As stated above, to prepare the liposomes it is desirable to include ligands for various receptors on the dendritic cells including various integrin receptors, CD36 and heat shock proteins. It is also contemplated that various mutant forms or fragments containing binding domains of such proteins may also be used. If DC are pulsed with liposomes in vitro, between 0.1–1000 ng of antigen is preferred for priming between $1 \times 10^5$ and 5 million DCs. Higher amounts of antigen in liposomes are used to deliver between about 10 ng to 10 μg per immunization if DCs are to be pulsed in vivo.

In another embodiment, the apoptotic cell antigen delivery system can be used as a method for identifying and isolating poorly characterized antigens. For example, a population of tumor cells can be induced to undergo apoptosis, the apoptotic tumor cells can then be co-cultured with dendritic cells for a time sufficient to allow relevant immunogenic peptides to be processed and presented on the dendritic cell surface. The immunogenic peptides can then be eluted from the MHC and other presenting molecules of dendritic cell surface as disclosed in U.S. Pat. No. 5,851,756 and purified using standard protein purification techniques known in the art including, but not limited to, HPLC and mass spectrophotometry.

Activation of Dendritic Cells and CTLs

In yet another embodiment of this invention, the apoptotic cell-charged dendritic cells or the antigen-specific T lymphocytes generated by methods described herein may be used for either a prophylactic or therapeutic purpose. For activating T cells in an individual between about $2 \times 10^5$ and $2 \times 10^9$ more preferably between 1 million and 10 million apoptotic cell-activated mature dendritic cells should be administered to an individual. The dendritic cells should be administered in a physiologically compatible carrier which is nontoxic to the cells and the individual. Such a carrier may be the growth medium described above, or any suitable buffering medium such as phosphate buffered saline (PBS). The mature dendritic cells prepared according to this invention are particularly potent at activating T cells. For example, using prior methods of dendritic cells the ratio of dendritic cells to T cells necessary for strong T cell activation is about 1 dendritic cell to 30 T cells whereas the ratio according to this invention is about 1 T cell to 1000 dendritic cells. Thus, fewer dendritic cells are required. For activating T cells in vitro the ratio of dendritic cells to T cells is between 1:10 and 1:1000. More preferably, between 1:30 and 1:150. Between approximately $10^6$ and $10^9$ or more activated T cells are administered back to the individual to produce a response against the antigen.

Dendritic cells may be administered to an individual using standard methods including intravenous, intraperitoneal, subcutaneously, intradermally or intramuscularly. The homing ability of the dendritic cells facilitates their ability to find T cells and cause their activation.

By adapting the system described herein, dendritic cells could also be used for generating large numbers of CD8$^+$ CTL, for adoptive transfer to immunosuppressed individuals who are unable to mount normal immune responses. Immunotherapy with CD8$^+$ CTL has been shown to amplify the immune response. Bone marrow transplant recipients given CMV specific CTL by adoptive transfer, do not develop disease or viremia (4). These novel approaches for vaccine design and prophylaxis should be applicable to several situations where CD8$^+$ CTLs are believed to play a therapeutic role e.g. HIV infection (1–3), malaria (5) and malignancies such as melanoma (8–9).

Examples of diseases that may be treated by the methods disclosed herein include, but are not limited to bacterial infections, protozoan, such as malaria, listeriosis, microbial infections, viral infections such as HIV or influenza, cancers or malignancies such as melanoma, autoimmune diseases such as psoriasis and ankolysing spondylitis.

By adapting the system described herein, dendritic cells could also be used for inducing tolerance. Dendritic cells expressing fas-L for example can kill fas expressing activated T cells (23). Thus, it may be possible to deliver fas-L bearing dendritic cells that are pulsed with apoptotic cells or blebs or bodies containing autoantigens to delete autoreactive T cells in vivo; or alternatively, one can target dendritic cells that are specialized to induce tolerance rather than immunity, as proposed for the subset of dendritic cells known as "lymphoid dendritic cells" (see Steinman et al., Immunol. Rev. 156: 25–37, 1997).

Methods for Assessing Cytotoxic T Cell Activity

Frequently, in clinical disease it is difficult to detect killer cells because of inadequate presentation. This invention also provides methods for assessing the cytotoxic activity of T lymphocytes, and in particular the ability of cytotoxic T lymphocytes to be induced by antigen presenting dendritic cells. According to this method, a sample comprising T lymphocytes to be assayed for cytotoxic activity is obtained. Preferably, the cells are obtained from an individual from whom it is desirable to assess their capacity to provoke a cytotoxic T lymphocyte response. The T lymphocytes are then exposed to antigen presenting dendritic cells which have been caused to present antigen. Preferably, the dendritic cells have been primed with apoptotic cells which express antigen. After an appropriate period of time, which may be determined by assessing the cytotoxic activity of a control population of T lymphocytes which are known to be capable of being induced to become cytotoxic cells, the T lymphocytes to be assessed are tested for cytotoxic activity in a standard cytotoxic assay. Such assays may include, but are not limited to, the chromium release assay described herein.

The method of assessing cytotoxic T lymphocyte activity is particularly useful for evaluating an individual's capacity to generate a cytotoxic response against cells expressing tumor or viral antigens. Accordingly, this method may be useful for evaluating an individual's ability to defend against cancers, for example melanoma, or viruses. In addition, this method is useful to detect autoreactive killer cells and could monitor not only the presence of killer cells, but their response to therapy.

All books, articles, or patents referenced herein are incorporated by reference in their entirety.

EXAMPLE 1

Use of Apoptotic Cells to Deliver Antigen to Dendritic Cells and Induce Class I-Restricted CTLs Materials & Methods Generation of mononuclear subsets. Peripheral blood mononuclear cells [PBMCs] were isolated from blood by sedimentation in Ficoll-Hypaque [Pharmacia Biotech]. T cell-enriched [ER$^+$] and T cell-depleted [ER$^-$] populations were prepared by resetting with neuraminidase treated sheep red blood cells, as previously described (37). T cells were purified from ER$^+$ cells by removal of monocytes, NK cells and MHC class II$^+$ cells (37). Monocytes were obtained from ER$^-$ cells by plastic adherence. Dendritic cells were prepared from ER$^-$ cells cultured for 7 days in the presence of GM-CSF and IL-4, followed by 4 days in monocyte conditioned medium (42, 43).

Induction and detection of apoptosis. Monocytes were infected with influenza virus in serum free RPMI. Initial time course studies established that after 5 hours, monocytes began to express early markers for apoptosis and that by 10–12 hours, a majority of the cells had been induced to undergo apoptosis. Cell death or Apoptosis was assayed using the Early Apoptosis Detection Kit [Kayima Biomedical]. Briefly, cells are stained with Annexin V-FITC [Ann-V] and Propidium Iodide [PI]. Early apoptosis is defined by Ann V$^+$/PI$^-$ staining as determined by FACScan® [Becton Dickinson]. 293 cells were triggered to undergo apoptosis using a 60UVB lamp [Derma Control, Inc.], calibrated to provide 2 mJ/cm$^2$/sec at a distance of 8 cm for 10 mins.

Co-culture of DCs with Apoptotic Cells. Monocytes from HLA-A2.1$^-$ individuals were infected with influenza virus. Live influenza virus [Spafas, Inc.] was added at a final concentration of 250 HAU/ml [MOI of 0.5] and incubated for 1 hour at 37° C. (37). Heat-inactivated virus was prepared by incubating virus for 30 minutes at 56° C. (39). Cells were washed with serum-containing medium and added to 24 well plates at varying cell doses. After 1 hour, contaminating non-adherent cells were removed and fresh medium was added. Following a 10 hour incubation at 37° C., 3.3×10$^3$ uninfected DCs and 1×10$^6$ T cells were added to the wells.

Assay for Virus-Specific CTLs. After 7 days of culture, T cells were assayed for cytolytic activity using conventional Na$^{51}$CrO$_4$ release assay (37). The targets were either influenza-infected syngeneic monocytes or T2 cells [a TAP$^{-/-}$, HLA-A2.1$^+$, class II$^-$ cell line] pulsed for 1 hour with 1 uM of the immunodominant influenza matrix peptide, GILG-FVFTL (59,60). Specific lysis was determined by subtracting the percent cytotoxicity of uninfected monocytes or unpulsed T2 cells. Additionally, syngeneic DCs were used as targets where noted. In such cases, direct percent cytotoxicity is reported.

Reagents. The Z-VAD-CHO [Kayima Biomedical] was added to monocytes for 1 hour prior to infection and subsequently washed out. DCs were cultured for 1 hour in Brefeldin A (BFA) [Sigma] or NH$_4$Cl [Sigma] and then maintained in these inhibitors for the course of the assay.

Results

Influenza A virus establishes a nontoxic infection in human DCs (37,38, 2016–4008). Once infected, these DCs are capable of eliciting virus-specific recall CTL responses within 7 days. The CTLs generated are class I-restricted and kill virus-infected monocytes and peptide pulsed target cells (37,39). Compared with DCs, influenza infected monocytes are poor stimulators of CTL responses (37) and undergo apoptosis (40,41). We have exploited these observations to investigate the role of apoptosis in the generation of antigen which could be acquired by uninfected DCs.

DCs were prepared from peripheral blood precursors of HLA-A2.1$^+$ individuals (42,43). Uninfected DCs and syngeneic T cells were co-cultured with influenza-infected syngeneic [FIG. 1a] or allogeneic [FIG. 1b] monocytes for 7 days. Influenza-specific CTLs were generated in these co-cultures, suggesting that the DCs acquired antigen from the monocytes. The DCs and not the infected monocytes functioned as the APC, since the latter failed to stimulate CTLs in the absence of DCs, even at a stimulator:responder ratio of 1:2 [FIG. 1a, dashed lines]. The CTL responses generated in these co-cultures were as potent as those induced by influenza-infected DCs. In some experiments, as few as 5×10$^3$ infected monocytes were sufficient to charge uninfected DCs for the induction of robust CTLs [FIG. 1b]. Co-culturing influenza-infected HeLa cells with uninfected DCs also induced potent influenza-specific CTLs [data not shown]. The CTLs generated were capable of lysing influenza-infected syngeneic macrophage targets [FIG. 1a] as well as matrix peptide-pulsed HLA-A2.1+ T2 cells [FIG. 1b].

To confirm that antigen is transferred to, and expressed directly by, DC MHC class I products, we co-cultured uninfected DCs and influenza-infected monocytes, and used the DCs as targets for CTLs [FIG. 1c]. DCs co-cultured with infected monocytes were as efficient as virus-infected DCs at presenting antigen. These results suggest that influenza antigen from infected monocytes gained access to MHC class I of the DC, i.e. antigen from HLA mismatched monocytes were 'cross-priming' T cells via the DC.

Given the nature of the antigen, it was important to exclude live virus as the agent responsible for the transfer of antigen to DCs. Based on previous studies (14,20), influenza-infected monocytes produce only low levels of infectious virus before they undergo apoptosis. Infection of $5\times10^4$ monocytes with an MOI of 2.0 would be expected to yield up to $1\times10^3$ infectious virions after a 24 hour culture period. To prevent infection of DCs by monocyte produced virus, all experiments were done in human serum. The presence of blocking anti-hemagglutinin antibodies prevents influenza virions from binding to cell surface glycoconjugates. Indeed, the addition of influenza virus [highest dose, $10^4$ infectious virions] directly into cultures containing uninfected DCs and T cells did not generate a CTL response [data not shown]. To further exclude the possibility that monocytes were releasing virus during the 7 day co-culture, we tested for the presence of free virions using a standard hemagglutination assay with chicken RBC (45). Less than 1 HAU/ml [hemagglutination units per milliliter] was detected in the medium at 12 hr, 24 hr and 7 days of co-culture.

We also exclude the possibility that the CTL responses were due to free peptide being released by the dying monocytes, thereby charging class I molecules on DCs. Media from wells containing the infected monocytes were collected after an overnight culture and transferred to fresh wells containing T cells and uninfected DCs. Virus-specific CTLs were generated after a 7 day culture period [FIG. 2a, 10 hr transfer]. However, this CTL activity was abrogated if the medium was passed through a filter [0.45 um pore size] prior to being added to T cell-DC cultures [FIG. 2a, filter], suggesting that the antigenic material was neither live virus nor free peptide, as both would have passed through the filter. This was confirmed by sedimentation experiments [FIG. 2b]. Media from wells containing the infected monocytes were removed and spun at 250×g. The antigenic material could be localized in the pellet [FIG. 2b, down arrow], but not in the supernatant fraction [FIG. 2b, up arrow]. Notably, the pelleted material fully accounted for the CTL activity generated in direct transfer [FIG. 2b, stars]. Hemagglutination activity could not be detected in the pelleted material, confirming that influenza virions were not trapped in this fraction. Furthermore, when the medium from infected monocyte cultures was pulsed onto T2 cells, they could not be targeted by influenza-specific CTLs [data not shown]. Collectively, these results are most consistent with the source of antigen being fragmented or intact apoptotic cells.

The role of apoptosis in the transfer of antigen to the uninfected DC was therefore assessed. We first show that influenza-infected monocytes undergo apoptosis as detected by annexin V binding, an early marker for programmed cell death [FIG. 3a]. In contrast, heat-inactivated influenza virus, which reliably reduces viral replication, failed to induce apoptosis in monocytes [FIG. 3a]. However, DCs that are infected with heat-inactivated virus remain capable of stimulating potent influenza-specific CTL responses. We employed this replication deficient virus to probe the requirement for apoptosis in cross-priming. When media from wells containing the heat-inactivated influenza-infected monocytes were collected after an overnight culture and transferred to fresh wells containing T cells and uninfected DCs, no influenza-specific CTLs were generated [FIG. 3b, 10 hr transfer, HI virus]. In contrast, DCs exposed to medium derived from live virus-infected monocytes, which contained apoptotic cells, did elicit a CTL response [FIG. 3b, 10 hr transfer, live virus]. However, if the heat-inactivated influenza-infected monocytes were allowed to undergo apoptosis spontaneously, as occurs during 7 days of culture (46), antigenic material was generated and virus-specific CTLs were induced [FIG. 3b, co-culture, HI virus]. This data also argues against the possibility that live virus within the apoptotic cell is responsible for the transfer of antigenic material to the DCs.

To establish that apoptosis is the trigger for cross-priming, we first used Z-VAD-CHO, irreversible peptide inhibitor of caspase activity [Kamiya Biomedical Company]. It was possible to block apoptosis of influenza-infected monocytes [determined by TUNEL], without affecting the expression of viral proteins, [evaluated by staining with anti-nucleoprotein antibodies, data not shown]. Influenza-infected monocytes were cultured overnight in the presence of varying concentrations of Z-VAD. The medium from these wells were then added to fresh wells containing T cells and uninfected DCs. After 7 days, the responding T cells were measured for their influenza-specific cytolytic activity. At concentrations of Z-VAD which inhibited apoptosis of the infected monocytes, antigenic material was not transferred to the uninfected DCs and virus-specific CTLs were not generated [FIG. 3c].

We next compared apoptotic death to necrotic death for the generation of antigenic material. Influenza-infected 293 cells were used for this experiment. Greater than 95% of the cells expressed influenza proteins after 10 hours, but unlike monocytes, apoptosis was not triggered. Apoptosis was induced in the 293 cells by exposure to 60 mJ/cm$^2$ UVB irradiation (47), and necrosis was achieved by incubation in a hypotonic solution for 30 minutes at 37° C. Apoptotic or necrotic cells were co-cultured with uninfected DCs and T cells for 7 days and responding T cells were tested as described above. Only apoptotic but not necrotic cells were capable of transferring antigen to the DCs, as determined by the generation of a potent influenza-specific CTL response [FIG. 3d]. Similar findings were made when apoptotic versus necrotic influenza-infected monocytes were used as the source of antigen [data not shown].

The cellular requirements for generating CTLs via this pathway were also investigated. Given that lysis of T2 cells, an HLA-A2.1+ cell line, was dependent on the matrix peptide, which is specific for HLA-A2.1, it was expected that the effectors were MHC class I-restricted [FIG. 1b]. Indeed, when CD4+ and CD8+ subpopulations were purified at the end of the 7 day culture period, CTL activity was detected only in the CD8+ fraction [data not shown].

We next examined whether co-cultures of uninfected DCs, influenza-infected monocytes and purified CD8+ T cells could generate CTLs [FIG. 4a]. Purified CD8+ cells did not develop into potent CTLs in 3 separate experiments even when exposed to high doses of influenza-infected monocytes. The addition of CD4+ T cells, but not human IL-2, restored the ability to generate influenza-specific CTLs. Thus, CD8+ T cells require CD4+ T cell help during the induction phase in this exogenous pathway, but once generated they are the sole effectors. Notably, DCs directly infected with influenza virus stimulate robust CTL responses from purified CD8+ T cells, independent of CD4+ T cell help or exogenous cytokines at stimulator:responder ratios as low as 1:100 (37). The requirement for CD4+ T cells in this exogenous pathway distinguishes it from the endogenous class I pathway. This observation is consistent with recent findings where CTL induction by cross-priming in vivo was shown to require CD4+ T cell help, by direct action on the APC (24).

DCs and macrophages were compared as potential mediators of this exogenous pathway for class I MHC presentation. Uninfected HLA-A2.1+ DCs or macrophages, and syngeneic T cells were co-cultured with infected HLA-A2.1− monocytes. After 7 days, the responding T cells were measured for their influenza-specific cytolytic activity. DCs, but not macrophages, were capable of stimulating influenza-specific CTLs [FIG. 4b]. In fact, as increasing doses of syngeneic uninfected macrophages were introduced into co-cultures containing uninfected DCs, T cells and infected allogeneic monocytes, the CTL activity was abrogated [FIG. 4b]. Presumably, the macrophages act to sequester antigen from the DCs by efficiently engulfing the apoptotic cells.

Different pathways have been proposed for the presentation of exogenous antigen on MHC class I molecules. One possibility is that the antigens access the cytoplasm directly from the endosomal compartments and enter the 'classical' class I processing pathway (26,29). Alternatively, class I molecules associated with invariant chain may enter the endosomes (49). Finally, peptides generated in the endosomes may be regurgitated to the cell surface, charging class I molecules (34). We investigated if intracellular processing was required for DCs to present antigens from apoptotic cells. Uninfected DCs pulsed with influenza-infected allogeneic monocytes were used as targets for influenza specific CTLs [Table I]. A 3–9 hr co-culture of uninfected DCs and infected apoptotic monocytes was sufficient to charge DCs with antigen. The DCs were preincubated with 10 mM ammonium chloride, which neutralizes the endocytic compartment, or 6 ug/ml Brefeldin A [BFA], an inhibitor of vesicular transport (50). Both ammonium chloride and BFA completely inhibited the DCs ability to present antigenic material on MHC class I. Lactacystin, an irreversible inhibitor of the 26S proteasome (51), only partially blocked antigen presentation by the uninfected DCs [unpublished data]. The data suggest that both classical and non-classical class I pathways are utilized for the presentation of exogenous antigen derived from apoptotic cells.

Figure 5A:
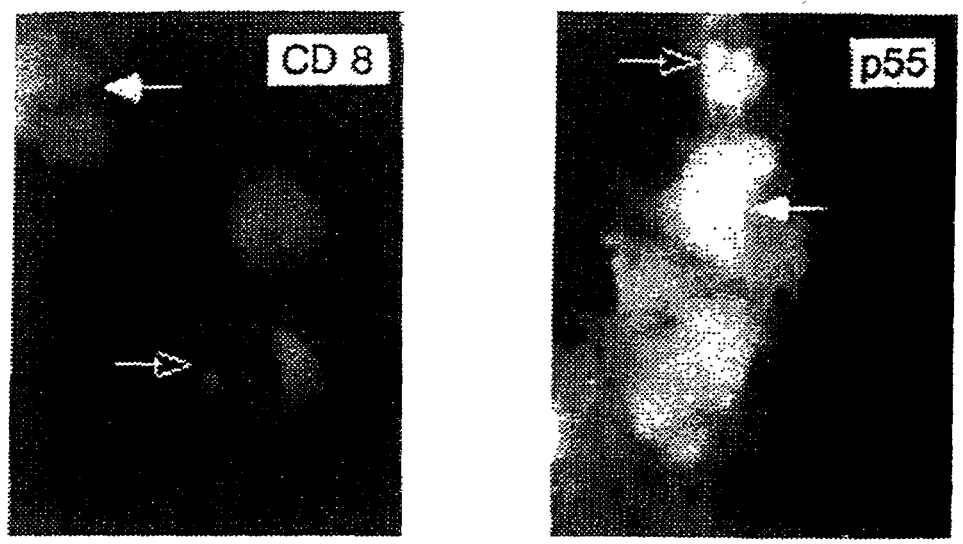
FIGS. 5a, 5b and 5c: Dendritic cells engulf apoptotic monocytes. Influenza-infected monocytes and uninfected DCs were co-cultured for up to 10 hours.
Figure 5B:
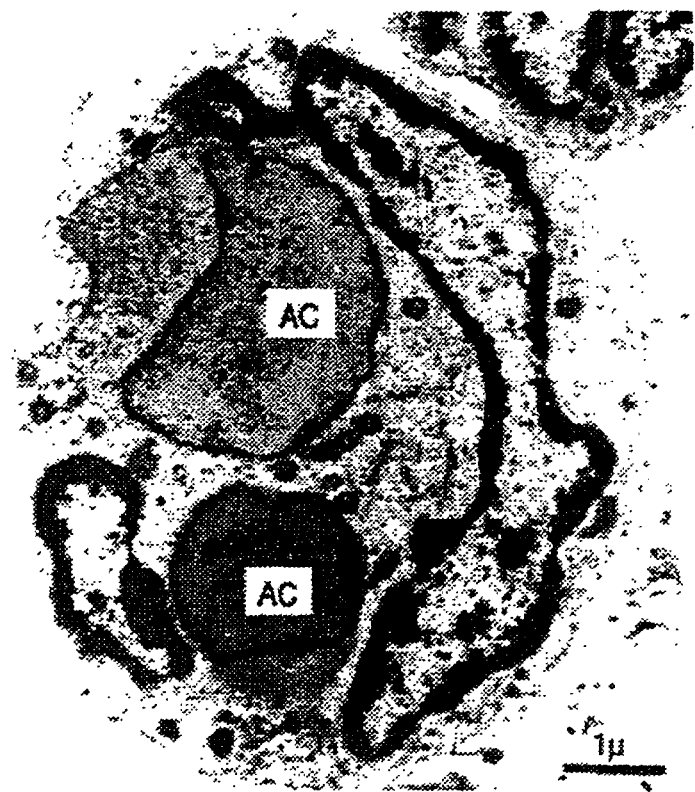
Figure 5C:

Since processing was required for presentation of monocyte derived antigen, immunofluorescence and electron microscopy were used to document that DCs phagocytosed apoptotic cells. By immunofluorescence, we observed phagocytosis of fragmented or intact cell bodies in 10–20% of the DCs [FIG. 5a]. DCs were identified by the DC-restricted marker, p55, and apoptotic material was identified by intense DAPI staining of pyknotic nuclei. This was confirmed by electron and immuno-electron microscopy [FIG. 5b,c]. Within the cytoplasm of 20–25% of the DCs, identified by expression of CD83 [FIG. 5c, inset 1], we observed apoptotic cells with an apparently intact plasma membrane [inset 2]. We believe these images represent the method by which DCs acquire apoptotic cells. These results are consistent with a recent report where it was reported that DCs associate with apoptotic cells via the vitronectin receptor αvβ3, but fail to associate with opsonized particles and necrotic cells (52).

Previous studies have shown that murine DCs have the capacity to present soluble antigens via an exogenous pathway, leading to the induction of MHC class I-restricted CTLs (32, 53–55). In addition, a single report reported that following intra-venous injection of allogeneic cells, rat interdigitating DCs within lymphnodes were found to contain whole cells and cell fragments (56). Using virus-infected monocytes, which themselves do not induce CTLs, we show that human DCs can acquire physiologically relevant antigens by phagocytosing apoptotic cells and then stimulating MHC class I-restricted CTLs.

EXAMPLE 2

Apoptotic Transfected 293 Cells Serve as Antigenic Material for 'Cross-Priming' of CD8+ T Cells The methods and materials unless otherwise specified were the same as in Example 1.

Figure 6:
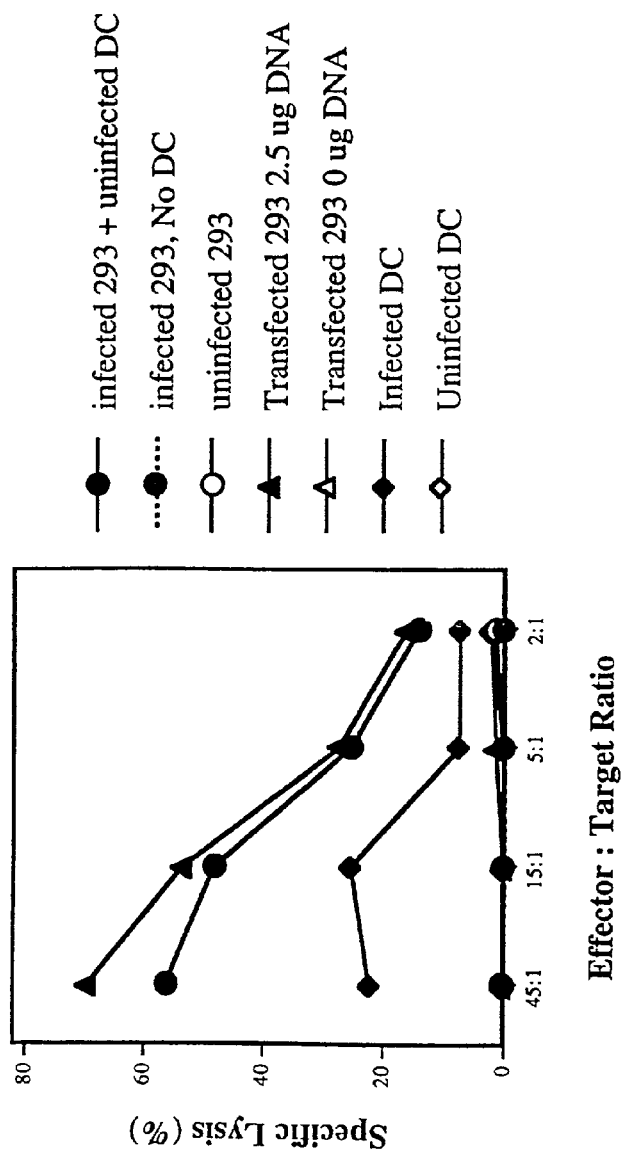
FIG. 6: Apoptotic transfected 293 cells serve as antigenic material for 'cross-priming' of CD8$^+$ T cells.

The following methods were used to carry out the experiments shown in FIG. 6. 293 cells, a human kidney epithelial cell line, were transfected with a construct encoding the matrix gene from Influenza A (filled triangles). After 2 days in culture, $1\times10^4$ transfected 293 cells were added to fresh wells and were UV-B irradiated in order to induce apoptotic death. DCs and T cells were then added to these wells and after 7 days, responding T cells were assayed for influenza-specific cytolytic activity using matrix peptide pulsed T2 cells as targets.

Results

The results demonstrate that a transfected tumor cell line can serve as a donor apoptotic cell, allowing for the transfer of antigen to the uninfected dendritic cell and the effective induction of antigen-specific CD8+ CTLs. Controls included: mock transfected cells (open triangles) infected and uninfected 293 cells (filled and open circles, respectively), infected 293 cells without DCs (filled circles, dotted line), infected and uninfected DCs (filled and open diamonds, respectively).

EXAMPLE 3

Figure 7:
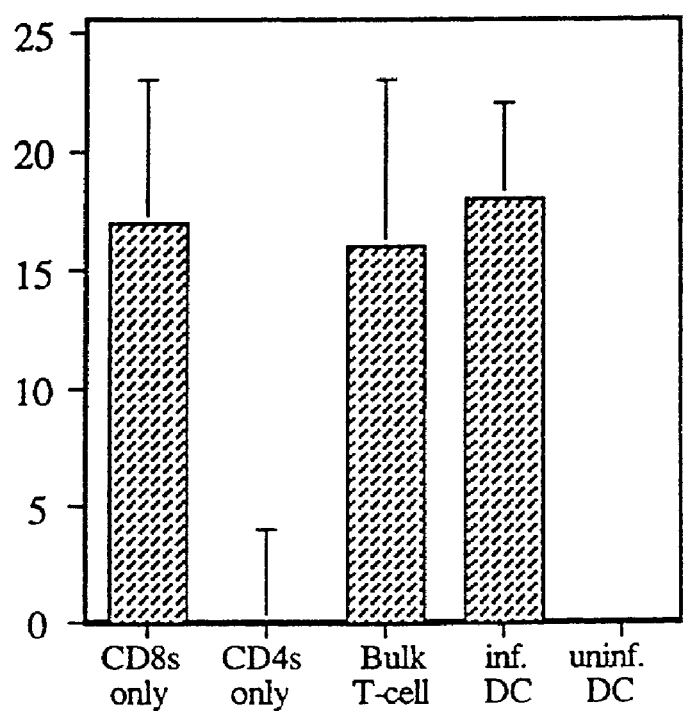
FIG. 7: CD8$^+$ T-cells and not CD4$^+$ cells are responsible for influenza-specific cytotoxicity.

CD8+ T-Cells and not CD4+ Cells are Responsible for Infuenza-specific Cytotoxicity The following methods were used to carry out the experiments shown in FIG. 7. Generation of CD8+ CTLs requires CD4+ T-cell help. Purification of CD8+ and CD4+ T cells after CTL induction, established that CD8+ cells were responsible for the influenza-specific cytolytic activity. Influenza infected allogeneic monocytes were co-cultured with DCs and T-cells. After 7 days, subpopulations of T cells were purified and tested for cytolytic activity (37). Effector: Target ratio=15:1.

Results

Given that the lysis of T2 cells, an HLA-A2.1+ cell line, was dependent on the matrix peptide, which is specific for HLA-A2.1, it was expected that the effectors were MHC class I-restricted (see Example 1). To confirm this, highly purified CD4+ and CD8+ subpopulations were isolated at the end of a 7 day culture period. As demonstrated in FIG. 7, CTL activity was detected only in the CD8+ fraction.

EXAMPLE 4

Figure 8:
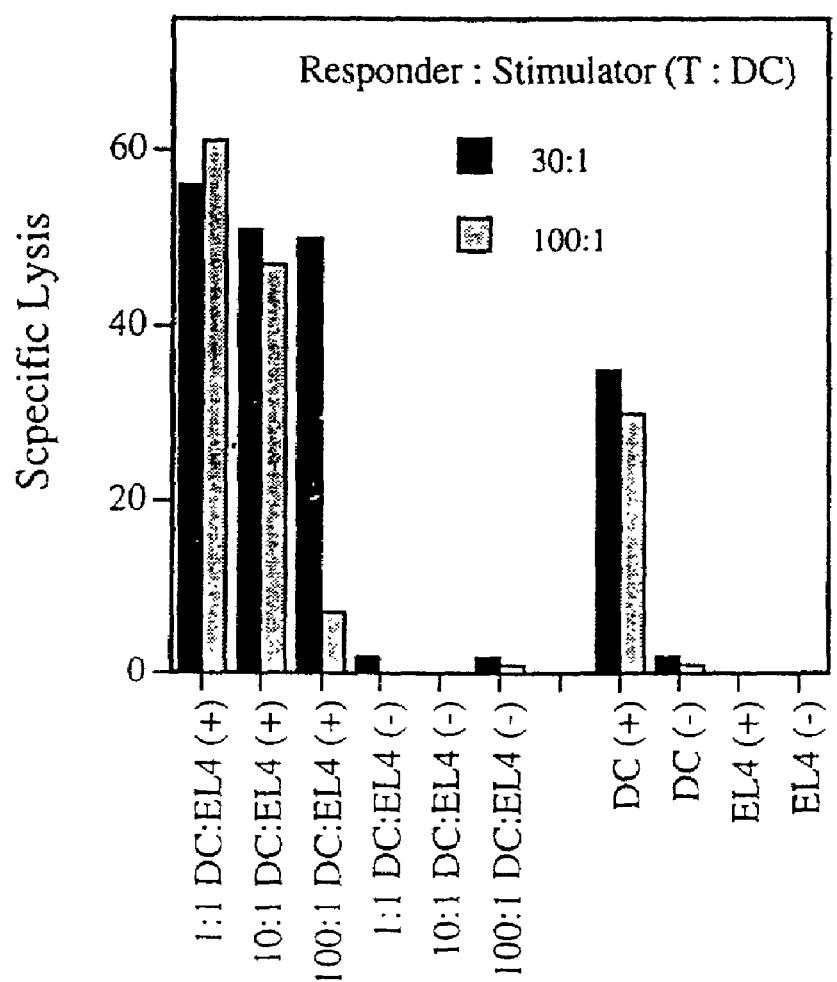
FIG. 8: Immature DCs phagocytose Influenza Infected EL4 cells and stimulate Influenza-specific CTLs.

Immature DCs Phagocytose Influenza Infected EL4 Cells and Stimulate Influenza-specific CTLs The following methods were used to carry out the experiments shown in FIG. 8. Immature DCs were pulsed vith various concentrations of UV irradiated influenza infected EL4 cells in the presence of monocyte conditioned media (a maturation signal for the DCs). After three days, the DCs were collected and cultured with 2×105 syngeneic T cells at responder:stimulator ratios of 30:1 and 100:1 in a 96-well microtiter plate. After 7 days in culture, responding T cells were tested in a standard 51Cr release assay using T2 target cells pulsed with the immunodominant epitope of influenza matrix protein. Controls included the use of UV irradiated uninfected EL4 cells as a source of apoptotic food. Influenza infected DCs and EL4s served as positive and negative controls, respectively. Effector:target ratio was approximately 25:1.

Results

Immature DCs pulsed with apoptotic influenza infected EL4 cells in the context of monocyte conditioned media, were used to stimulate bulk T cells. The immature DCs efficiently engulf the murine tumor cell line and are able to cross-present influenza antigen derived from those apoptotic cells. Indeed, at a ratio of DCs:EL4s equal to 100:1, it was still possible to elicit potent T cells responses. This experiment also demonstrates the possibility of using xenotropic cells as a source of antigen bearing apoptotic cells for the delivery of antigenic material to the DCs.

EXAMPLE 5

Figure 9A:
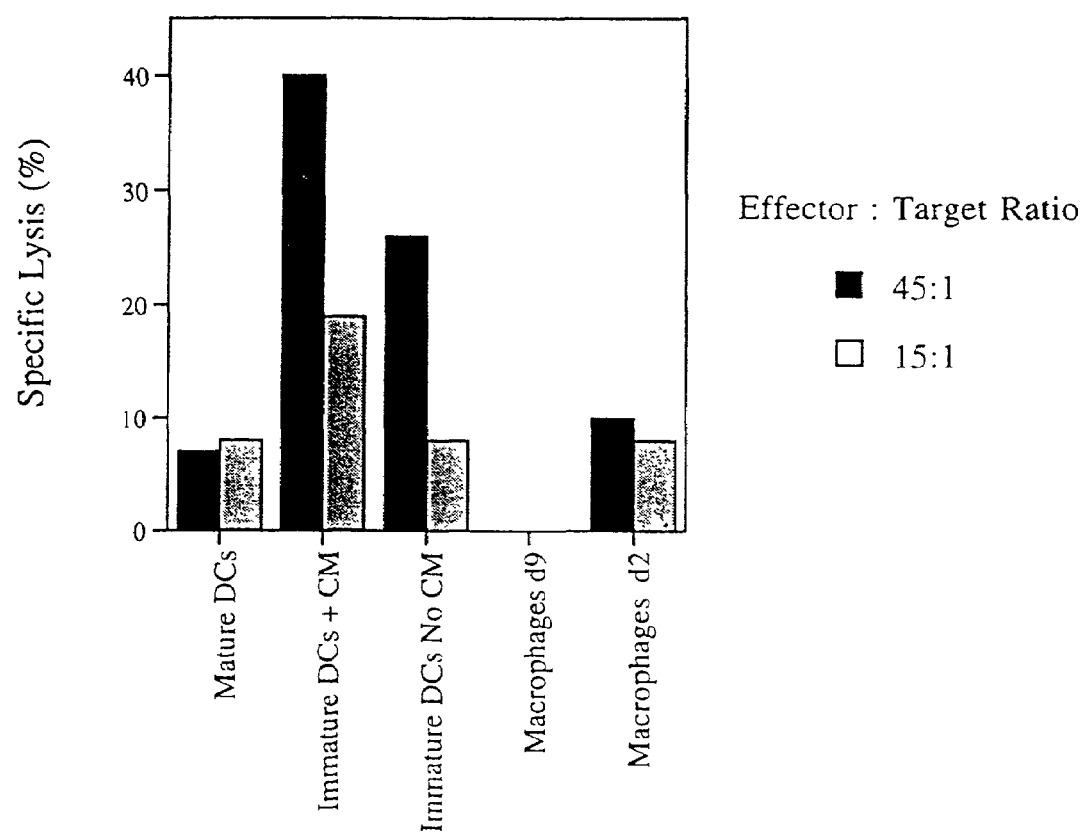
FIGS. 9A and 9B: Immature DCs, but not mature DCs or macrophages cross-present antigenic material from apoptotic cells and become targets of antigen-specific CTLs.
Figure 9B:
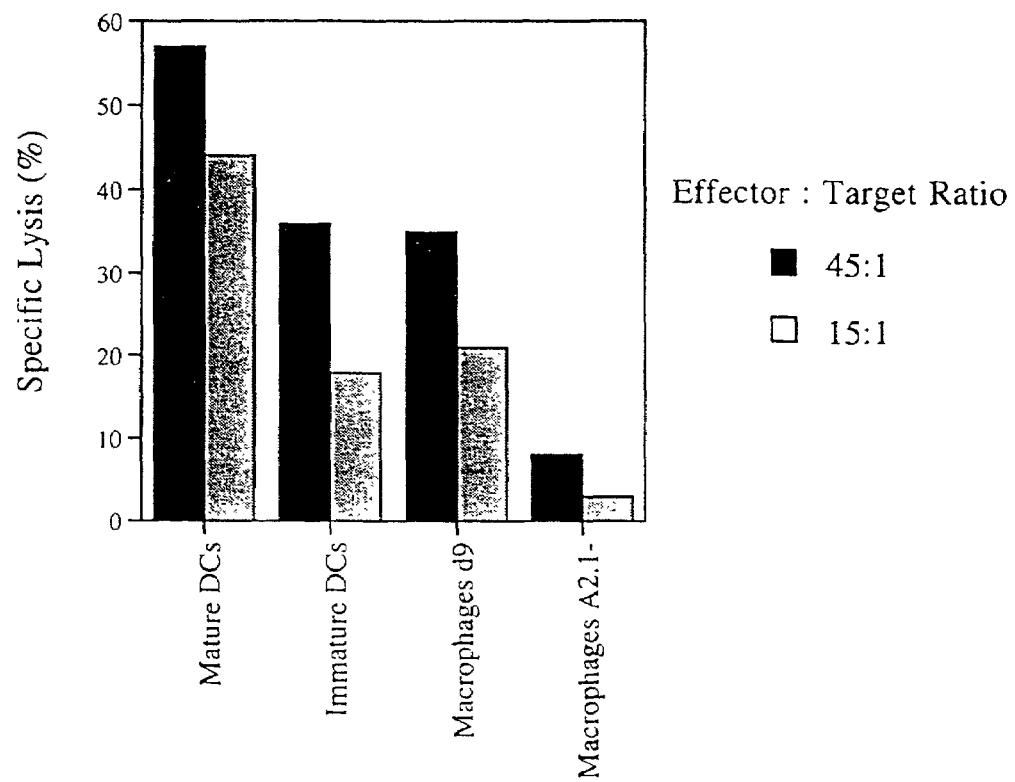

Immature DCs but not Mature DCs and not Monocytes Cross-present Apoptotic Material from Apoptotic Cells Allowing for the Targeting by Influenza-specific CTLs The following methods were used to carry out the experiments shown in FIGS. 9A and 9B.

Immature DCs but not Mature DCs or Monocytes cross-present antigenic material from apoptotic cells and become targets of antigen-specific CTLs. [FIG. 9A]. Various populations of HLA-A2.1+ professional antigen presenting cells (APCs) were co-cultured with HLA-A2.1− influenza infected monocytes. After 12 hrs, the APCs were loaded with $^{51}$Cr and used as targets for influenza-specific CTLs. Mature DCs were sorted by FACSort® (Becton Dickinson) by the DC-specific maturation marker CD83. Immature DCs were CD14− and sorted by FACSort® as a CD83− population. Mature monocytes were generated by culturing an adherent mononuclear cell fraction in a teflon beaker adherent for nine days. Immature monocytes are defined as cells cultured for two days post-plastic adherence. [FIG. 9B]. Controls included infected and uninfected APCs. HLA-A2.1− monocytes were also tested as targets to demonstrate the absence of lysis when using a mis-matched target. Effector:Target Ratios=45:1 and 15:1. Specific Lysis=(% killing of APC cross-presenting influenza infected monocytes)−(% killing of APC cross-presenting uninfected monocytes). Background lysis ranged from 0–8%.

Results

To better define the antigen presenting cell capable of cross-presentation of antigenic material derived from the engulfment of apoptotic cells, an assay was established in which the APC is used as a target for antigen-specific CTLs in a standard chromium release assay. Various populations of HLA-A2.1+ professional APCs were co-cultured with HLA-A2.1− influenza infected monocytes. After 12 hrs, the APCs were loaded with 51Cr and used as targets for an influenza-reactive CTL line. Specific lysis indicates that the APC had cross-presented antigenic material derived from the apoptotic cell, leading to the presence of specific peptide-MHC class I complexes on its surface.

While mature DCs were capable of serving as targets when infected with influenza, they were unable to engulf apoptotic cells presumably because the mechanisms of antigen uptake, phagocytosis in this case, had been down regulated. Immature DCs co-cultured with apoptotic allogeneic influenza-infected monocytes were capable of serving as targets. When cultured in the presence of conditioned media, a maturation signal for the DC, these cells upregulate costimulator molecules which apparently permit the DCs to serve as more efficient targets. Notably, neither the mature or the immature macrophages cross-presented antigenic material derived from the apoptotic cells. Unlike the mature DC population (which also do not serve as effective targets in this assay), these APCs are capable of phagocytosing apoptotic cells, however the engulfed material is most likely degraded and not cross-presented on MHC class I. When the various HLA-A2.1+ APC populations were infected with influenza, all served as effective targets demonstrating that the differences described above were not a function of MHC class I down-regulation or an inability for presentation of antigen.

The HLA-A2.1− monocytes which were used as a source of apoptotic cells were also tested as targets for the influenza-specific CTLs in order to confirm that the observed lysis was not due to killing of the allogenic influenza-infected monocytes. This result suggests that in vivo, it is the immature DC which is responsible for the uptake of apoptotic cells. After maturation and migration to a T cell rich area of a primary or secondary lymph organ, the DCs could stimulate CD8+ class-I restricted CTLs. Also indicated by this result is that the preferable method for immunotherapy would be to first co-culture immature DCs with apoptotic cells (a source of exogenous antigenic material) along with a maturation signal (CM, TNF α, IL1 β, IFN −α, or some combination of the aforementioned) prior to injection.

EXAMPLE 6

Efficient Presentation of Phagocytosed Cellular Fragments on MHC Class II Products of Dendritic Cells

Materials & Methods

Mice. Adult 6–8 week mice [BALB/C, C57BL/6, BALB/C×DBA2 F1, C57BL/6×DBA/2 F1] of both sexes were purchased from Taconic Farms [NY] and Japan SLC [Hamamatsu, Japan].

Cells. DCs were generated from bone marrow progenitors by culture in rGM-CSF as described (86). The cultures were set up in 24 well plates [Costar, Cambridge Mass.; Nunc, Naperville Ill.] and used at d6 when the wells were covered with aggregates of immature DCs. By d7-8, aggregates release mature DCs, about $10^5$/well (86). Immature but not mature DCs are phagocytic for several particulates (79). B blasts were induced with lipopolysaccharide [*E.coli* O111: B4, Sigma Chemical, St. Louis Mo., 10, μg/ml] for 3–4 d, or with anti-μ [Jackson Immunoresearch Labs, West Grove Pa.; F[ab]'$_2$ goat anti-mouse IgM] and IL-4 [Gibco-BRL] for 2 d. B cells were spleen cells that were passed over Sephadex G10 columns and depleted of T cells with antibodies and complement [thy-1, TIB 99; CD4, L3T4; CD8, TIB 211; all from ATCC]. In some cases, necrosis was induced in the B cells either by freeze-thawing 3–4 times, or with anti-B220 antibody [monoclonal J11d] and rabbit complement. Human cells were plastic adherent, monocytes from peripheral blood mononuclear cells and EBV-transformed B cell lines. Apoptosis was induced by infection with influenza (95), or by exposure to LPS [10 ng/ml] or UV light.

Antibodies. The Y-Ae hybridoma was generously provided by Dr. C. Janeway, Yale University, New Haven Conn. and grown serum-free. The IgG2b antibody was purified on protein A sepharose, biotinylated, and used in the FACS along with PE-streptavidin to detect MHC class II-peptide complexes (75,76) with a mouse IgG2b anti-human TCR antibody as the non-reactive control [PharMingen, San Diego Calif.]. The cells were double labeled for FACS and for microscopy with FITC antibodies to CD8, CD11c, CD86, I-Ab [AF6-120.1], 1-Ad [39-10-8], and I-E [14-4-4S] [PharMingen].

Capture of cell-derived peptides in vitro. Bone marrow DCs were generated in 24 well plates for 6 days in GM-CSF, gently washed to remove mature floating DCs, and then fed B blasts, human cells, or a peptide [residues 56–73 of I-Eα]. Before adding I-E$^+$ cells or peptide, the DCs were immature, since much of the MHC class II was in intracellular lysosomal compartments and CD86 was not expressed at the surface (84) After uptake of I-E, the DCs matured with high levels of surface MHC II and CD86.

Antigen presentation assays. The 20.6 T-T hybridoma recognizes the MHC II-peptide complex that is detected with Y-Ae mAb (81). Graded doses of APCs were added to $2\times10^4$ hybridoma cells in flat bottomed microtest plates. At 24 h, supernatants were assayed for IL2 using a growth assay for conA stimulated T blasts.

Capture of cell-derived peptides in vivo. $2\times10^6$ H-2d BALB/C DCs were injected in PBS into the footpads of C57BL/6 [H-2b] or as a negative control, CBA/J [H-2k] mice. After 2 days, the draining lymph nodes were removed, frozen in OCT embedding medium, sectioned, fixed in absolute acetone 5 min, and stained successively with biotin-Y-Ae, avidin alkaline phosphatase conjugates, B220 for B cells, and peroxidase labeled mouse anti-rat Ig. We then could visualize the position of blue Y-Ae$^+$ cells relative to B cells which are found in white pulp follicles and scattered through the red pulp. To identify the Y-Ae$^+$ cells, DCs were enriched from the nodes as described 25 and double labeled for biotin Y-Ae and PE streptavidin [or nonreactive biotin IgG2b mAbas control] and different FITC conjugates to CD8, B220, CD11c, I-Ab, I-Ad.

Results

The development of many immune responses requires that antigen presenting cells [APCs] present antigens that initially are expressed by other cells. This antigen transfer to APCs may often be essential, since most cell types lack the migratory and costimulatory properties required to initiate a T cell response. Examples of responses that can develop following antigen transfer, often termed cross-priming and cross-tolerance, include the rejection of malignant cells and transplants, including xenografts (64–70), and the maintenance of tolerance to self tissues (71–73). However, underlying mechanisms have been difficult to identify directly. Prior experimental approaches have utilized hematopoietic chimeras. In the chimera, the T cells that become primed to transplanted or malignant tissue [or tolerized to self] recognize antigen presenting MHC products on bone marrow-derived cells. It is possible that antigen transfer simply involves the release of peptides from donor [tumor, transplant, self tissue] to recipient APCs. We have shown in the previous examples how human dendritic cells [DCs] present viral antigens from apoptotic infected cells to MHC class I restricted, cytolytic T lymphocytes (74). In this example, we have used an antibody to directly monitor the formation of specific MHC class II peptide complexes when DCs [which are bone marrow-derived] are exposed to other noninfected cells. In vitro, we find that antigen transfer requires phagocytosis, takes place with both xenogeneic and transformed cells. In vivo, where antigen transfer can be visualized with the antibody to MHC-peptide, DCs serve as a powerful donor and recipient of cellular peptides. We propose that the steady state migration of DCs in afferent lymph, followed by processing by resident DCs in the T cell areas of lymphoid tissues, continuously tolerizes the T cell repertoire to self.

To demonstrate the capacity of DC to present peptides from other cells, we took advantage of the Y-Ae monoclonal antibody. Y-Ae sees an MHC class II-peptide complex that is formed when one MHC II product, I-Ab, presents a peptide from residues 56–73 of another MHC II product, I-Eα (75,76). Actually, the repertoire of peptides presented on MHC products typically include other MHC-derived peptides (77,78). We cultured C57BL/6 DCs [I-Eα$^-$,I-Ab$^+$] with BALB/C B cells [I-Eα$^+$,I-Ab.$^-$] and monitored the capacity of DCs to react with Y-Ae by cytofluorography. The DCs were from 6 day cultures of GM-CSF stimulated mouse bone marrow, since these are known to have phagocytic activity, in contrast to the mature nonphagocytic DCs that predominate by day 7–8 of these cultures (79). The B cells were activated 3–4 with LPS or with anti-α plus IL-4 to express high levels of MHC II (80). When returned to culture, 20–40% of the B blasts undergo apoptosis spontaneously, so that it is unnecessary to induce apoptosis in these I-E rich cells, in contrast to human monocytes [below] where the need for apoptosis is shown for transfer of cell-associated antigens to DCs.

Figure 10A:
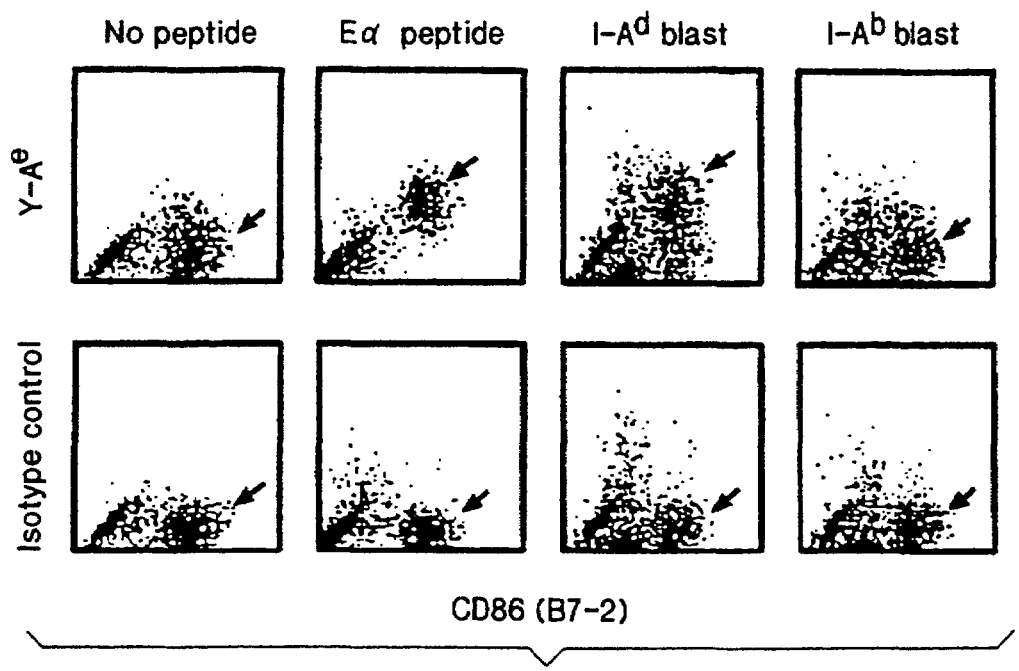
FIGS. 10A, 10B, 10C, 10D and 10E: Development of MHC-peptide complexes consisting of a B cell derived I-Eα peptide and DC-derived, I-A$^b$ MHC II products.
Figure 10B:
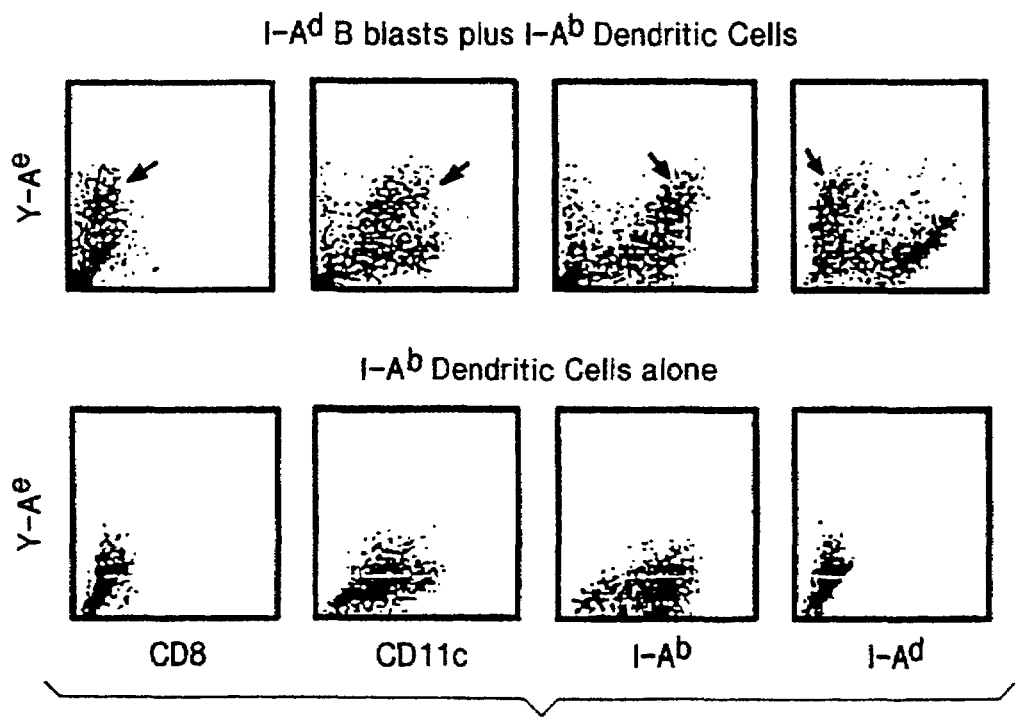
Figure 10C:
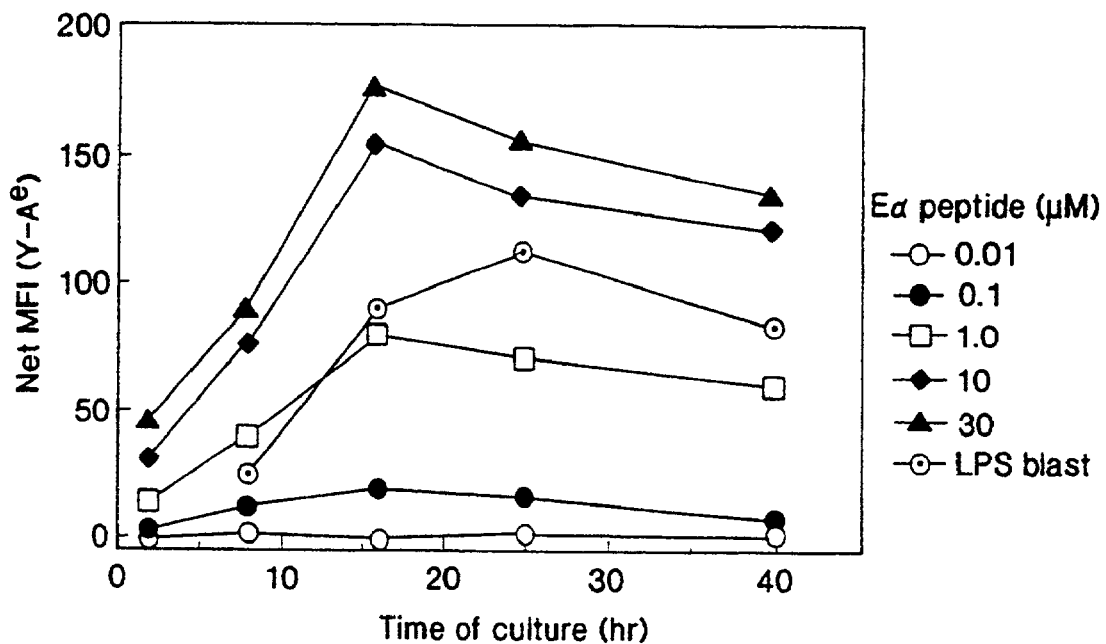
Figure 10D:
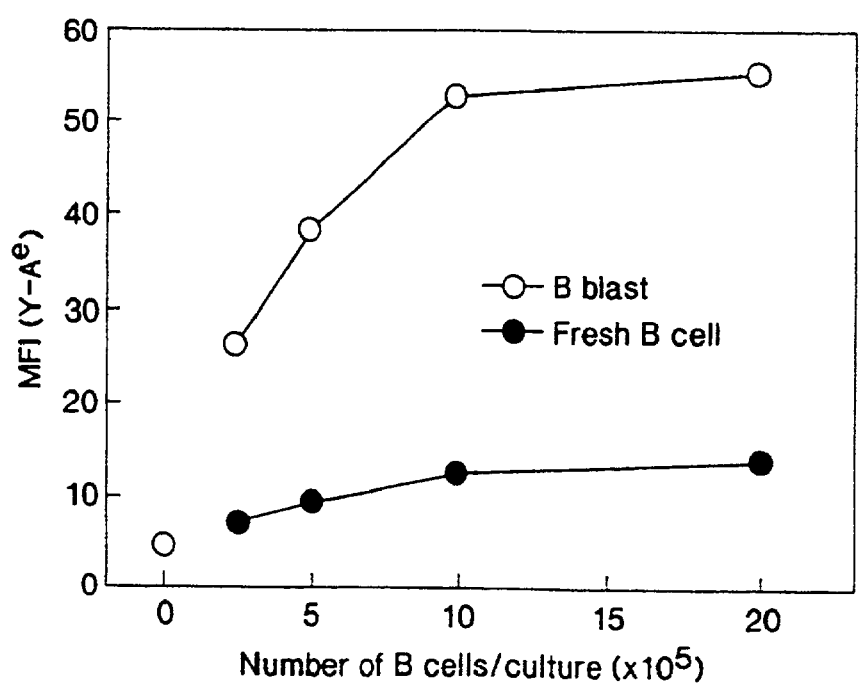
Figure 10E:
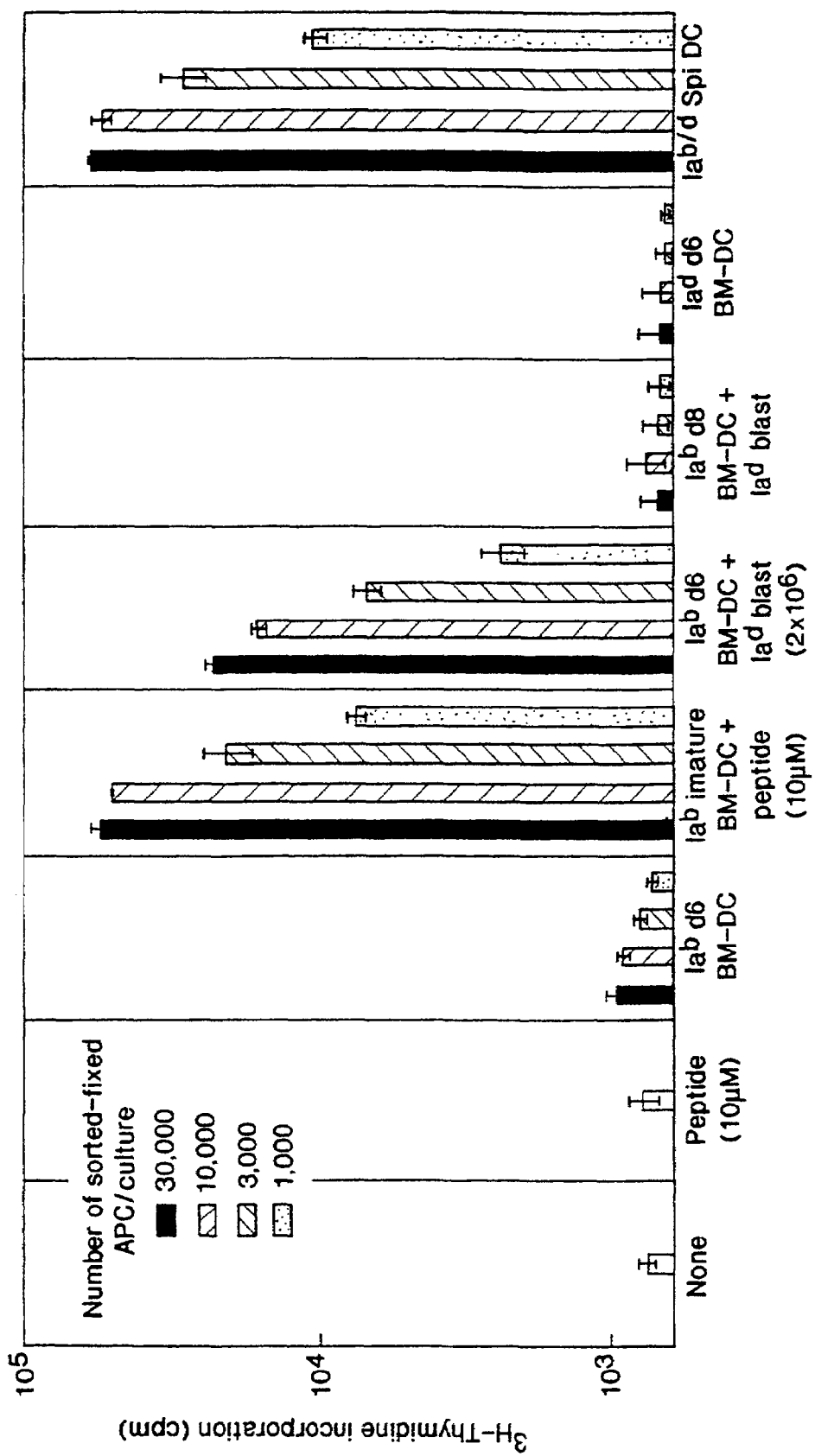

FIG. 10A illustrates data from >30 experiments. H-2b DCs were cultured for 20 h without peptide, with 1 μM I-Eα peptide, or with $2\times10^6$ B blasts from H-2d [I-Eα$^+$] or H-2b [I-Eα$^-$] mice. Y-Ae labeling developed when peptide was added. The labeling was highest on DCs that had matured to express high levels of the CD86 costimulator [black arrows denote mature DCs in each panel]. A Y-Ae signal that was comparable to that seen with peptide also developed on most DCs when I-E$^+$ [BALB/C] B blasts, but not I-E$^-$ [C57BL/6] B blasts, were added [FIG. 10A]. No labeling occurred with a nonreactive monoclonal, isotype-matched to antibody Y-Ae [FIG. 10A, lower]. The Y-Ae$^+$ cells had markers of DCs [CD11c$^+$, 1-Ab$^+$] but not donor B cells [I-Ad$^+$, CD86 low] [FIG. 10B]. No Y-Ae signal was detected on B blasts alone, or if B blasts were added to H-2d DCs [not shown]. In kinetic studies, the Y-Ae signal appeared after 5 hr of DC-B cell coculture and reached a plateau at 15–25 hr [FIG. 10C]. The signal then remained stable for 3 days, the longest we followed the cultures. The development of a Y-Ae signal on DCs depended on the B cell dose, and 4 day B blasts gave much stronger signals than unstimulated B cells [FIG. 10D].

B blasts can have 10 fold higher levels of MHC II products than small B cells (80). LPS and anti-μ blasts gave similar signals [not shown], with a plateau at a ratio of 10 B blasts per DC [FIG. 10D].

The MHC II-peptide complexes that formed during antigen transfer from B blasts to DCs could be recognized by T cells, as shown with a hybridoma that responds to the I-Ab/Eα peptide complex by secreting IL-2 (81). Following a 20 hour exposure to I-Eα peptide or B blasts, the DCs were sorted as CDllc/CD86+ cells, fixed in formaldehyde to block further processing, added in graded doses to the T-T hybridoma for 24 hrs, and then the medium collected for testing in an IL-2 bioassay [3H-TdR uptake, FIG. 10E]. DCs obtained from DC-B blast co-cultures were potent APCs for T cells, almost as potent as DCs pulsed with 1-Eα peptide and DCs expressing endogenous I-Ab complexes [I-Ab×I-E+ F1 mice].

Figure 11C:
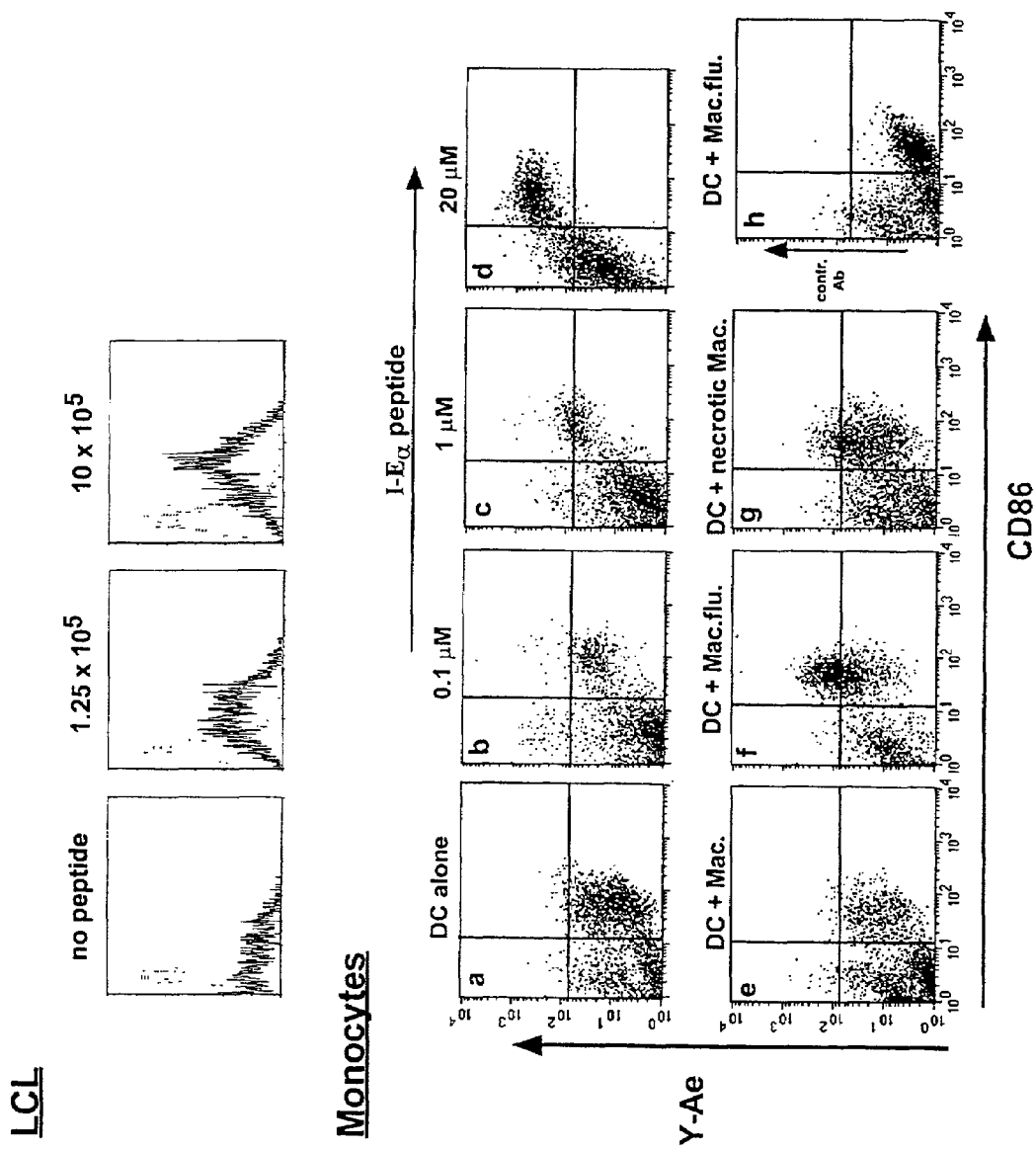

To rule out the possibility that B blasts were simply releasing peptide to the DCs, we showed that Y-Ae labeling did not develop if B blasts were separated from DCs by a Transwell filter [0.45μ pores], or if B blasts were added to nonphagocytic DCs that had undergone maturation in the bone marrow culture [FIG. 11A]. To prove that cellular processing was involved, we tested if $NH_4Cl$, which neutralizes the acidity of the endocytic system, blocked Y-Ae epitope formation. 5 mM $NH_4Cl$ partially, and 20 mM totally blocked Y-Ae development [FIG. 11B]; the inhibition was reversible [see below].

Figure 11D:
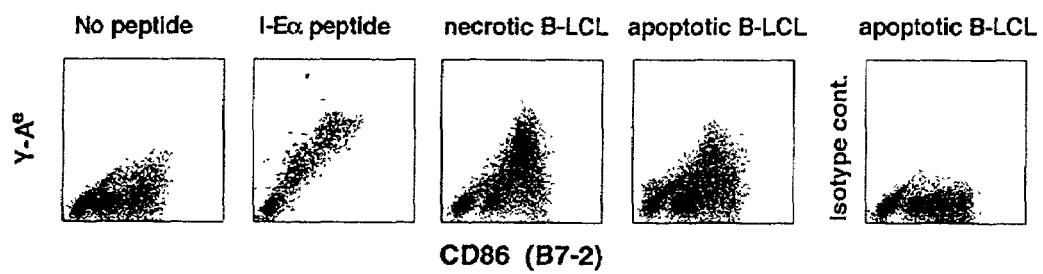

Since the immune response to xenografts also involves processing of donor cells by host APCs (70), we tested human cells as the donor of peptides to DCs. This was feasible with the Y-Ae monoclonal, since human HLA-DRα chain [residues] has the identical sequence to mouse I-Eα 56–73 (82–83). The Y-Ae epitope developed when mouse DCs were cultured with either EBV-transformed, human B lymphoblastoid cell lines [FIG. 11D] or with human monocytes [FIG. 11C]. For monocytes, we showed that apoptotic cells [induced by influenza infection or exposure to UVB light] were processed more effectively than necrotic, freeze-thawed cells and that living monocytes were not processed [FIG. 11C]. Comparable experiments on the need for apoptosis were difficult with mouse B blasts, since many of the B blasts died spontaneously in culture.

Figure 12A:
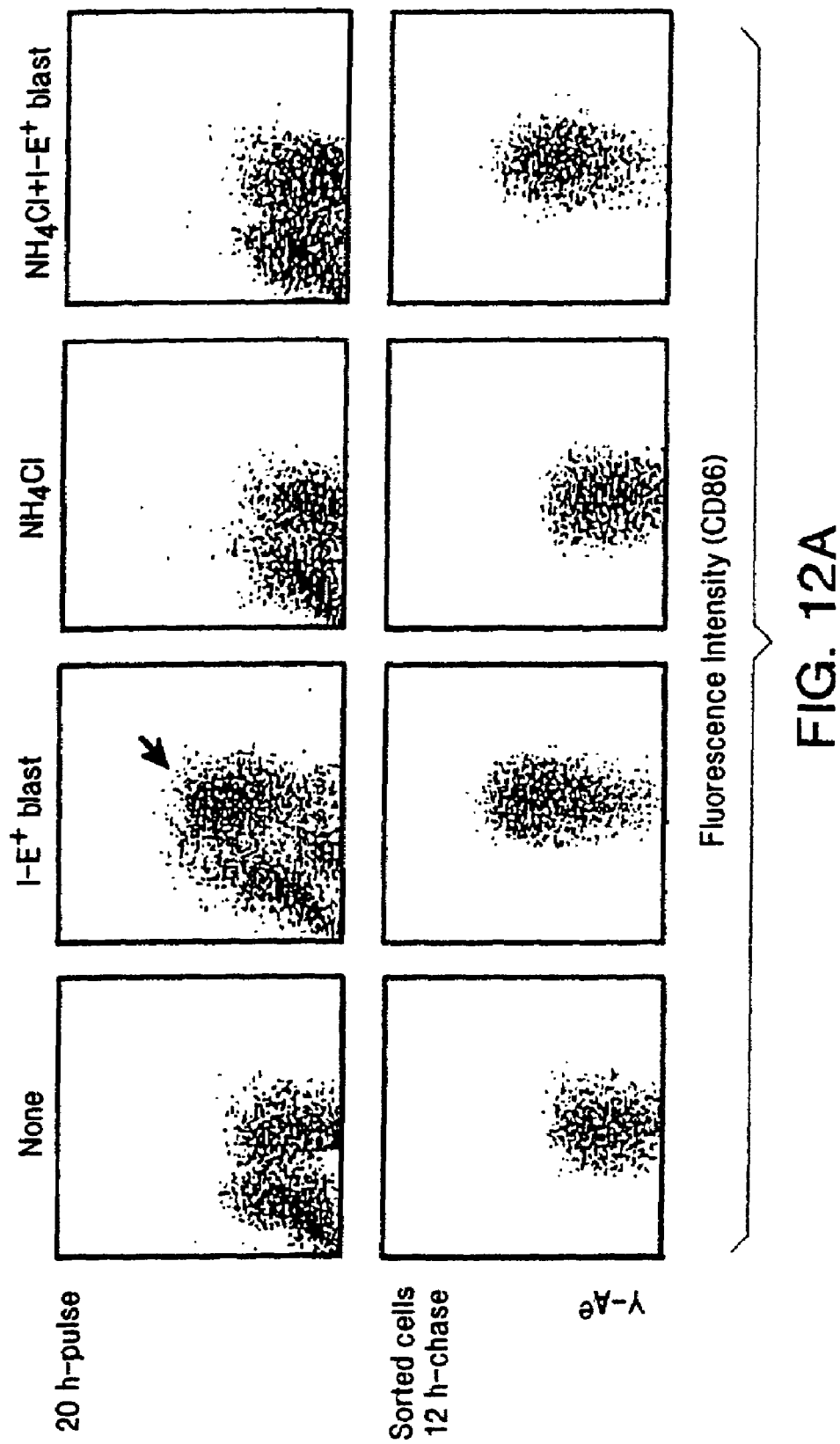
FIGS. 12A, 12B and 12C: Antigen transfer is preceded by phagocytosis. (A) Top, the formation of Y-Ae after 20 h of DC-B blast co-culture with or without 20 mM $NH_4Cl$. The DCs then were sorted as double positive for PE-CD11c and FITC-CD86, or in a second experiment, just FITC-CD86$^+$, and cultured for 12 h without $NH_4CL$ (bottom). Y-AE (biotin Y-Ae followed by Cychrome-Avidin) quickly regenerated in DCs that had been blocked by $NH_4Cl$. No Y-Ae was found in saponin-permeabilized samples of $NH_4CL$-treated cultures. (B) Immature DCs were cultured with or without 20 mM $NH_4Cl$ and 10 µM preprocessed I-E peptide for 15 h, and then Y-Ae levels were measured on the FACS®. CD86 (not shown) and Y-Ae epitope formed in the presence of $NH_4Cl$.
Figure 12B:
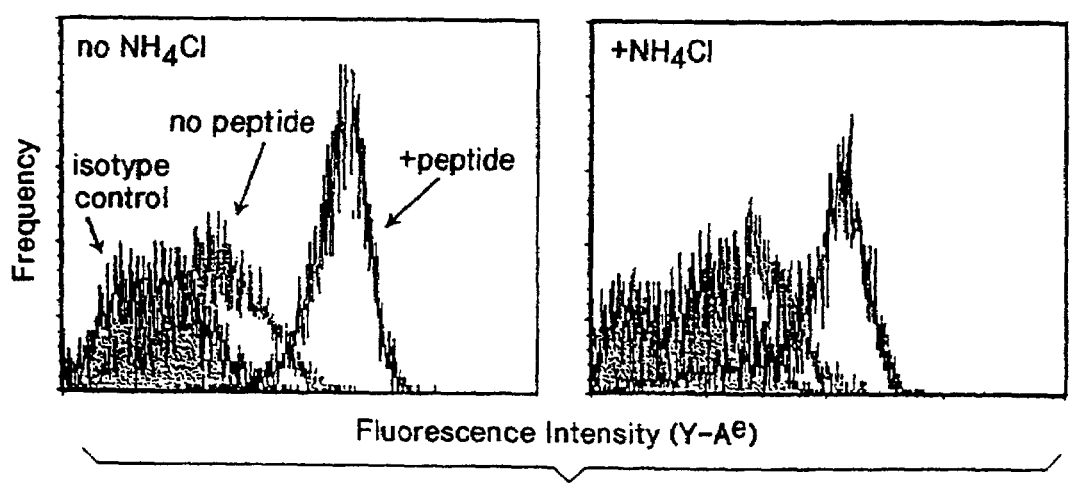
Figure 12C:
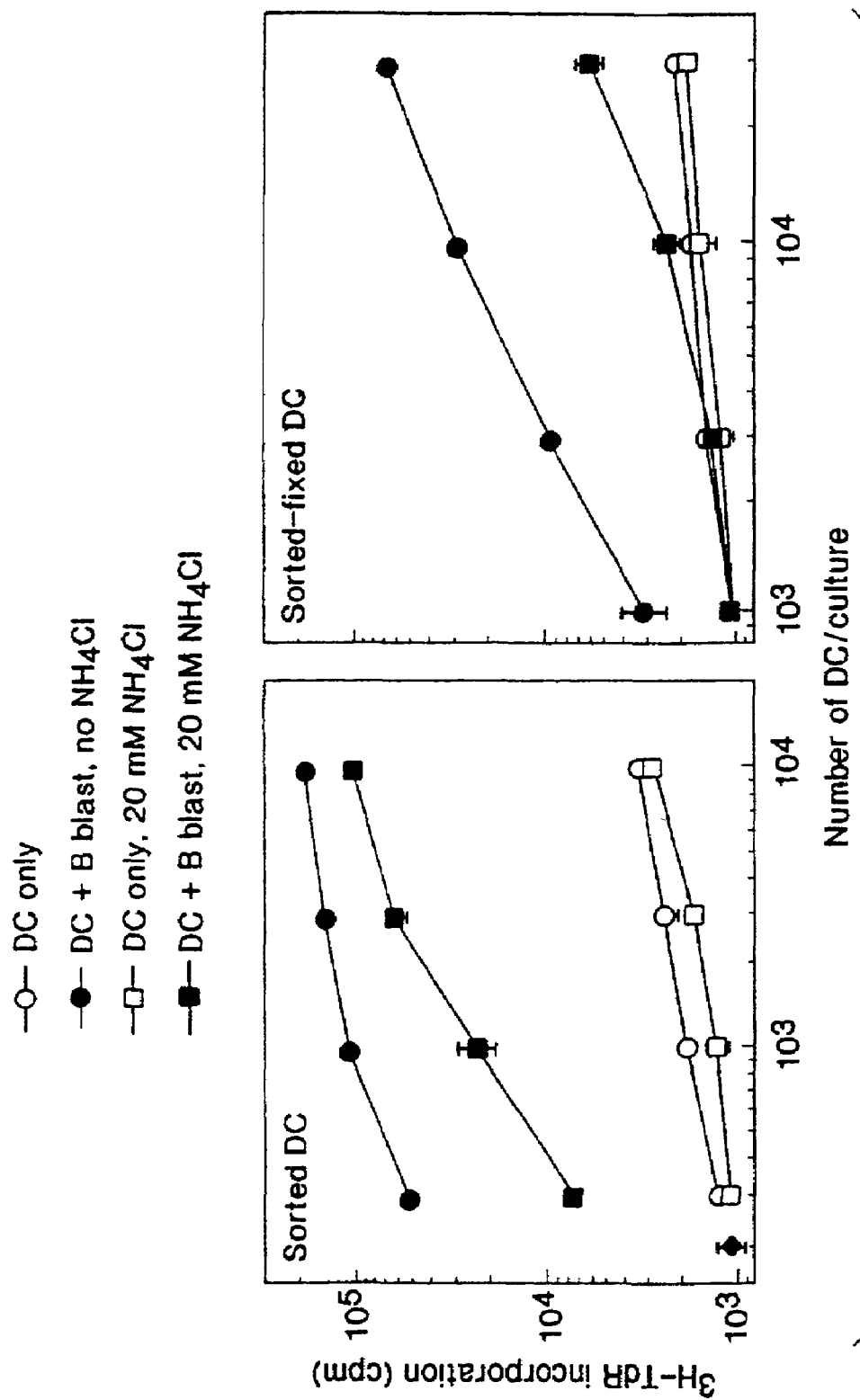

To demonstrate that phagocytosis preceded the formation of the Y-Ae epitope, B blasts were fed to DCs in 20 mM $NH_4Cl$. After 20 h, DCs were FACS® separated from residual B blasts and recultured for 12 h without $NH_4Cl$. $NH_4Cl$ completely blocked Y-Ae epitope development [FIG. 12A, top], even within saponin-permeabilized cells (not shown), but the Y-Ae reappeared after removal of $NH_4Cl$ [FIG. 12A, bottom]. The block imposed by $NH_4Cl$ seemed primarily at the level of I-E processing, rather than peptide loading, since addition of I-Eα peptide for 20 h to $NH_4Cl$ cultures led to strong Y-Ae signals comparable to non-blocked cultures [FIG. 12B].

Figure 13A:
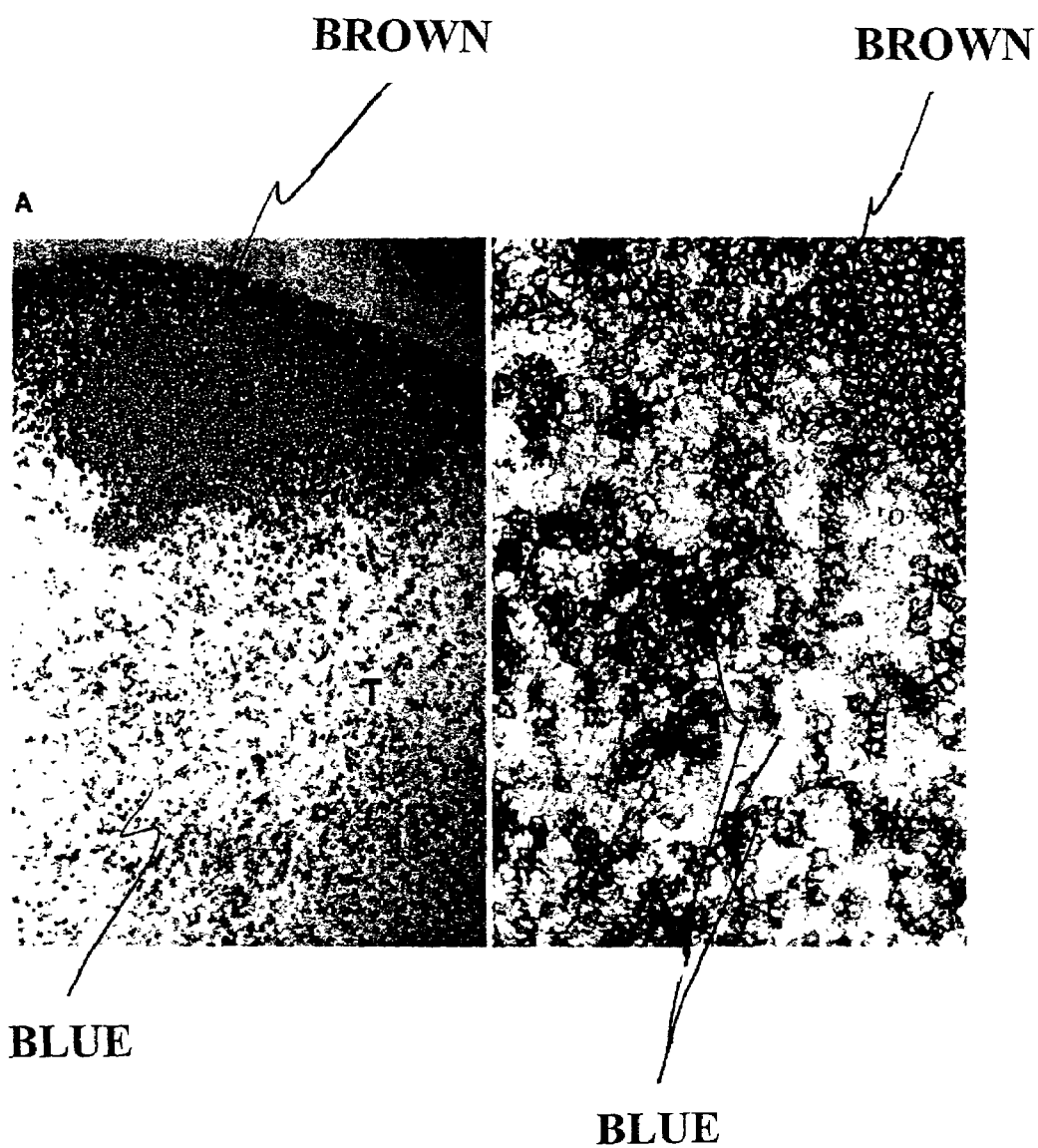
FIGS. 13A and 13B: Antigen transfer to DCs in vivo.
Figure 13B:
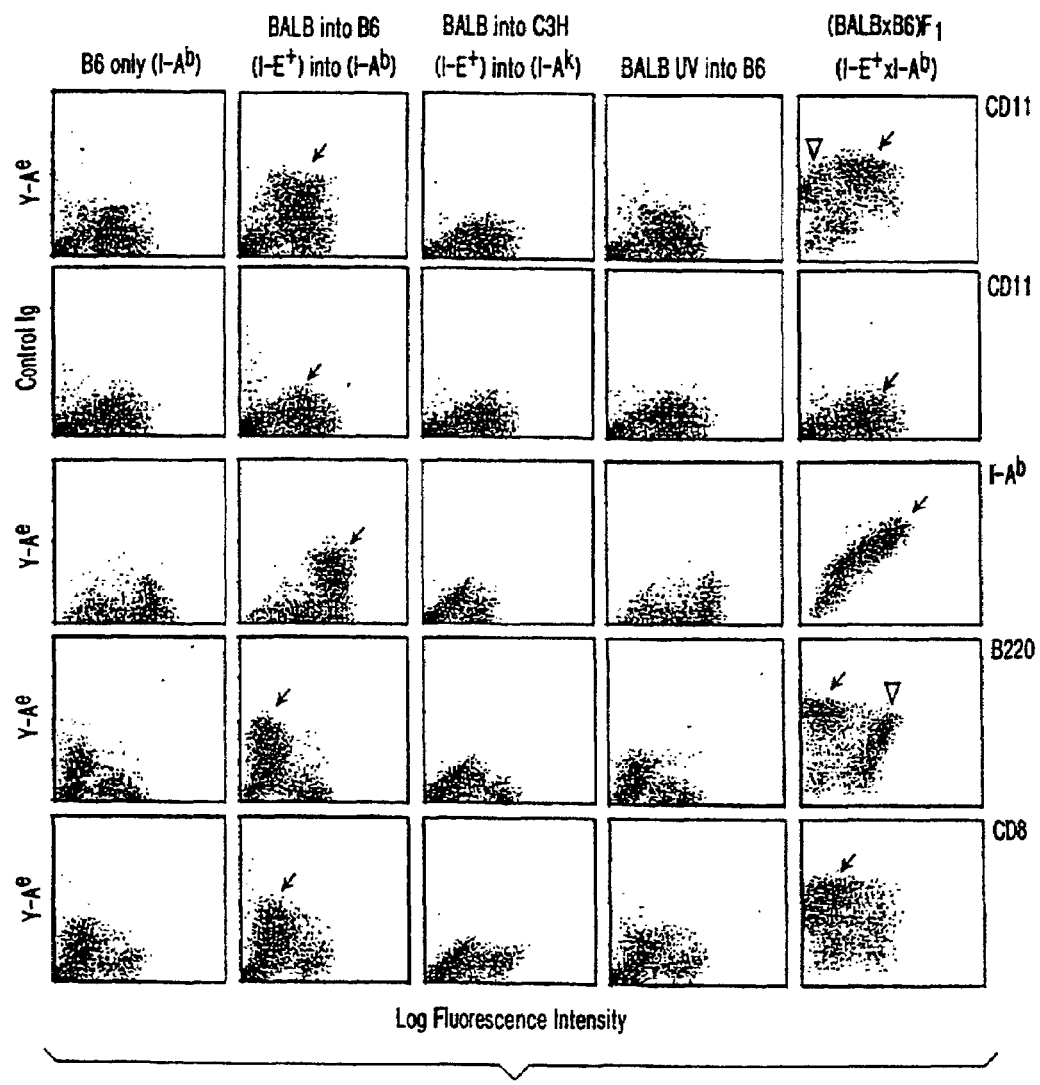
Figure 13C:
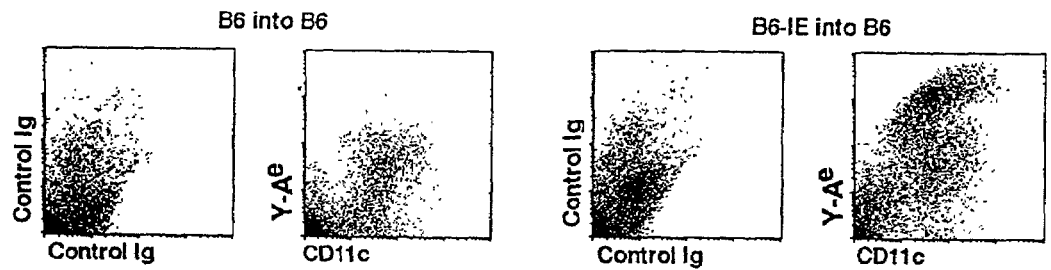
[FIG. 13C]: As in B, but the DCs were from B6. I-E transfenic (right) or B6 mice (left). Processing by host CD11c$^+$ DCs to form the Y-Ae epitope occurs when the donor and recipient DCs differ only in terms of I-E expression.

To determine whether this mechanism could function in vivo, we injected different $I-A^{b-}$ $I-E^+$ cell types [mouse splenocytes, B blasts and DCs; human monocytes] into the footpads of CS7BL/6 [$I-A^{b+}$ $I-E^-$] mice and then examined draining lymph nodes 2 days later for Y-Ae+ cells. The negative controls were H-2k C3H recipients. Only mature DCs, derived from mouse bone marrow cultures (24), were found to be efficient donors of I-E peptide to MHC II of host cells, with numerous Y-Ae+ cells developing in the DC-rich, T cell areas [FIG. 13A]. The finding was pursued by FACS analyses in which we examined cells that were enriched from the lymph nodes as described (87) [FIG. 13B]. The Y-Ae epitope was abundant, but again only in the situation where I-E+ DCs-from BALB/C or C3H/He mice were injected into I-Ab recipients [C57BL/6 but not C3H]. The Y-Ae+ cells had the phenotype of recipient DCs, positive for I-Ab and CD11c and negative for I-Ad, B220, and CD8 [FIG. 13B]. Most of the host, I-Ab and CDllc+ DCs formed Y-Ae [FIG. 13B]. Since it is known that mature DCs are short-lived in culture (26) but in vivo can home to lymphoid organs prior to dying [reviewed in 27], we tested if live DCs had to be injected to observe antigen transfer. In fact, if most of the DCs were induced to apoptose by exposure to UV light just prior to injection, only small amounts of Y-Ae were formed [FIG. 13B]. Therefore by injecting mature living DCs, one presumably maximizes the interaction of donor and recipient DCs, the latter termed interdigitating cells, in the T cell areas (90).

Many immune responses require that APCs present antigens from other cells (63–73). Most cells in the body do not migrate to the T cell areas of lymphoid tissues and lack costimulatory functions [like CD86], both properties being important for selecting and activating T cell-mediated responses. In contrast, DCs are a potent system for stimulating T cell immunity and tolerance, having the required migratory and stimulatory functions (91). This data, together with data on the presentation of apoptotic, virus-infected cells on MHC class I (74) outline a new function for DCs, the presentation of antigens from other cells.

The consequences of antigen transfer to DCs, i.e., immunity [cross-priming] vs. nonresponsiveness [cross tolerance], may be influenced by stimuli in the DC environment. When DCs capture antigens from dying cells at a site of foreign antigen deposition, e.g., when microbial agents infect and kill somatic cells, or when transplants undergo rejection by what is termed the indirect pathway, the DCs may be altered by an inflammatory stimulus to be immunogenic. On the other hand, unresponsiveness or cross tolerance may develop when DCs capture antigens chronically from the normal, noninflammatory, apoptotic turnover of cells in vivo. Cross tolerance of self-reactive T cells is observed, for example, when antigens from β cells of normal, noninflamed pancreatic islets are presented by APCs in draining lymph nodes (72,73).

Substantial numbers of DCs traffic constitutively in the afferent lymph to the T cell areas where they almost certainly die, because the numbers of DCs in lymphoid tissues are normally steady and DCs do not emerge into the efferent lymph. Prior thinking has emphasized the potential value of this migratory, short lived, patrolling DC population to pick up foreign antigens and then present these in the T cell areas. Our results suggest that migratory DCs are also being processed distributing their peptides to other DCs in lymphoid organs. In our experiments, it is unlikely that Y-Ae+ cells were first formed in the periphery since B blasts, splenocytes, UV-treated DCs and human monocytes each did not lead to Y-Ae epitope formation in lymphoid organs. Instead, it appeared necessary for viable DCs to first migrate to the lymphoid organ, and then the vast majority of host, I-Ab, lymph node DCs captured I-E+ donor DCs to form the Y-Ae MHC-peptide complexes. The recipient Y-Ae+ cells in the T cell areas, sometimes termed "lymphoid DCs," may be long-lived and are thought to have a regulatory function (90,92). In the steady state, i.e., in the absence of inflammatory signals, the continued processing of migratory DCs and any cellular antigens that they have acquired from the normal turnover of cells in tissues, could purge the T cell repertoire of self reactivity (72,73), a function that is also carried out on developing T cells by DCs in the thymus (93,94). As result, when foreign inflammatory stimuli are to be presented to the immune system by DCs, there is less chance that autoreactivity to self antigens develops, since the same DC system has inactivated self reactive cells beforehand.

EXAMPLE 7

Immature Dendritic Cells Phagocytose Apoptotic Cells via $\alpha_v\beta_5$ and CD36, and Cross-present Antigens to CTLs Materials & Methods Media. RPMI 1640 supplemented with 20 μg/ml of gentamicin [Gibco BRL], 10 mM HEPES [Cellgro] and either 1% human plasma, 5% pooled human serum [c-six diagnostics] or 5% single donor human serum was used for DC preparation, cell isolation and culture conditions (113,119).

Preparation of Cells. Peripheral blood mononuclear cells [PBMCs], DCs, macrophages and T cells were prepared as previously described (113,114,119). Briefly, peripheral blood was obtained from normal donors in heparinized syringes and PBMCs were isolated by sedimentation over Ficoll-Hypaque [Pharmacia Biotech]. T cell enriched and T cell depleted fractions were prepared by resetting with neuraminidase-treated sheep red blood cells (119). Immature dendritic cells [DCs] were prepared from the T cell depleted fraction by culturing cells in the presence of granulocyte and macrophage colony-stimulating factor [GM-CSF] and interleukin 4 [IL-4] for 7 days. 1000 U/ml of GM-CSF [Immunex Corp.] and 500–1000 U/ml of IL4 [Schering-Plough Corp.] were added to the cultures on days 0, 2 and 4. To generate mature DCs, the cultures were transferred to fresh wells on day 7 and monocyte conditioned media [MCM] was added for an additional 3–4 days (113,114). At day 7, >95% of the cells were CD14$^-$, CD83$^-$, HLA-DR$^{lo}$ DCs. On day 10–11, 80–100% of the cells were of the mature CD14$^-$, CD83$^+$, HLA-DR$^{hi}$ phenotype. FACSort® was used to generate highly pure populations of immature and mature DCs, based on their CD83$^-$ and CD83$^+$ phenotype, respectively. Macrophages were isolated from T cell depleted fractions by plastic adherence for one hour. After 24 hrs., cells were removed from the plates and placed in Teflon beakers for 3–9 days. T cells were further purified from the T cell enriched fraction by removing contaminating monocytes, NK cells and B cells (119).

Antibodies. Antibodies to the following proteins were used: CD8-PE, CD14-PE, HLA-DR-PE, HLA-DR-biotin [Becton Dickinson], IgG2b [clone 6603001, Coulter], CD8 [CRL 8014, ATCC], CD83 [clone HB15a, Coulter], MHC I [W6/32, ATCC clone HB95], CD36 [clone FA6, obtained from the Vth international workshop on leukocyte differentiation antigens], $\alpha_v$ [clone CLB-706, Chemicon International Inc.; clone 69.6.5, Coulter], $\beta_1$ [clone 6S6, Chemicon International Inc.], $\beta_3$ [clone SZ21, Coulter; clone RUU-PL 7F12, Becton Dickinson], $\beta_5$ [clone B5-IVF2, Upstate biotechnology], $\alpha_v\beta_3$ [clone 23C6, Pharmingen], $\alpha_v\beta_5$ [clone P1F6, Chemicon International Inc.], CD71 [Dako], Mannose receptor [clone 3.2PB1, a gift from A. Lanzavecchia], Nucleoprotein [ATCC clone HB85].

Induction of apoptotic death. Monocytes were infected with influenza virus in serum free RPMI. These cells undergo viral induced apoptotic death within 6–8 hours. Cell death was confirmed using the Early Apoptosis Detection Kit [Kayima Biomedical] (102). As previously described, cells are stained with Annexin V-FITC [Ann V] and Propidium Iodide [PI]. Early apoptosis is defined by Ann V$^+$/PI$^-$ staining as determined by FACScan® [Becton Dickinson]. To ensure that we were studying the uptake of early apoptotic cells, the kinetics of death were carefully worked out. 5–8 hours post-infection, monocytes first externalize PS on the outer leaflet of their cell membrane, as detected with Ann V. By 8–10 hours, these cells were TUNEL positive. It was not until 24–36 hours that the majority of the monocyte population included trypan blue into the cytoplasm, an indicator of secondary necrosis [unpublished data, (120, 121)]. HeLa cells were triggered to undergo apoptosis using a 60UVB lamp [Derma Control Inc.], calibrated to provide 2 mJ/cm$^2$/sec. The kinetics of cell death in these cells has been previously defined (99).

Phagocytosis of apoptotic cells. Monocytes or HeLa cells were dyed red using PKH26-GL [Sigma Biosciences], and induced to undergo apoptosis by influenza infection or UVB irradiation, respectively. After 6–8 hours, allowing time for the cells to undergo apoptosis, they were co-cultured with phagocytic cells that were dyed green using PKH67-GL [Sigma Biosciences], at a ratio of 1:1. Macrophages were used 3–6 days after isolation from peripheral blood; immature DCs were used on day 6–7 of culture; and mature DCs were used on day 10–11. Where direct comparison of cells was needed, cells were prepared from the same donor on different days. In blocking experiments, the immature DCs were pre-incubated in the presence of 50 μg/ml of various monoclonal antibodies for 30 minutes prior to the establishment of co-cultures. After 45–120 minutes, FACScan® analysis was performed and double positive cells were enumerated.

Phagocytosis of latex beads. Immature DCs were preincubated at 37° C. with monoclonal antibodies specific for $\alpha_v$ and $\alpha_v\beta_5$. $10^6$ cells were then cultured with $5\times10^7$ red fluorescent microspheres [diameter 1μ, 2.5% solids, carboxylate modified latex; Sigma] for varying periods of time. Alternatively, the cells were maintained 4° C. At the end of the assay, cells were separated from unengulfed beads by density gradient centrifugation and analyzed by FACScan® analysis (122).

Immunofluorescence. Cells were adhered to Alcian Blue [Sigma] treated cover slips and fixed in 100% acetone. Cells were stained with anti-influenza nucleoprotein antibody [HB85, ATCC] and Texas red conjugated goat anti-mouse IgG [Jackson ImmunoResearch]. This was followed by staining with biotinylated anti-HLA-DR [Becton Dickinson] followed by FITC conjugated streptavidin [Jackson ImmunoResearch]. Cells were visualized using an Zeiss Axioplan2 microscope.

Assay for cross-priming of apoptotic cells. Various APC populations were prepared as described above from HLA-A2.1$^+$ donors. Mature DCs were further purified by labeling with the DC-restricted marker CD83, followed by cell sorting on the FACSort® [Becton Dickinson]. Immature DCs were CD14$^-$ and sorted by FACSort® as a CD83$^-$ population. Mature macrophages were generated by culturing an adherent mononuclear cell fraction in a Teflon beaker for 9 days. These APC populations were co-cultured with HLA-A2.1$^-$ influenza-infected monocytes. After 12 hr., the APCs were loaded with Na$^{51}$CrO$_4$, and used as targets for influenza-specific CTLs in a standard chromium release assay (102,119). Specific lysis indicates that the APC had cross-presented antigenic material derived from the apoptotic cell, leading to the formation of specific peptide-MHC class I complexes on its surface. Specific Lysis=[% killing of APC cross-presenting influenza infected monocytes]–[% killing of APC cross-presenting uninfected monocytes].

Background lysis ranged from 0–8%. Controls included influenza infected and uninfected mature DCs, immature DCs and macrophages. The HLA-A2.1$^-$ monocytes used as a source of apoptotic material were also tested as targets to demonstrate the absence of lysis when using a mis-matched target. For the control targets, specific Lysis=[% killing of influenza infected APC]–[% killing of uninfected APC]. Background lysis ranged from 0–5%. Maximal influenza specific killing was determined using T2 cells [a TAP$^{-/-}$, HLA-A2.1$^+$, class II$^-$ cell line] pulsed for 1 hr with 1 M of the immunodominant influenza matrix peptide, GILG-FVFTL as targets (123). Responses varied from 25–60% as a function of the individual's prior exposure to influenza.

RT-PCR. RNA was purified from highly purified sorted cell populations of immature and mature DCs as described above. Messenger RNA for $\beta_3$, $\beta_5$ and CD36 were identified using an one step RT-PCR reaction [Titan kit, Boehringer Mannheim]. The forward primer 5'-TGAGAAGTGCCCCT-GCCC was used for both $\beta_3$ and $\beta_5$. The reverse primers 5'-GTTGGCTGTGTCCCATTTTGCT and 5'-TTGTAG-GATTTGTGAACTTG were used for $\beta_3$ and $\beta_5$ to obtain 438 bp and 509 bp products, respectively [primer sequences were generously provided by S. Silletti]. The forward primer 5'-GGGAATTCATATGAAATCATAAAAGCAA-CAAACAT and the reverse primer 5'CGGAATTCTA-CATTTCACTTCCTCATTTTCTG for CD36 yielded a product of 392 bp (124). The RT reaction was carried out for 30 minutes at 56° C. followed by 30 cycles of amplification. After 30 cycles of PCR the samples were visualized on an agarose gel.

Results

Figure 20B:
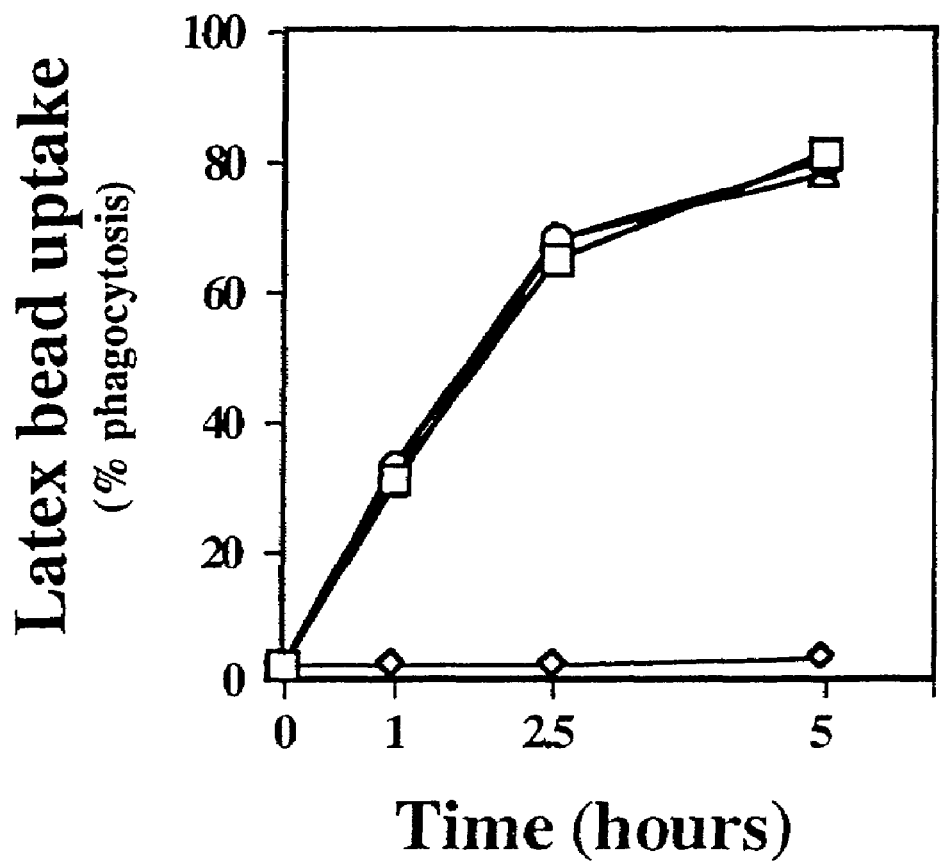
Figure 22A:
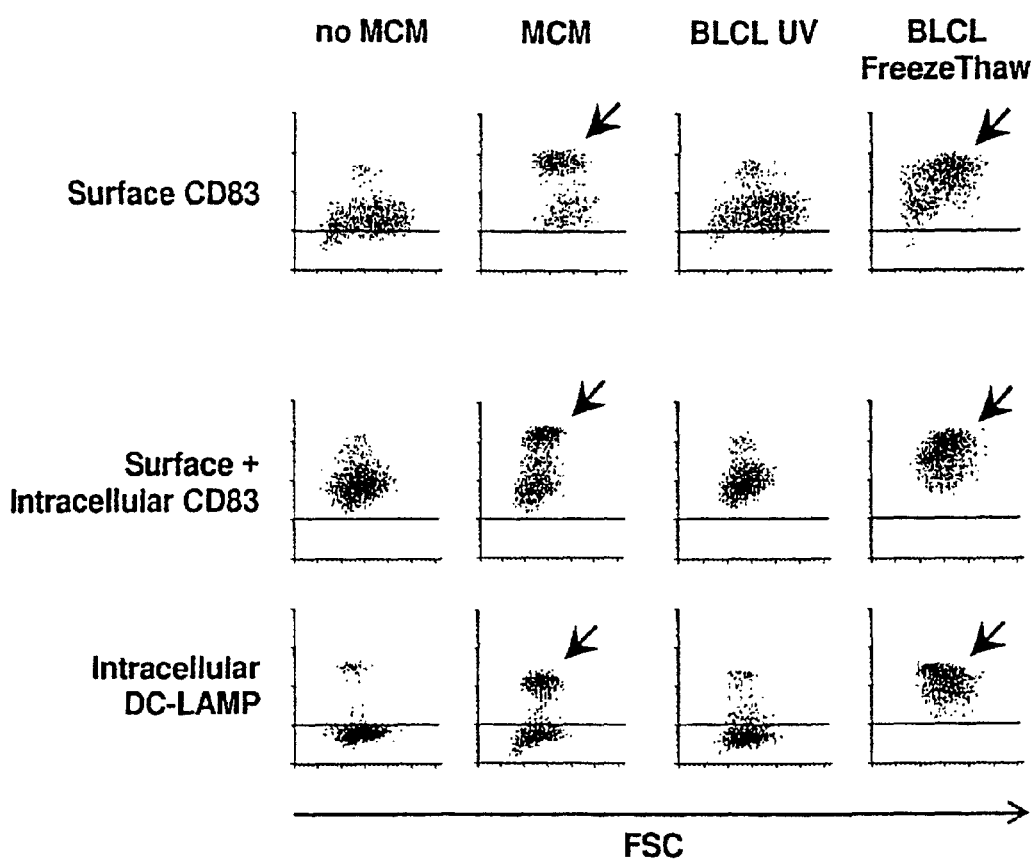
Figure 22B:
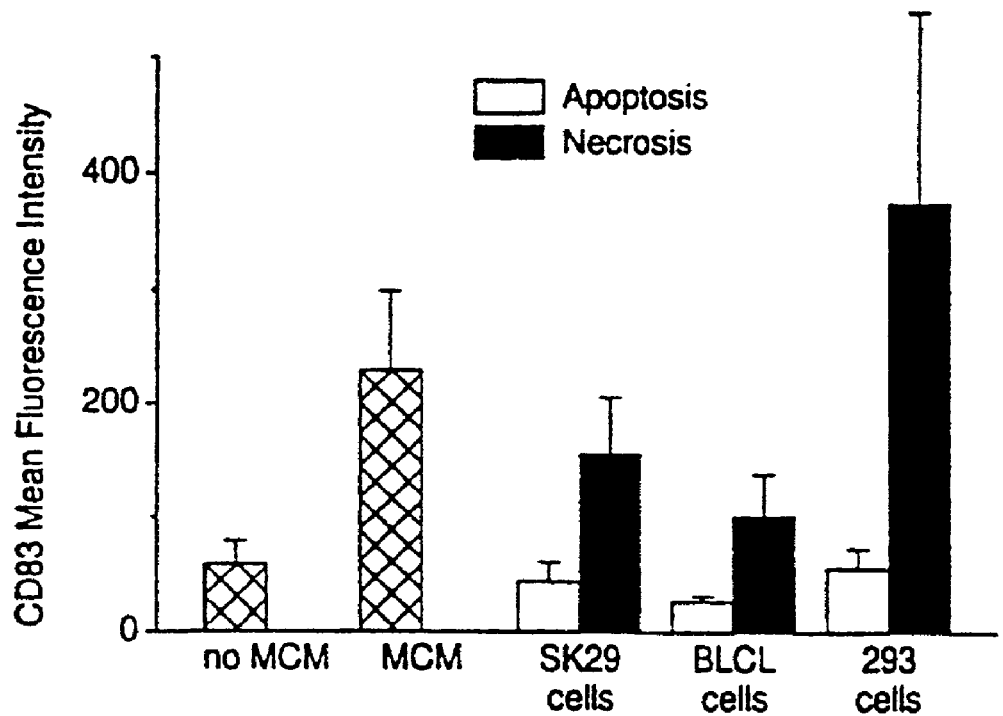
Figure 22C:
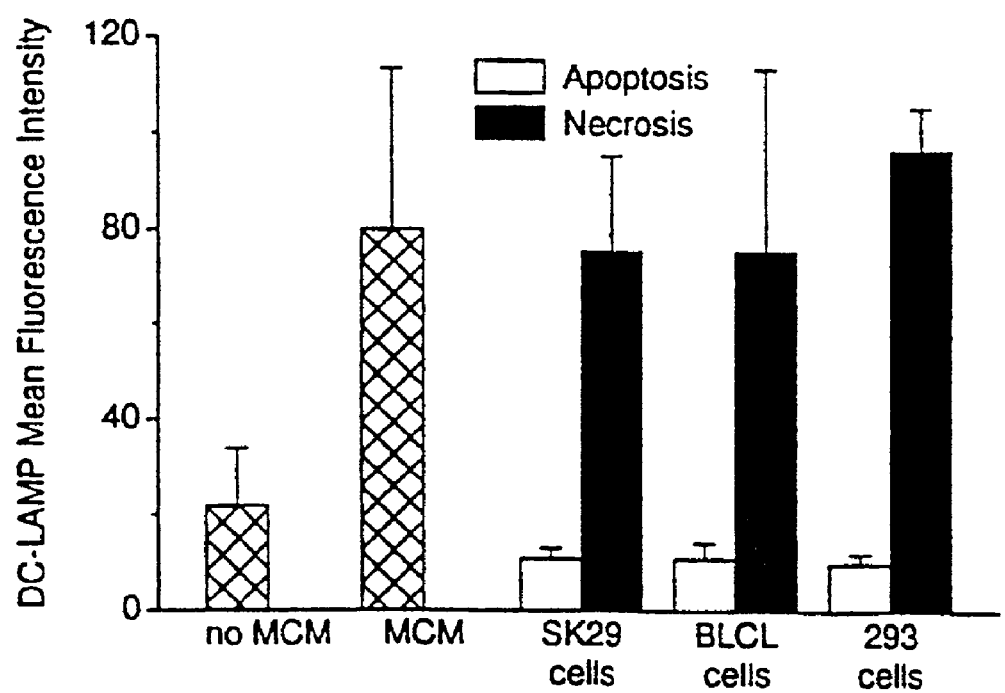
Figure 22D:
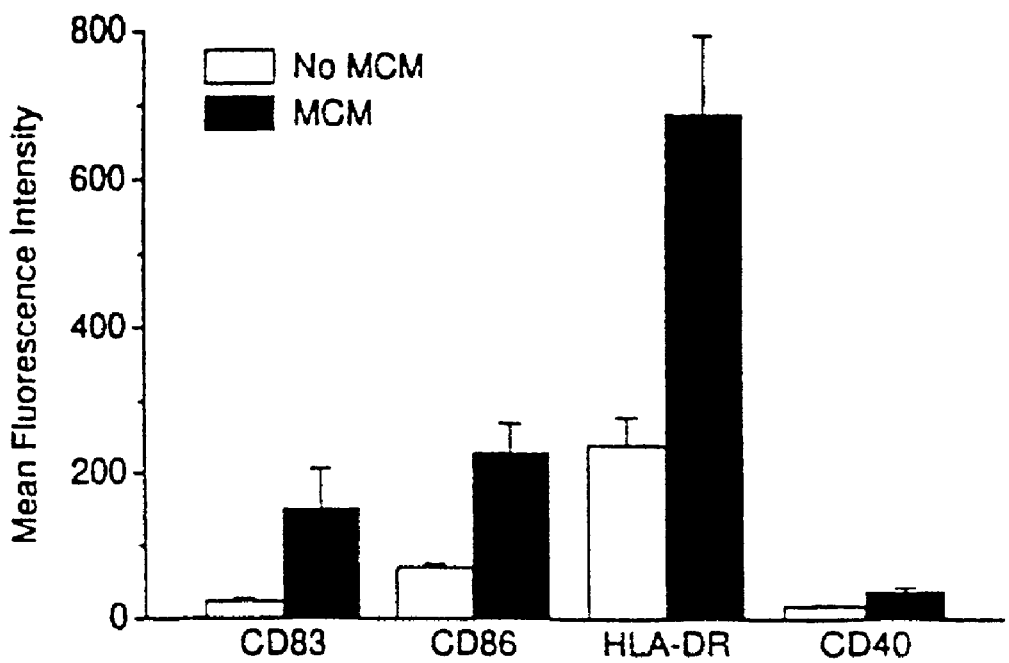
Figure 22E:
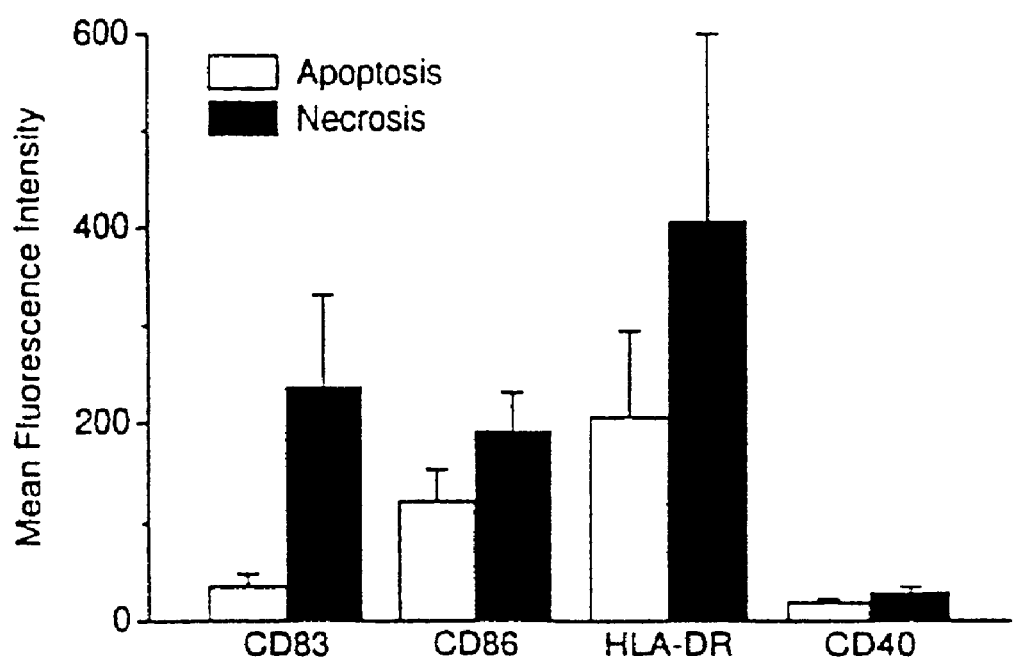
Figure 22F:
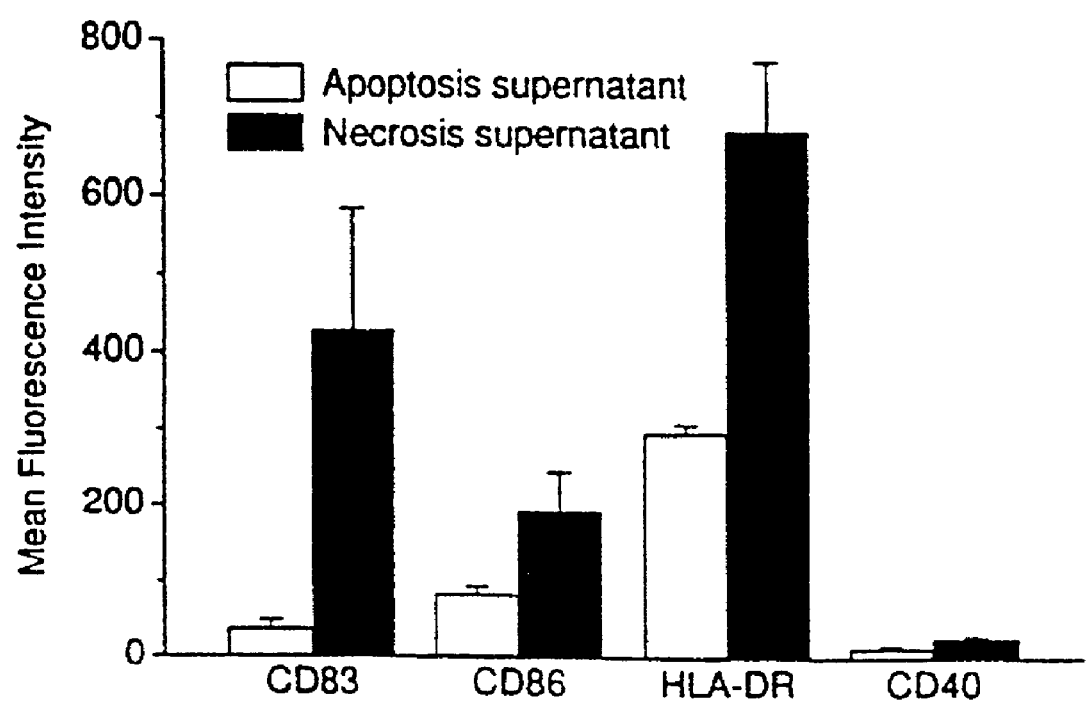

Immature DCs efficiently phagocytose apoptotic cells. Based on previous observations that immature DCs are the cells responsible for capturing antigen (106), we predicted that apoptotic cells would be engulfed best by immature DCs. To test this hypothesis, we established a phagocytosis assay which allowed us to visually detect the uptake of apoptotic cells, and compare the phagocytic capacity of immature DCs, mature DCs and macrophages. Briefly, immature DCs were prepared by culturing a T-cell depleted fraction from peripheral blood in the presence of IL-4 and GM-CSF. Mature DCs were generated with the addition of monocyte conditioned medium [MCM] and these cells expressed the cell surface DC restricted maturation marker CD83 (113,114,125). Macrophages were prepared by culturing a plastic adherent cell population in Teflon beakers for 3–9 days. As a source of apoptotic cells we used influenza infected monocytes (102); virus infection induces apoptotic death in these cells within 6–10 hours (102,120,121). Monocytes were first dyed red using PKH26-GL [Sigma Biosciences], and then infected with influenza virus as previously described (119). After 6–8 hours, the various APCs were dyed green using the fluorescent cell linker compound, PKH67-GL [Sigma Biosciences], and co-cultured with the apoptotic cells at a ratio of 1:1. After 2 hours at 37+ C., co-cultures of cells were analyzed by FACScan® analysis, allowing for quantification of phagocytic uptake as double positive cells. 80% of the macrophages, 50% of the immature DCs, and less than 10% of the mature DCs engulfed the apoptotic monocytes after 2 hours of coculture [FIG. 14A]. The smear of double positive cells [PKH67 labeled APC that engulfed the PKH26 labeled apoptotic cells] indicates that both apoptotic bodies and whole apoptotic cells served as 'food' for the phagocytic cell [FIG. 14. panels iii., vi., ix.]. Note that as the forward scatter of the APCs increased and the setting of the FACS® shifted, the dying monocytes were excluded from the established region [FIG. 14. panels ii., v., viii.]. Maximal uptake by all APC populations was achieved within 2–4 hours and in part depended upon the source of apoptotic cell used [FIG. 14B and data not shown]. Given this kinetic data, we believe that macrophages and DCs engage and internalize dying cells while they still display features of early apoptotic death. This data also demonstrates that it is the immature DC which preferentially acquires apoptotic material as compared to the mature DC. The source of apoptotic cells was not critical, since we obtained similar results with UVB irradiated HeLa cells [FIG. 20 and data not shown].

To confirm that this FACS® assay was measuring phagocytosis, we carried out the assay at 4° C. and in the presence of inhibitors of phagocytosis. Both low temperature [FIG. 15A], and cytochalasin D, an inhibitor of cytoskeletal function, blocked uptake [FIG. 15B]. Phagocytosis by immature DCs also requires divalent cations as EDTA was inhibitory [FIG. 15C]. To visually confirm the uptake recorded by FACS®, we prepared cytospins of the dyed co-cultures. The frequency of uptake correlated with that measured on FACS® [data not shown]. We also performed immunofluorescence on co-cultures of immature DCs, labeled with anti-HLA-DR [DR], and apoptotic influenza infected monocytes, labeled with anti-influenza nucleoprotein [NP] [FIG. 16]. In the top panel an apoptotic cell is seen just prior to being engulfed by a DC [large arrowhead]. Following phagocytosis, apoptotic cells were found in DR$^+$ vesicles [small arrows], but not in the cytoplasm.

Only immature DCs cross-present antigen from the apoptotic cell on class I MHC. We next correlated the phagocytic capability of macrophages and DCs with their ability to cross-present antigenic material derived from apoptotic cells. The cells were prepared from HLA-A2.1$^+$ donors (113,114), co-cultured with HLA-A2.1$^-$ influenza-infected monocytes for 12 hr and then loaded with Na$^{51}$CrO$_4$ for use as targets for influenza-specific CTLs (102,119). Specific lysis indicates that the APC cross-presented antigenic material derived from the apoptotic cell, by forming specific peptide-MHC class I complexes on its surface [FIG. 17A]. As a direct comparison with the endogenous pathway for class I MHC presentation, the same APC populations were infected with live influenza virus and used as targets [FIG. 17B].

While mature DCs were efficient targets when infected with influenza, they were unable to cross-present antigens, presumably because they had down regulated the ability to phagocytose the apoptotic monocytes. The immature DCs, however, did cross-present antigens from apoptotic cells. Furthermore, if the immature DCs were co-cultured with the apoptotic cells in the presence of MCM, a maturation stimulus, they were even better targets. This is possibly due to the up regulation of costimulator and adhesion molecules 108,126), or the increased stability of peptide-MHC I complexes. Given that maximal uptake of apoptotic cells by immature DCs occurs between 2–4 hours [FIG. 14B], we believe that cross-presentation of apoptotic material reflects of the phagocytosis and processing of early apoptotic cells rather than secondary necrotic cells [see Methods]. With respect to this issue, it is important to recognize that the influenza infected monocytes require 24 hours to undergo secondary necrosis [unpublished data, (120,121)].

Figure 14A:
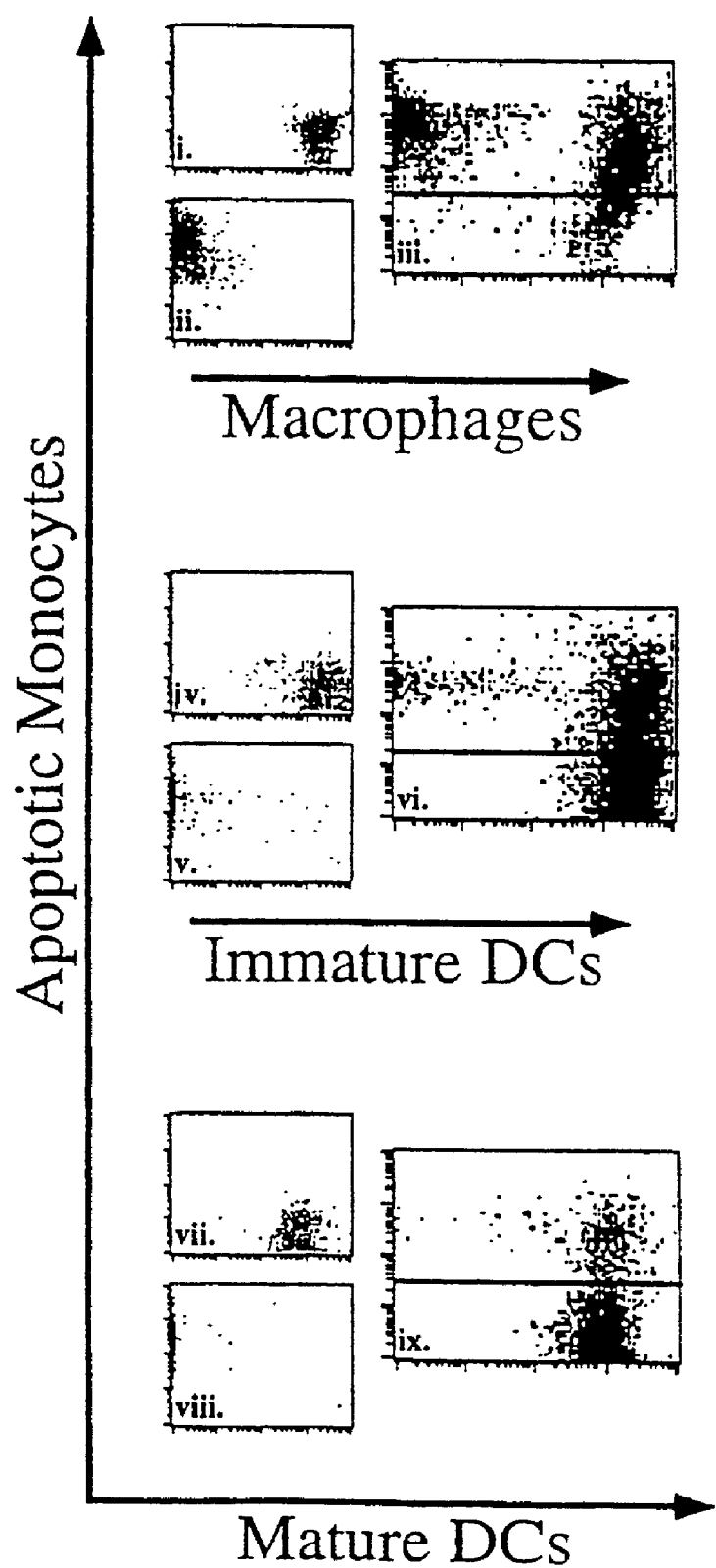
FIGS. 14A and 14B: Immature but not mature dendritic cells efficiently phagocytose apoptotic cells.
Figure 14B:
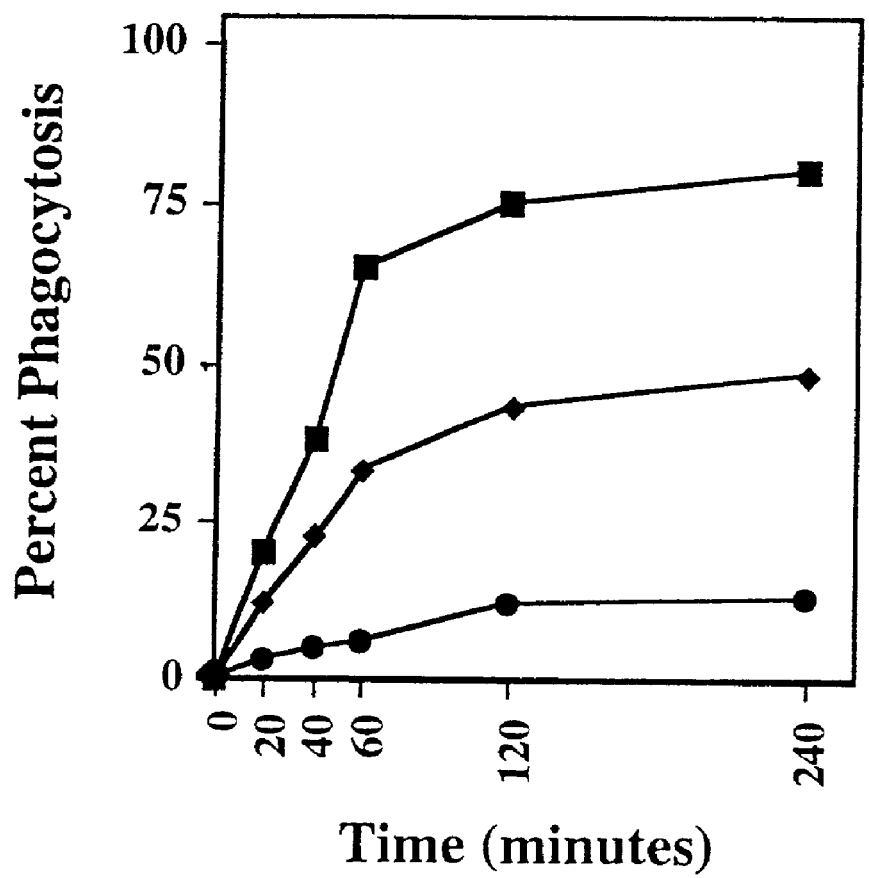

Notably, macrophages which efficiently phagocytose apoptotic cells [FIG. 14A], did not cross-present antigens to CTLs [FIG. 17B]. Presumably, the engulfed material is degraded, not cross-presented on MHC I. This profound difference between the DC and macrophage populations is supported by our previous findings that macrophages do not cross-present antigens from apoptotic cells during the induction phase of a class I-restricted antigen-specific T cell response. In fact, when put into culture with DCs in a competition assay, they sequester the apoptotic material and abrogate the CTL response (102).

Immature DCs can be distinguished from macrophages by intracellular expression of CD83 and a unique profile of phagocytic receptors. We investigated the possibility that immature DCs might phagocytose apoptotic cells via pathways distinct from macrophages. To clearly distinguish these cells we characterized them phenotypically. Immature DCs are distinguished by the absence of both CD14, a macrophage restricted marker, and CD83, a maturation marker for DCs (125). We have extended the use of CD83, finding that immature DCs can be distinguished from both macrophages and mature DCs by their intracellular expression of CD83 [FIG. 18]. Macrophages do not express CD83 intracellularly nor extracellularly [FIG. 18], while mature DCs express CD83 both intracellularly and extracellularly [FIG. 18].

These APC populations were examined for receptors involved in phagocytosing apoptotic material [Table 1]. These include: $\alpha_v\beta_3$ and CD36 which act as co-receptors, for engulfment of apoptotic neutrophils and lymphocytes by macrophages (127,128); and CD14 which has been implicated in the uptake of apoptotic cells by macrophages (129). While studying the immature DC populations, we identified a discrepancy in the expression of the $\alpha_v$ and $\beta_3$ integrin chains and investigated the possibility that $\alpha_v$ was dimerizing with an alternate $\beta$ chain. Using antibodies which recognize combined epitopes of the $\alpha_v\beta_3$ and the $\alpha_v\beta_5$ heterodimers, we noted the selective expression of $\alpha_v\beta_5$ on immature DCs [FIG. 19A]. As is true for most receptors involved in antigen uptake (106,107), the expression of CD36, $\alpha_v\beta_5$ and mannose receptor on DCs is down regulated with maturation [FIG. 19B, Table 1].

To evaluate whether this down regulation could be observed on the level of mRNA expression, we performed RT-PCR using primers specific for $\beta_3$, $\beta_5$ and CD36 [FIG. 19C]. Immature DCs [lane 1] showed amplified DNA of the appropriate size for $\beta_3$, $\beta_5$ and CD36. In contrast, in mature DCs [lane 2] no $\beta_5$, and much less CD36 sequences were seen, while $\beta_3$ sequences were comparable to that in immature cells. These data, while not quantitative, are consistent with the levels of protein expression observed by FACS® and suggests that phagocytic receptor expression in DCs may be regulated at a transcriptional level as mRNA expression of CD36 and $\beta_5$ is down regulated during maturation:

$\alpha_v\beta_5$ and CD36 mediate phagocytosis of apoptotic cells in immature DCs. To demonstrate a direct role for $\alpha_v\beta_5$ in the recognition of apoptotic cells by immature DCs, we performed the phagocytosis FACS® assay in the presence of antibodies specific for $\alpha_v\beta_5$ [FIG. 20]. In addition to the blocking observed using the monoclonal to $\alpha_v\beta_5$, blocking was also detected when using monoclonal antibodies to $\alpha_v$, $\beta_5$ and CD36. Blocking was not observed when isotype matched monoclonals specific for $\beta_1$, $\beta_3$ or the transferrin receptor, CD71. Note, control antibodies were chosen which recognized surface receptors present on the immature DC [FIG. 20A, Table 1]. Monoclonal antibodies were tested in doses ranging from 10–80 µg/ml [data not shown]. Maximal inhibition of phagocytosis of apoptotic cells was seen with mAbs specific for CD36, $\alpha_v$, and $\beta_5$ at 50 µg /ml. The inhibition of phagocytosis of apoptotic cells by DCs was specific. We were unable to block the uptake red fluorescent latex beads, a control particle, by DCs in the presence of these monoclonal antibodies [FIG. 20B]. By histogram analysis, DCs phagocytose 1–6 particles per cell. MAbs to $\alpha_v\beta_5$ or $\alpha_v$ did not alter the profile of these histogram plots [data not shown].

While some inhibition of phagocytosis was observed when using $\alpha_v\beta_3$ this may in part be due to transdominance

TABLE I

Receptor Profile of various Antigen Presenting Cells

| | Immature DC $ Day 7 | Mature DC # Day 11 | Monocytes ¥ Day 0 | Macrophages Δ Day 3 | Macrophages Δ Day 9 |
|---|---|---|---|---|---|
| CD8 * | 0 – 2 (3 ± 1) § | 0 – 3 (4 ± 1) | 0 – 1 (4 ± 1) | 0 – 5 (3 ± 1) | 1 – 2 (3 ± 1) |
| CD14 * | 1 – 10 (4 ± 1) | 0 – 6 (4 ± 1) | 83 – 97 (149 ± 90) | 67 – 98 (61 ± 20) | 49 – 90 (68 ± 48) |
| CD83 † | 8 – 43 (8 ± 4) | 73 – 99 (114 ± 15) | 0 – 1 (3 ± 1) | 4 – 19 (4 ± 2) | 2 – 14 (4 ± 2) |
| MHC I † | 99 – 100 (311 ± 93) | 96 – 100 (280 ± 69) | 99 – 100 (99 ± 38) | 97 – 99 (164 ± 24) | 95 – 100 (116 ± 18) |
| HLA-DR * | 88 – 100 (84 ± 35) | 98 – 99 (188 ± 40) | 94 – 99 (63 ± 9) | 97 – 99 (173 ± 34) | 5 – 89 (25 ± 27) |
| CD8 † | 3 – 9 (4 ± 1) | 2 – 8 (3 ± 1) | 0 – 2 (3 ± 1) | 1 – 4 (3 ± 0) | 1 – 5 (3 ± 1) |
| IgG2b † | 3 – 7 (3 ± 1) | 2 – 7 (3 ± 1) | 0 – 2 (3 ± 0) | 1 – 4 (3 ± 1) | 1 – 5 (3 ± 1) |
| CD36 † | 75 – 99 (75 ± 31) | 20 – 50 (9 ± 2) | 89 – 99 (62 ± 18) | 64 – 64 (69 ± 45) | 9 – 55 (15 ± 16) |
| $\alpha_v$ (CD51) † | 45 – 76 (14 ± 3) | 11 – 40 (9 ± 3) | 2 – 12 (4 ± 1) | 2 – 35 (6 ± 2) | 18 – 75 (10 ± 5) |
| $\beta_1$ (CD29) † | 99 – 100 (287 ± 57) | 84 – 100 (112 ± 28) | 95 – 100 (61 ± 33) | 83 – 100 (72 ± 23) | 68 – 99 (104 ± 29) |
| $\beta_3$ (CD61) † | 14 – 34 (7 ± 2) | 10 – 24 (6 ± 1) | 76 – 91 (40 ± 16) ∞ | 15 – 85 (14 ± 9) ∞ | 19 – 92 (16 ± 9) |
| $\beta_5$ † | 78 – 95 (30 ± 8) | 32 – 57 (11 ± 2) | 6 – 8 (5 ± 1) | 8 – 15 (7 ± 2) | 5 8 (3 ± 1) |
| $\alpha_v\beta_3$ (VnR) † | 22 – 28 (7 ± 1) | 14 – 30 (7 ± 2) | 4 – 8 (4 ± 1) | 7 – 27 (5 ± 2) | 19 – 68 (10 ± 4) |
| $\alpha_v\beta_5$ † | 81 – 90 (25 ± 5) | 12 – 53 (9 ± 3) | 1 – 14 (4 ± 1) | 0 – 11 (3 ± 1) | 6 – 15 (4 ± 1) |
| CD71 † | 75 – 99 (50 ± 29) | 75 – 94 (61 ± 27) | 3 – 7 (4 ± 0) | 14 – 30 (7 ± 2) | 58 – 81 (30 ± 7) |
| Mannose Receptor † | 99 – 100 (272 ± 68) | 38 – 80 (26 ± 11) | 2 – 7 (4 ± 0) | 24 – 63 (13 ± 8) | 48 – 95 (34 ± 20) |

\* PE-conjugated.
† Unconjugated antibody.
§ Results are expressed as range of values, calculated as percentage of positive cells as compared to an isotype matched control antimbody.
Values in parentheses indicate the average of geometric mean fluorescence intensities of the various samples.
∞ The $\beta_3$ expression in the monocytes and day 3 macrophages does not match the $\alpha_v\beta_3$ expression due to contaminating platelets which stuck to the cells during isolation, as determined by staining with anti-CD41, data not shown.
¥ n = 4.
Δ n = 5.
n = 6.
$ n = 7.

and/or the effect on the pool of free $\alpha_v$ (130). For example, anti-$\alpha_v\beta_3$ antibodies suppress the intracellular signaling of the $\alpha_5\beta_1$ integrin (131). Alternatively, $\alpha_v\beta_3$ and $\alpha_v\beta_5$ may be working cooperatively in the immature DCs. We therefore tested combinations of anti-$\alpha_v\beta_3$ and anti-$\alpha_v\beta_5$, but did not observe an increase in the inhibition of phagocytosis. The low receptor density of $\alpha_v\beta_3$ on DCs [average MFI of 7+/−2, Table 1] also makes it unlikely that this integrin heterodimer is involved in the engulfment of apoptotic cells by immature DCs.

Our data do not exclude a role for other receptors in the phagocytosis of apoptotic cells e.g. the putative phosphatidylserine receptor or the lectin receptor (100). In fact, other receptors are probably involved as blocking observed did not exceed 60%, even when combinations of all relevant mAbs were tested [data not shown]. CD14 is unlikely to be involved in the DC's engulfment of apoptotic cells, as DCs do not express this receptor [Table 1]. In macrophages, phagocytosis of apoptotic cells was inhibited by antibodies to $\alpha_v$, $\beta_3$, $\alpha_v\beta_3$ and CD36 but not by antibodies to $\beta_1$, $\beta_5$ or $\alpha_v\beta_5$ [data not shown]. This correlates with published data (101,128).

Cross-presentation of antigens to CTLs appears to have two critical features. It is mediated by DCs and apoptotic cells are the preferred source of antigen (102). The requisite stage of DC development for the acquisition of apoptotic cells is the immature phase. In fact, immature DCs, are 4–5 times more efficient than mature DCs in phagocytosis, a feature which also correlates with their ability to cross-present antigen. This exogenous pathway for class I MHC loading is highly effective: relatively few apoptotic cells [ratio of 1 per 10 DCs] are needed to charge the DCs as efficiently as the live replicating virus; exposure of 3–12 hours is sufficient for generating a peptide-MHC complex that is capable of activating CTLs; and it is relatively indiscriminate, as the cellular source can be allogeneic cells or xenogeneic cells (102,132). We believe our earlier studies with mature DCs are explained by the fact that our cell populations were asynchronous and that only by sorting these cells have the differences become apparent. Based on the findings presented here, we suggest that the peripheral tissue DC, exemplified by the immature DC, has an additional important role. It is responsible for phagocytosing cells within tissues which undergo apoptosis [e.g. secondary to viral infection; during normal cell turnover] and migrating to the draining lymph nodes where appropriate T cells are engaged. This pathway may be employed for stimulating or tolerizing CTLs and can account for the in vivo observations of cross-priming of tumor and viral antigens (104,133) and cross-tolerance of self proteins (105,134) in their requirement for a bone marrow derived APC.

A sharp distinction was also demonstrated between immature DCs and macrophages in the handling of apoptotic material. While macrophages are more efficient at phagocytosing apoptotic cells than immature DCs, they fail to induce virus-specific CTLs (102). In fact, they cannot even generate effective levels of peptide/MHC I complexes. In a short-term assay, influenza-specific CTLs could not kill macrophages co-cultured with apoptotic cells. Therefore, macrophages degrade rather than cross-present the ingested apoptotic cells.

Additional evidence exists that macrophages process apoptotic cells differently from DCs, and prevent an immune response. Two groups have demonstrated that phagocytosis of apoptotic cells suppresses a subsequent inflammatory response to LPS stimulation. The macrophage's cytokine profile is skewed toward the synthesis of IL-10, IL-13 and TGF-$\beta$, while the production of proinflammatory cytokines such as TNF-$\alpha$, IL-1$\beta$, and IL-12 is down-modulated (136, 137). Therefore, the resolution of inflammation is dependant on at least two pathways for removal of apoptotic cells: via macrophages which subvert and suppress proinflammatory responses; and via DCs, which stimulate T cell responses that clear pathogens responsible for the induction of the apoptotic death.

The $\alpha_v\beta_5$ integrin receptor may be pivotal in the distinctive handling of apoptotic cells by immature DCs versus. macrophages in that it's expression is restricted to the former. We suggest that the unique profile of receptors expressed by immature DCs affects trafficking of phagocytosed apoptotic cells, and consequently facilitates cross-presentation. We have previously shown that $NH_4Cl$ inhibits the DCs ability to process antigen derived from apoptotic cells, suggesting that processing in an acidic vesicle [e.g. CIIVs or MIICs] is required (102,132). Indeed, class I MHC may interact with processed antigens in such a compartment, as MHC I molecules have been described in association with invariant chain (138), and can recycle from the cell surface to class II vesicles (139). Additionally, there may be as yet undescribed routes whereby antigens within vesicles can enter the classical endogenous pathway as described recently for antigens derived from the ER (140).

$\alpha_v\beta_5$ and $\alpha_v\beta_3$ have both been described to be important in angiogenesis, cell adhesion, migration and now in their ability to phagocytose apoptotic cells. $\alpha_v\beta_3$ is critical in the phagocytosis of apoptotic cells in macrophages, where it acts in a cooperative way with CD36 and thrombospondin [TSP], collectively forming a 'molecular bridge' (142). Recently, it was reported that $\alpha_v\beta_5$ but not $\alpha_v\beta_3$ is critical for the engulfment of rod outer segments [ROS] by CD36$^+$ retinal pigment epithelial cells (143,144). This phagocytic system is also inhibited by anti-CD36 antibodies, suggesting that $\alpha_v\beta_5$, like $\alpha_v\beta_3$, might cooperate with CD36. Taken together with our observations, TSP, or possibly other soluble factors, may serve to bridge CD36, $\alpha_v\beta_5$ and the apoptotic cell.

Although similarities in function exist, $\alpha_v\beta_5$ can be distinguished from $\alpha_v\beta_3$ in its use of various ligands [e.g. VEGF vs. bFGF]; by the requirements for activation; and by the intracellular signaling pathways [e.g. indirect activation of PKC] (50). Also significant is the fact that the cytoplasmic domains of the two $\beta$ chains are the portions which show the most considerable diversity (51). Thus, it is possible that the distinct use of the $\alpha_v\beta_5$ vs. $\alpha_v\beta_3$ integrin receptors might account for the specialized functions of DCs in the route by which apoptotic material is trafficked and presented. In other words, differential expression of $\alpha_v\beta_5$ may be responsible for the DCs ability to cross-present antigenic material derived from apoptotic cells, whereas macrophages scavenge and degrade such material.

EXAMPLE 8

Inhibition of Integrin Inhibited Engulfment of Apoptotic Cells

We have shown in the previous Example that engulfment of apoptotic cells by immature DCs is a receptor mediated phagocytic event, as it is inhibited by EDTA, Cytochalasin D and low temperature (see Example 7)(147). Immature DCs express little $\alpha_v\beta_3$, instead they employ an alternate $\alpha_v$ heterodimer, the $\alpha_v\beta_5$ integrin receptor, for the efficient internalization of apoptotic cells. As is the case in the macrophage receptor complex, $\alpha_v\beta_3$/CD36, we believe that the $\alpha_v\beta_5$ integrin receptor works in concert with CD36. The expression of this receptor pair is restricted to the immature DC and upon maturation, CD36 and $\alpha_v\beta_5$ protein expression and their mRNA expression are both down regulated. This expression pattern fits what is known about DC biology—the immature cell is involved in antigen capture, while the mature stage is characterized by poor antigen acquisition, but instead is efficient at activating T cells.

In Example 7, we demonstrated that the uptake of apoptotic human monocytes, HeLa cells, and a murine macrophage cells line (RAW) by immature DCs are all inhibited by monoclonal antibodies specific for $\alpha_v\beta_5$, $\alpha_v$, $\beta_5$ and CD36. While we do not have direct evidence for the $\alpha_v\beta_5$/CD36 interaction, we know that addition of blocking antibodies for both receptors to DCs/apoptotic cells co-cultures does not result in increased inhibition. This suggested to us that these two receptors might be working in concert. Maximal inhibition achieved in the in vitro phagocytosis assay was never greater that 60%, suggesting that additional receptors are involved. Candidates include, the complement receptors CR3 and CR4, scavenger receptor A, a putative lectin receptor (possibly DEC-205), and a still undefined phosphatidylserine receptor (Reviewed in (149, 150)).

To better define the $\alpha_v\beta_5$/CD36 receptor complex on immature DCs, we have begun to search for a DC-restricted bridging molecule as it is unlikely that TSP-1 is the soluble factor involved in the $\alpha_v\beta_5$/CD36 receptor complex. Notably, neither the addition of antibodies specific for TSP-1, nor the addition of purified TSP to DC/apoptotic cell co-cultures has an inhibitory effect (data not shown). In contrast, both are known to inhibit engagement with CD36 on macrophages, thus blocking the phagocytosis of apoptotic cells. Additionally, we have begun to investigate the role for IAP-1 in the activation of the $\alpha_v\beta_5$ integrin.

Based on the data described herein regarding the characteristics of a specific molecular bridge between apoptotic cells and DCs we believe that Lactadherin, a major glycoprotein of the human milk fat globule membrane, (151–153) has several properties which suggest it may be a component of such a molecular bridge. Lactadherin has many of the properties required for acting as a molecular bridge between the immature DC and the apoptotic cell as milk fat globules (MFGs) and apoptotic cells share much in common. The membrane surrounding the MFG has the same orientation as the membrane of an apoptotic body/bleb (the outer leaflet of both is topologically identical to the plasma membrane); the external leaflet of the membrane encapsulating the droplet contains PS (likely due to a lack of flippase activity inherent to the MFG); and oligosaccharides comprised of fucose, galactose, N-acetylglucosamine and N-acetylgalactosamine (many of the same carbohydrate motifs found on the surface of dying cells) (152–154). The milk fat droplets are secreted from the lactating epithelial cells by a process of encapsulation in plasma membrane and is subsequently engulfed by the gut epithelium of the nursing child (155). Indeed, the characteristics which make Lactadherin successful at bridging the MFG with the gut epithelium are similar to those which are likely facilitating uptake of the apoptotic cells by the DC.

Supporting data: A role for IAP-1.

Another proposed factor involved in the $\alpha_v\beta_5$/CD36/Lactadherin complex is integrin associated protein-1 (IAP-1). IAP-1 is involved in the activation of the $\alpha_v\beta_3$/CD36/TSP-1 complex on macrophages. IAP-1 is expressed on virtually all cells; it is present on immature DCs (data not shown); and likely interacts with other $\alpha_v$ integrins as IAP-1 and $\beta_5$ have been co-immunoprecipitated (195). To test the hypothesis that IAP-1 is responsible for the activation of the $\alpha_v\beta_5$/CD36 complex on immature DCs, blocking studies with monoclonal antibodies and pertussis toxin (PT) were performed—we tested the effect of these factors on the phagocytosis of apoptotic cells by immature DCs (see Example 7 for experimental details of phagocytosis assay).

Antibodies specific for IAP-1 (clone B6H12, Chemicon International Inc.) inhibited the phagocytosis of apoptotic cells, however the blocking observed was significantly less than that observed when using anti-ad antibodies (TABLE II). PT, the major virulence factor of Bordetella pertussis inhibits heterotrimeric $G_i$-proteins, also blocked the phagocytosis of apoptotic cells by immature DCs (TABLE II).

TABLE II

Inhibitors of Phagocytosis*

| Added to Immature DC/ Apoptotic cell coculture | Percent Inhibition (Std Dev.) |
|---|---|
| anti-CD8 | 0 (n/a) |
| anti-$\alpha_v$ | 46.5 (0.5) |
| anti-IAP-1 | 27.8 (3.5) |
| LB 40 μM† | 0 (n/a) |
| LB 10 μM | 0 (n/a) |
| LA 40 μM | 41.5 (1.5) |
| LA 10 μM | 14 (8) |
| DMSO | 0 (n/a) |
| Herb 18 μM§ | 66.5 (2.5) |
| Herb 9 μM | 49 (2) |
| Herb 1.8 μM | 6.5 (2.5) |
| PT200 μg/ml∞ | 37.5 (4.5) |
| PT 50 μg/ml | 19 (10) |
| CC 12 μM¤ | 4 (2) |

*Results are expressed as averages of 2–4 experiments with values indicating percent inhibition of phagocytosis of apoptotic cells as compared to respective control wells. Conrols were cocultures treated with anti-CD8, Lavendustin B (the inactive analog of Lavendustin A), or DMSO alone. Values in parenthesis indicate standard deviation.
†Lavendustin B (LB) and Lavendustin A (LA). LA is a cell-permeable inhibitor of protein tyrosine kinase activity but has little effect on protein kinase A or protein kinase C.
§Herbamycin A is a potent cell-permeable protein tyrosine kinase inhibitor and inhibits PDGF-induced phospholipase D activation ($IC_{50}$ = 8 μg/ml) in a dose dependant manner.
∞Pertussis Toxin (PT) is an inhibitor of the heterotrimeric G-protein $G_1$.
¤Chelethrine chloride (CC) is a cell-permeable inhibitor of protein kinase C ($IC_{50}$ = 660 nM).

Taken together, our data suggests that $\alpha_v\beta_5$/CD36/IAP-1/Lactadherin receptor complex on immature DCs may be responsible for the efficient engulfment of apoptotic cells. Similar, but as yet unidentified factors could also serve to enhance the uptake of apoptotic cells (or fragments thereof) in our antigen delivery system.

EXAMPLE 9

Consequences of Cell Death: Exposure to Necrotic but not Apoptotic Cells Induces the Maturation of Immunostimulatory Dendritic Cells Materials & Methods Preparation of DCs. DCs were prepared as previously described (171–173). In brief, DCs were generated from T cell depleted PBMCs by culturing cells for 5–6 days in the presence of 1,000 U/ml granulocyte and macrophage colony-stimulating factor [GM-CSF, Immunex] and 1,000 U/ml IL-4 [Schering-Plough Corp. Union, N.J.]. RPMI 1640 supplemented with 20 μg/ml gentamicin, 10 mM HEPES, [GIBCO] and 1% autologous plasma [heparinized] was used for cell culture. Cultures were supplemented with cytokines on days 2 and 4. On day 5–6 nonadherent immature DCs were collected and transferred to new six well plates. Mature DCs were generated by the addition of 50% v/v monocyte conditioned medium [MCM] on the day of transfer and harvested on days 8–9.

Induction of Apoptosis and Necrosis. 293 cells were dyed red with PKH 26 according to the manufacturer's protocol [Sigma Biosciences, St. Louis, USA]. UV-triggered apoptosis was induced using a 60UVB lamp [Derma Control Inc]. Cells were incubated for 6 hours following irradiation to allow the cells to undergo apoptosis. Necrosis was achieved via repeated freezing and thawing. Immature DCs were dyed green with PKH 67 and then co-cultured with the apoptotic and necrotic cells for 3 hours at 4° or 37C°. Phagocytosis of apoptotic and necrotic cells by immature DCs was defined by the percentage of double positive cells by FACS-Analysis as previously described (176). UV-triggered apoptosis was also induced using a 60 mJ UVB lamp [Derma Control Inc.], calibrated to provide 2 mJ/cm$^2$/sec. Necrosis was achieved via repeated freeze [−80C° C.] thawing [+37° C.]. Necrotic cells were trypan blue positive and demonstrated a distorted or fragmented morphology.

Cell lines. The following cell lines were used: Human cell lines consisted of EBV transformed B-lymphocyte cell lines [B-LCL cells], melanoma cells [SK29 cells], and kidney adenocarcinoma cells [293 cells] and were cultured in RPMI supplemented with 10% FCS. Mouse cell lines [B16 melanoma cells, L-cells, RAW cells, 3T3 cells] were grown in DMEM supplemented with 10% FCS.

Monoclonal antibodies. Monoclonal antibodies [mAbs] to the following antigens were used. CD83 [Immunotech, Coulter, Marseille, France] and DC-LAMP [generously provided by Dr. S. Lebecque, Schering Plough, Dardilly, France] are markers expressed primarily by mature DCs. CD86, HLA-DR, CD40, CD25, CD8, CD14 were obtained from Becton-Dickinson [Mountainview, Calif.]. Isotype control mAbs included IgG1, IgG2a and IgG2b [Immunotech, Coulter, Marseille, France]. The secondary antibody was PE-conjugated Fab'$_2$ goat anti-mouse IgG heavy and light chain [Jackson, ImmunoResearch, Laboratories, Inc., Baltimore, USA]. The DC cell populations were phenotyped with the panel of mAbs listed above and analyzed on a FACScan [Becton Dickinson, Mountain View, Calif.]. For intracellular staining cells were first fixed in 1% paraformaldehyde and then permeabilized with 0.5% saponin before incubation with the primary antibody.

Co-culture of apoptotic or necrotic cells with immature DCs. Apoptotic or necrotic cell lines were added at various ratios to day 5 or 6 immature DCs. After 48 hours of coculture the DCs were assayed for their T cell stimulatory capacity. For the superantigen dependent assay DCs were irradiated with 3000 rad prior to addition to syngeneic T cells in the presence of 0.1 ng/ml SEA. After 3 days, 4 µci/ml $^3$H-thymidine was added for 16 hours. We observed background proliferation in 5 day co-cultures, of immature DCs and allogeneic T cells in the MLR, probably because of some DC maturation as a result of DC-T cell interactions. To avoid this, we fixed immature DCs after exposure to dying cells with 1% paraformaldehyde for 30 min on ice, washed extensively and added them in graded doses to allogeneic T cells. After 4 days, 4 uci/ml $^3$H-thymidine was added for 16 hours. Immature and MCM matured DCs served as controls.

Results

The immune system has to contend with two types of cell death and their consequences. Necrosis, characterized by cell fragmentation resulting from severe and sudden injury, leads to the release of toxic intracellular contents which may induce inflammation (156). Apoptosis, an energy dependent and synchronized event, is considered non-inflammatory due to rapid scavenging by macrophages (156–158). Necrotic and apoptotic cells are also phagocytosed by dendritic cells, potent initiators of immunity, which induce T cell responses to antigens derived from these dying cells (159–161). Uptake is restricted to the immature stage of development when DCs are well equipped to acquire antigen but express low levels of the requisite MHC and costimulatory molecules needed for T cell stimulation (159). Upon receipt of a maturation signal, DCs downregulate antigen acquisition, express higher levels of costimulatory and MHC molecules and become stably differentiated to activate resting T cells. Maturation can be triggered by multiple stimuli including LPS, contact allergens, bacteria and viruses, cell products [monocyte conditioned medium-MCM, TNFα, IL-1β, PGE$_2$, IFN-alpha (162–168)] and signalling molecules [CD 40L (169–170)]. Since it is the immature DC that captures antigen most efficiently, we investigated whether the uptake of dead or dying cells could initiate immunity by inducing DC maturation.

To generate immature DCs, we cultured freshly isolated blood monocytes in GM-CSF and IL-4 for 6 days. These cells are characterized by low levels of HLA and co-stimulatory molecules [CD40, CD86 (159)] and the DC restricted, maturation associated markers CD83 and DC-LAMP [lysosomal associated membrane glycoprotein] (174). We first verified that immature DCs phagocytosed necrotic cells comparably to apoptotic cells (175). A FACS assay was employed where green PKH26-GL labeled DCs are visually assessed for their ability to take up red PKH67-GL labeled apoptotic or necrotic tumor cells [kidney adenocarcinoma, 293 cells] at a ratio of 1:1 (176). Over 40% of immature DCs phagocytosed either apoptotic or necrotic cells within 3 hours [FIG. 21 A,B,C]. Uptake was profoundly reduced when dead cells were co-cultured with DCs at 4° C., indicating that cells or cell fragments were being bound specifically. As expected, mature DCs displayed poor phagocytic activity for either apoptotic or necrotic cells [FIG. 21C]. As a control for the effects of phagocytosis, we added FITC-labeled latex beads to immature DCs which were then cultured for 48 hrs in the presence or absence of MCM, the latter to induce maturation. Uptake of latex beads by itself did not induce maturation, as monitored by surface CD83 expression, and furthermore did not inhibit maturation via MCM [FIG. 21 D,E (177)].

We next monitored the effects of dying cells on the maturation of DCs. A panel of human cell lines was tested including a melanoma cell line [SK29 cells], kidney adenocarcinoma cells [293 cells] and EBV transformed B-lymphocyte cell lines [B-LCL] [FIG. 22 A,]. Again a 48 hr co-culture was carried out at different ratios of dying cells to DCs [1:5 to 1:2], after which the DCs were collected, stained for markers indicative of maturation, and analyzed on a FACScan®. Exposure to necrotic cells, but not apoptotic cells, induced the expression of the maturation associated markers CD83 and DC-LAMP in a large percentage of DCs [FIG. 22 A,B,C] and upregulated both co-stimulatory [CD86] and HLA molecules [FIG. 22 D,E]. Furthermore, CD40 levels almost doubled following exposure to necrotic cells [FIG. 22]. The induction of maturation was irreversible as DCs did not revert to an immature phenotype in culture. Necrotic mouse cell lines, including L-cells, 3T3 cells and B16 melanoma cells, also induced the maturation of DCs. Interestingly, when we added an excess of apoptotic cells to DCs at ratios of 5:1 or 10:1 there was extensive DC death [data not shown]. In contrast, this dose of cells was recently reported to induce maturation of a murine DC line (178), but the apoptotic cells were cultured for 16 hrs prior to addition to DCs. It is possible that the apoptotic cells underwent secondary necrosis, and the latter induced maturation.

To define the nature of factors in necrotic cells that were responsible for inducing maturation, we collected supernatants from necrotic and apoptotic cell lines, filtered them through a 0.45 micron filter and added these to immature DC cultures. Supernatants from necrotic but not apoptotic cells induced maturation [FIG. 22 F]. Obvious candidates for maturation such as TNF-α and IL-1β were not detectable by ELISA in the supernatants [not shown].

Mature DCs are potent stimulators of T cells, the most straightforward assays being the induction of allogeneic T cell proliferation in the mixed leukocyte reaction [MLR] and superantigen dependent T cell proliferation (179, 180). After a 48 hour exposure to dying cells or their respective supernatants, DCs were washed, and added in graded doses to 200,000 allogeneic or syngeneic T cells, in the latter case together with 0.1 ng/ml staphylococcus enterotoxin A [SEA]. Strong stimulation of allogeneic and superantigen stimulated syngeneic T cells was observed with DCs that had been matured with necrotic cells, their respective supernatants or with MCM [FIG. 23 A,B]. In contrast, exposure to apoptotic cells did not induce MLR stimulatory activity or superantigen dependent syngeneic proliferation above the low background in the absence of MCM [FIG. 23 A,B]. The $^3$H-thymidine uptake data was confirmed by analysis of T cell size on the FACS® scan. In response to mature DCs [matured with MCM or with exposure to necrotic cells], >30% of the CD3+T cells in the MLR were blasts [high forward light scattering], whereas immature DCs [no MCM, or exposure to apoptotic cells] induced <5% blast transformation [not shown]. Importantly, when DCs were exposed to a mixture of apoptotic and necrotic cells, they induced similar increases in T cell stimulation as DCs cultured with necrotic cells or their supernatants [data not shown]. Furthermore DCs exposed in parallel to apoptotic cells and MCM heightened T cell responses to the same extent as DCs matured with MCM. These experiments indicated that ingestion of apoptotic cells did not inhibit DC maturation or function. This contrasts with recently published data showing that phagocytosis of apoptotic cells induces immunosuppressive and anti-inflammatory effects in macrophages [e.g. release of IL-10 and PGE$_2$ after LPS stimulation] and that apoptotic cells themselves can be sources of factors [e.g. IL-10] that skew the immune response (182–183).

While a role for macrophages in the phagocytic clearance of both apoptotic and necrotic cells is well known, there is little information on how DCs respond to dying cells. We find striking differences in the handling of dying, transformed cell lines depending on the mechanism of cell death. Necrotic cells selectively induce maturation of DCs. We would predict that in vivo, uptake of necrotic tumor cells would lead to the initiation of T cell responses to antigens processed by the DCs. These responses are likely to be CD4+ rather than CD8+, as antigens derived from necrotic cells do not induce CTLs, at least in vitro (160). Phagocytosis of apoptotic cells by DCs failed to induce maturation, the consequences of which may be the induction of tolerance to self or tumor antigens (184–186). Phagocytosis of apoptotic cells, however, may lead to T cell immunity if followed by a maturation signal. We have shown that DCs phagocytose apoptotic cells and present antigens [e.g. viral and tumor antigens] from these sources to both CD4+ and CD8+ T cells. See, Examples 1–5. Given that phagocytosis of apoptotic cells does not mature DCs, signals provided by necrotic cells in the enviroment, such as cytokines [e.g. TNF-α, IL-1β, IFN-α released by virus infected cells], inflammatory products [e.g. LPS, bacterial cell walls] and CD4+ T cells [such as CD40-L/CD40 interactions (169, 170)] would be required to mature the DCs, thus allowing for the full activation of T cells. In fact in in vivo animal models of cross-priming and cross-tolerance, induction of CTLs requires CD4$^+$ help [(184, 187–189) and data in vitro not shown].

REFERENCES

1. Koup, R. A., C. A. Pikora, K. Luzuriaga, D. B. Brettler, E. S. Day, G. P. Mazzara, and J. L. Sullivan, 1991 *J. Exp. Med.* 174:1593–1600.

2. Carmichael, A, X. Jin, P. Sissons, and L. Borysiewicz, 1993, *J. Exp. Med.* 177:249–256.

3. Johnson, R. P., A. Trocha, T. M. Buchanan and B. D. Walker, 1992, *J. Exp. Med.* 175:961–971.

4. McHichael, A. J. and B. A. Askonas, 1978, *Eur. J. Immunol.*, 8:705–711.

5. Hill, A. V. S., J. Elvin, A. C. Willis, M. Aidoo, C. E. M. Allsopp, F. M. Gotch, X. M. Gao, M., Takiguchi, B. M. Greenwood, A. R. M. Townsend, A. J. McHichael, and H. C. Whittle, 1992, *Nature* 360:434–439.

6. Riddell, S. R., K. S. Watanabe, J. M. Goodrich, C. R. Li, M. E. Agha, and P. D. Greenberg, 1992 *Science* 257: 238–241.

7. Khanna, R. S. R. Burrows, A. Neisig, J. Neefjes, D. J. Moss and S. L. Silins, 1997, *J. Virol.* 71(10):7429–35.

8. Van Der Brogen, P., C. Traverari, P. Chomez, C. Lurquin, E. De Plaen, B. Van Deneynde, A. Knuth, and T. Boon, 1991, *Science* 254:1643–1647.

9. Young, J. W. and R. M. Steinman, 1990, *J. Exp. Med.*, 171:1315–1332.

10. Steinman, R. M., 1991, *Ann. Rev. Immunol.*, 9:271–296.

11. Jondal, M., R. Schirmbeck, and J. Reiman, 1996, *Immunity*, 5:295–302.

12. Kuzu, H., Y, Kuzu, H. Zaghouani, and C. Bona, 1993, *Eur. J. Immunol.*, 23:1397–1400.

13. Aichele, P., H. Hengartner, R. M. Zinkernagel, and M. Schulz, 1990, *J. Exp. Med.*, 171:1815–1820.

14. Gao, X-M., B. Zheng, F. Y. Liew, S. Brett, and J. Tite, 1991, *J. Immunol.*, 147:3268–3273.

15. Schulz, M., R. M. Zinkernagel, and H. Hengartner, 1991, *Proc. Natl. Acad. Sci. USA*, 88:991–993.

16. Moore, M. W., F. R. Carbone, and M. J. Brevan, 1988, *Cell*, 54:777–785.

17. Zhou, F. and L. Huang, 1994, *Immunomethods*, 4:229–235.

18. Nair, S., F. Zhou, R. Reddy, L. Huang, and B. T. Rouse, 1992, *J. Exp. Med.*, 175:609–612.

19. Rubartelli, A. A. Poggi, and M. F. Zocchi, 1997, *Eur. J. Immunol.*, 27:1893–1900.

20. Cohen, G. M., Biochen, J. (1997) 326:1–16.

21. Miller, D. K. 1997 Sem. Immunol 5:35–49.

22. Wyllie, A. H. 1997 Eur. J. Cell. Biol. 73:189–197.

23. Suss, G., and K. Shortman 1996 J. Exp. Med 183: 1789–1796.

24. Inaba, K., M. Pack, M. Inaba, H. Sakuta, F. Isdell, and R. M. Steinman. 1997. Exp. Med. 5:665–672.

25. Hemmels, M. T., & Ploegh, H. *Annual Review of Biochemistry* 64, 463–491 (1995).

26. Watts, C., *Annu. Rev. Immunol.* 15, 821–850 (1997).

27. Jondal, M., Schirmbeck, R. & Reimann, *J. Immun.*, 5, 295–302 (1996).

28. Bevan, M. J. *J. Exp. Med.*, 143, 1283–1288 (1976).

29. Kovacsovics-Bankowski, M. & Rock, K. L. *Science*, 267, 243–246 (1995).

30. Huang, A. Y. C., Golumbeck, P., Ahmadzedah, M., Jaffee, E., Pardoll, D. & Levitsky, H. *Science* 264, 961–965 (1994).

31. Suto, R. & Srivastava, P. K. *Science*, 269, 1585–1588 (1995).

32. Norbury, C. C., Chambers, B. J., Prescott, A. R., Ljunggren, H.-G. & Watts, C. *Eur. J. Immunol.* 27, 280–288 (1997).

33. Pfeifer, J. D., Wick, M. J. Roberts, R. L. Findlay, K., Normark, S. J. & Harding, C. V. *Nature* 361, 359–362 (1993).

34. Reis e Sousa, C. & Germain, R. N., *J. Exp. Med.*, 182, 841–851 (1995).

35. Kurts, C., Heath, W. R., Carbone, F. R., Allison, J. Miller, J. F. A. P. & Kosaka, H. *J. Exp. Med.*, 184, 923–930 (1996).

36. Kurts, C., Kosaka, H., Carbone, F. R., Miller, J. F. A. P. & Heath, W. R. *J. Exp. Med.*, 186, 239–245 (1997).

37. Bhardwaj, N., Bender, A., Gonzalez, N., Bui, L. K., Garrett, M. C. & Steinman, R. M. *J. Clin. Invest.* 94, 797–807 (1994).

38. Bender, A., Albert, M., Reddy, A., et al., *Immunobiology, in press* (1997).

39. Bender, A., Bui, L. K., Feldman, M. A. V., Larsson, M. & Bhardwaj, N. *J. Exp. Med.*, 182, 1663–1671 (1995).

40. Fesq, H., Bacher, M., Nain, M. & Gensa, D. *Immunobiol.* 190, 175–182 (1994).

41. Hofmann, P., Sprenger, H., Kaufman, A., et al. *J. Leuk. Biol.*, 612, 408–414 (1997).

42. Bender, A., Sapp, M., Schuler, G., Steinman, R. M. & Bhardwaj, N. *J. Immunol. Methods* 196, 121–135 (1996).

43. Romani, N., Reider, D., Heuer, M., et al. *J. Immunol. Methods* 196, 137–151 (1996).

44. Bender, A., Amann, U., Jager, R., Nain, M. & Gemsa, D. *J. Immunol*, 151, 5416–5424 (1993).

45. Hirst, G. K., *J. Exp. Med.*, 75, 49–64 (1942).

46. Badley, A. D., Dockrell, D., Simpson, M., et al., *J. Exp. Med.* 185, 55–64 (1997).

47. Casciola-Rosen, J., Anhalt, G. & Rosen, A. *J. Exp. Med.* 179, 1317–1330 (1994).

48. Bennett, S. R. M., Carbone, F. R., Karamalis, F. Miller, J. J. A. P. & Heath, W. R. *J. Exp. Med.* 186, 65–70 (1997).

49. Sugita, M. & Brenner, M. B. *Journal of biological chemistry* 270, 1443–1448 (1995).

50. Yewdell, J. W. & Bennink, J. R. *Science* 268, 726–731 (1995).

51. Fenteany, G., Standaert, R. F., Lane, W. S., Choi, S., Corey, E. J. & Schreiber, S. L. *Science* 268, 726–731 (1995).

52. Rubartelli, A., Poggi, A. & Zocchi, M. R. *Eur. J. Immunol.* 27, 1893–1900 (1997).

53. Shen, Z., Reznikoff, G., Droanoff, G. & Rock, K. L. *J. Immunol.* 158, 2723–2730 (1997).

54. Paglia, P., Choidoni, C., Rodolfo, M. & Colombo, M. P. *J. Exp. Med.* 183, 317–322 (1996).

55. Bachmann, M. F., Lutz, M. B., Layton, G. T., et al. *Eur. J. Immunol.*, 26, 1–7 (1996).

56. Fossum, S. & Rolstad, B. *Eur. J. Immunol.* 16, 440–450 (1986).

57. Bevan, M. J. *Journal of Immunology* 118, 1370–1374 (1977).

58. Arnold, D., Faath, S., Rammensee, H.-G. & Schild, H. *J. Exp. Med.* 182, 885–889 (1995).

59. Gotch, F., McMichael, A. & Rothbard, J. *J. Exp. Med.*, 182, 885–889 (1995).

60. Gotch, F., Rothbard, J., Howland, K., Townsend, A. & McMichael, A. *Nature* 326, 881 (1987).

61. Thornberry, N. A., & et al. *Nature* 356, 768–774 (1992).

62. De Panfililis, G., Manara, G. C. & Ferrari, C. *Journal of Investigative Dermatology* 87, (1986).

63. Huang, A. Y. C., Golumbek, P., Ahmadzadeh, M., Jaffee, E., Pardoll, D. & Levitsky, H. Role of bone marrow-derived cells in presenting MHC class I-restricted tumor antigens. *Science* 264, 961–965 (1994).

64. Auchincloss, H., Jr. & Sultan, H. Antigen processing and presentation in transplantation. *Curr. Opin. Imumunol.* 8, 681–687 (1996).

65. Bevan, M. J. Cross-priming for a secondary cytotoxic response to minor H antigens with H-2 congenic cells which do not cross-react in the cytotoxic assay. *J. Exp. Med.* 143, 1283–1288 (1976).

66. Liu, Z., Colovai, A. I., Tugulea, S., et al. Indirect recognition of donor HLA-DR peptides in organ allograft rejection. *J. Clin. Invest.* 98, 1150–1157 (1996).

67. Benichou, G., Takizawa, P. A., Olson, C. A., McMillan, M. & Sercarz, E. E. Donor major histocompatibility complex [MHC] peptides are presented by recipient MHC molecules during graft rejection. *J. Exp. Med.* 175, 305–308 (1992).

68. Fangmann, J., Dalchau, R. & Fabre, J. W. Rejection of skin allografts by indirect allorecognition of donor class I major histocompatibility complex peptides. *J. Exp. Med.* 175, 1521–1529 (1992).

69. Liu, Z., Sun, Y. K., Xi, Y. P., Harris, P. & Suciu-Foca, N. T cell recognition of self-human histocompatibility leukocyte antigens [HLA]-DR peptides in context of syngeneic HLA-DR molecules. *J. Exp. Med.* 175 1663–1668 (1992).

70. Moses, R. D., Pierson III, R. N., Winn, H. J. & Auchincloss Jr., H. Xenogeneic proliferation and lymphokine production are dependent on CD4+ helper T cells and self antigen-presenting cells in the mouse. *J. Exp. Med.* 172, 567–575 (1990).

71. Kurts, C., Heath, W. R., Carbone, F. R., Allison, J., Miller, J. F. A. P. & Kosaka, H. Constitutive class I-restricted exogenous presentation of self antigens in vivo. *J. Exp. Med.* 184, 923–930 (1996).

72. Kurts, C., Kosaka, H., Carbone, F. R., Miller, J. F. A. P. & Heath, W. R. Class I-restricted cross-presentation of exogenous self antigens leads to deletion of autoreactive CD8+ T cells. *J. Exp. Med.* 186, 239–245 (1997).

73. Forster, I. & Lieberam, I. Peripheral tolerance of CD4 T cells following local activation in adolescent mice. *Eur. J. Immunol.* 26, 3194–3202 (1996).

74. Albert, M. L., Sauter, B. & Bhardwaj, N. Dendritic cells acquire antigen from apoptotic cells and induce class I-restricted CTLs. *Nature* In Press, (1998).

75. Rudensky, A. Y., Rath, S., Preston-Hurlburt, P., Murphy, D. B. & Janeway Jr., C A. On the complexity of self. *Nature* 353, 660–662 (1991).

76. Murphy, D. B., Rath, S., Pizzo, E., et al. Monoclonal antibody detection of a major self peptide. *J. Immunol.* 148, 3483–3491 (1992).

77. Chicz, R. M., Urban, R. G., Lane, W. S., et al. Predominant naturally processed peptides bound to HLA-DR1 are derived from MHC-related molecules and are heterogeneous in size. *Nature* 358, 764–768 (1992).

78. Hunt, D. F., Michel, H., Dickinson, T. A., et al. Peptides presented to the immune system by the murine class II major histocompatibility complex molecule I-Ad. *Science* 256, 1817–1820 (1992).

79. Inaba, K., Inaba, M., Naito, M. & Steinman, R. M. Dendritic cell progenitors phagocytose particulates, including Bacillus Calmette-Guerin organisms, and sensitize mice to mycobacterial antigens in vivo. *J. Exp. Med.* 178, 479–488 (1993).

80. Nussenzweig, M. C., Steinman, R. M., Unkeless, J. C., Witmer, M.-D., Gutchinov, B. & Cohn, Z. A. Studies of the cell surface of mouse dendritic cells and other leukocytes. *J. Exp. Med.* 154, 168–187 (1981).

81. Ignatowicz, L., Kappler, J. & Marrack, P. The repertoire of T cells shaped by a single MHC/peptide ligand. *Cell* 84, 521–529 (1996).

82. Larhammar, D., Gustafsson, K., Claesson, L., et al. Alpha chain of HLA-DR transplantation antigens is a member of the same protein superfamily as the immunoglobulins. *Cell* 30, 153–161 (1982).

83. Schamboeck, A., Korman, A. J., Kamb, A. & Strominger, J. L. Organization of the transcriptional unit of a human class II histocompatibility antigen: HLA-DR heavy chain. *Nucl. Acids Res.* 11, 8663–8675 (1983).

84. Pierre, P., Turley, S. J., Gatti, E., et al. Developmental regulation of MHC class II transport in mouse dendritic cells. *Nature* 388, 787–792 (1997).

85. Cella, M., Engering, A., Pinet, V., Pieters, J. & Lanzavecchia, A. Inflammatory stimuli induce accumulation of MHC class II complexes on dendritic cells. *Nature* 388, 782–787 (1997).

86. Inaba, K., Inaba, M., Romani, N., et al. Generation of large numbers of dendritic cells from mouse bone marrow cultures supplemented with granulocyte/macrophage colony-stimulating factor. *J. Exp. Med.* 176, 1693–1702 (1992).

87. Inaba, K., Pack, M., Inaba, M., Sakuta, H., Isdell, F. & Steinman, R. M. High levels of a major histocompatibility complex II—self peptide complex on dendritic cells from lymph node. *J. Exp. Med.* 186, 665–672 (1997).

88. Wong, B. R., Josien, R., Lee, S. Y., et al. TRANCE (tumor necrosis-factor [TNF]-related activation-induced cytokine), a new TNF family member predominantly expressed in T cells, is a dendritic cell specific survival factor. *J. Exp. Med.* 186, 2075–2080 (1997).

89. Steinman, R. M. The dendritic cell system and its role in immunogenicity. *Annu. Rev. Immunol.* 9, 271–296 (1991).

90. Steinman, R. M., Pack, M. & Inaba, K. Dendritic cells in the T cell areas of lymphoid organs. *Immunol. Rev.* 156, 25–37 (1997).

91. Banchereau, J. & Steinman, R. M. Dendritic cells and the control of immunity. *Nature* In Press, (1998).

92. Vremec, D., Zorbas, M., Scollay, R., et al. The surface phenotype of dendritic cells purified from mouse thymus and spleen: investigation of the CD8 expression by a subpopulation of dendritic cells. *J. Exp. Med.* 176, 47–58 (1992).

93. Matzinger, P. & Guerder, S. Does T-cell tolerance require a dedicated antigen-presenting cell? *Nature* 338, 74–76 (1989).

94. Zal, T., Volkmann, A. & Stockinger, B. Mechanisms of tolerance induction in major histocompatibility complex class II-restricted T cells specific for a blood-borne self-antigen. *J. Exp. Med.* 180, 2089–2099 (1994).

95. Fesq, H., Bacher, M., Nain, M. & Gemsa, D. Programmed cell death (apoptosis) in human monocytes infected by influenza virus. *Immunobiol.* 190, 175–182 (1994).

96. Fadok, V. A., J. S. Savill, C. Haslett, D. L. Bratton, D. E. Doherty, P. A. Campbell, and P. M. Henson. 1992. Different populations of macrophages use either the vitronectin receptor or the phosphatidylserine receptor to recognize and remove apoptotic cells. *J. Immunol.* 149:4029–4035.

97. Wyllie, A. H. 1980. Glucocorticoid-induced thymocyte apoptosis is associated with endogenous endonuclease activation. *Nature* 284:555–556.

98. Godman, G. C., A. F. Miranda, A. D. Deitch, and S. W. Tanenbaum. 1975. Action of cytochalasin D on cells of established lines. Zeiosis and movement at the cell surface. *J Cell Biochem* 64:644–647.

99. Casciola-Rosen, L., G. Anhalt, and A. Rosen. 1994. Autoantigens targeted in systemic lupus erythematosus are clustered in two populations of surface structures on apoptotic keratinocytes. *J. Exp. Med.* 179:1317–1330.

100. Savill, J. 1998. Phagocytic docking without shocking. *Nature* 392:442–443.

101. Savill, J. 1997. Recognition and phagocytosis of cells undergoing apoptosis. *Br. Med. Bull.* 53:491–508.

102. Albert, M. L., B. Sauter, N. and Bhardwaj. 1998. Dendritic cells acquire antigen from apoptotic cells and induce class I-restricted CTLs. *Nature* 392:86–89.

103. Bevan, M. J. 1976. Cross-priming for a secondary cytotoxic response to minor H antigens with H-2 congenic cells which do not cross-react in the cytotoxic assay. *J. Exp. Med.* 143:1283–1288.

104. Huang, A. Y. C., P. Golumbek, M. Ahmadzadeh, E. Jaffee, D. Pardoll, and H. Levitsky. 1994. Role of bone marrow-derived cells in presenting MHC class I-restricted tumor antigens. *Science* 264:961–965.

105. Kurts, C., W. R. Heath, F. R. Carbone, J. Allison, J. F. A. P. Miller, and H. Kosaka. 1996. Constitutive class I-restricted exogenous presentation of self antigens in vivo. *J. Exp. Med.* 184:923–930.

106. Banchereau, J., and R. M. Steinman. 1998. Dendritic cells and the control of immunity. *Nature* 392:245–252.

107. Sallusto, F., and A. Lanzavecchia. 1995. Dendritic cells use macropinocytosis and the mannose receptor to concentrate antigen in the MHC class II compartment. Downregulation by cytokines and bacterial products. *J. Exp. Med.* 182:389–400.

108. Sallusto, F., and A. Lanzavecchia. 1994. Efficient presentation of soluble antigen by cultured human dendritic cells is maintained by granulocyte/macrophage colony-stimulating factor plus interleukin 4 and downregulated by tumor necrosis factor α. *J. Exp. Med.* 179:1109–1118.

109. Pierre, P., S. J. Turley, E. Gatti, M. Hull, J. Meltzer, A. Mirza, K. Inaba, R. M. Steinman, and I. Mellman. 1997. Developmental regulation of MHC class II transport in mouse dendritic cells. *Nature* 388:787–792.

110. Inaba, K., M. Inaba, M. Naito, and R. M. Steinman. 1993. Dendritic cell progenitors phagocytose particulates, including Bacillus Calmette-Guerin organisms, and sensitize mice to mycobacterial antigens in vivo. *J. Exp. Med.* 178: 479–488.

111. Reis e Sousa, C., P. D. Stahl, and J. M. Austyn. 1993. Phagocytosis of antigens by Langerhans cells in vitro. *J. Exp. Med.* 178:509–519.

112. Inaba, K., M. Witmer-Pack, M. Inaba, K. S. Hathcock, H. Sakuta, M. Azuma, H. Yagita, K. Okumura, P. S. Linsley, S. Ikehara, S. Muramatsu, R. J. Hodes, and R. M. Steinman. 1994. The tissue distribution of the B7-2 costimulator in mice: abundant expression on dendritic cells in situ and during maturation in vitro. *J. Exp. Med*. 180:1849–1860.

113. Bender, A., M. Sapp, G. Schuler, R. M. Steinman, and N. Bhardwaj. 1996. Improved methods for the generation of dendritic cells from nonproliferating progenitors in human blood. *J. Immunol. Methods* 196:121–135.

114. Romani, N., D. Reider, M. Heuer, S. Ebner, B. Eibl, D. Niederwieser, and G. Schuler. 1996. Generation of mature dendritic cells from human blood: An improved method with special regard to clinical applicability. *J. Immunol. Meth*. 196:137–151.

115. Sallusto, F., C. Nicolo, R. De Maria, S. Corinti, and R. Testi. 1996. Ceramide inhibits antigen uptake and presentation by dendritic cells. *J. Exp. Med*. 184:2411–2416.

116. Caux, C., C. Massacrier, B. Vanbervliet, B. Dubois, C. Van Kooten, I. Durand, and J. Banchereau. 1994. Activation of human dendritic cells through CD40 cross-linking. *J. Exp. Med*. 180:1263–1272.

117. Rieser, C., G. Bock, H. Klocker, G. Bartsch, and M. Thurnher. 1997. Prostaglandin E2 and tumor necrosis factor α cooperate to activate human dendritic cells: Synergistic activation of interleukin 12 production. *J. Exp. Med*. 186:1603–1608.

118. Hess, K. L., G. F. Babcock, D. S. Askew, and J. M. Cook-Mills. 1998. A novel flow cytometric method for quantifying phagocytosis of apoptotic cells. *Cytometry* 27:145–152.

119. Bhardwaj, N., A. Bender, N. Gonzalez, L. K. Bui, M. C. Garrett, and R. M. Steinman. 1994. Influenza virus-infected dendritic cells stimulate strong proliferative and cytolytic responses from human CD8+ T cells. *J. Clin. Invest*. 94:797–807.

120. Fesq, H., M. Bacher, M. Nain, and D. Gemsa. 1994. Programmed cell death (apoptosis) in human monocytes infected by influenza virus. *Immunobiol*. 190:175–182.

121. Hofmann, P., H. Sprenger, A. Kaufmann, A. Bender, C. Hasse, M. Nain, and D. Gemsa. 1997. Susceptibility of mononuclear phagocytes to influenza A virus infection and possible role in the antiviral response. *J. Leuk. Biol*. 612:408–414.

122. Steinkamp, J. A., J. S. Wilson, G. C. Saunders, C. C. and Stewart. 1981. Phagocytosis: Flow Cytometric Quantitation with Fluorescent Microspheres. *Science* 215:64–66.

123. Gotch, F., J. Rothbard, K. Howland, A. Townsend, and A. McMichael. 1987. Cytotoxic T lymphocytes recognize a fragment of influenza virus matrix protein in association with HLA-A2. *Nature* 326:881

124. Silverstein, R. L., M. Baird, S. Lo, and L. M. Yesner. 1992. Sense and antisense cDNA transfection of CD36 in melanoma cells. Role of CD36 as a thrombospondin receptor. *J. Biological Chemistry* 267:16607–16612.

125. Zhou, L.-J., and T. F. Tedder. 1995. Human blood dendritic cells selectively express CD83, a member of the immunoglobulin superfamily. *J. Immunol*. 154:3821–3835.

126. De Togni, P., J. Goellner, N. H. Ruddle, P. R. Streeter, A. Fick, S. Mariathasan, S. C. Smith, R. Carlson, L. P. Shornick, J. Strauss-Schoenberger, J. H. Russell, R. Karr, and D. D. Chaplin. 1994. Abnormal development of peripheral lymphoid organs in mice deficient in lymphotoxin. *Science* 264:703–707.

127. Savill, J. S., I. Dransfield, N. Hogg, C. and Haslett. 1990. Vitronectin receptor-mediated phagocytosis of cells undergoing apoptosis. *Nature* 343:170–173.

128. Ren, Y., R. L. Silverstein, J. Allen, and J. Savill. 1995. CD36 gene transfer confers capacity for phagocytosis of cells undergoing apoptosis. *J. Exp. Med*. 181:1857. (Abstract)

129. Devitt, A., O. D. Moffatt, C. Raykundalia, J. D. Capra, D. L. Simmons, and C. D. Gregory. 1998. Human CD14 mediates recognition and phagocytosis of apoptopic cells. *Nature* 392:505–509.

130. Diaz-Gonzalez, F., J. Forsyth, B. Steiner, and M. H. Ginsberg. 1996. Trans-dominant inhibition of integrin function. *Molecular Biology of the Cell* 7:1939–1951.

131. Blystone, S. D., I. L. Graham, F. P. Lindberg, and E. J. Brown. 1994. Integrin alpha v beta 3 differentially regulates adhesive and phagocytic function of the fibronectin receptor alpha 5 beta 1. *Journal of Cell Biology* 127:1129–1137.

132. Inaba, K., S. Turley, F. Yamaide, T. Iyoda, K. Mahnke, M. Inaba, M. Pack, M. Subklewe, B. Sauter, D. Sheff, M. L. Albert, N. Bhardwaj, I. Mellman, and R. M. Steinman. 1998. Efficient presentation of phagocytosed cellular fragments on the MHC class II products of dendritic cells. *Submitted*.

133. Carbone, F. R., M. W. Moore, J. M. Sheil, and M. J. Bevan. 1988. Induction of cytotoxic T lymphocytes by primary in vitro stimulation with peptides. *J. Exp. Med*. 167:1767–1779.

134. Heath, W. R., C. Kurts, J. F. A. P. Miller, and F. Carbone. 1998. Cross-tolerance: a pathway for inducing tolerance to peripheral tissue antigens. *J. Exp. Med*. 187:1549–1553.

135. Inaba, K., M. Inaba, N. Romani, H. Aya, M. eguchi, S. Ikehara, S. Muramatsu, and R. M. Steinman. 1992. Generation of large numbers of dendritic cells from mouse bone marrow cultures supplemented with granulocyte/macrophage colony-stimulating factor. *J. Exp. Med*. 176:1693–1702.

136. Voll, R. E., M. Herrmann, E. A. Roth, C. Stach, and J. R. Kalden. 1997. Immunosuppressive effects of apoptotic cells. *Nature* 390:350–351.

137. Fadok, V. A., D. L. Bratton, A. Konowal, P. W. Freed, J. Y. Westcott, and P. M. Henson. 1998. Macrophages that have ingested apoptosis cells in vitro inhibit proinflammatory cytokine production through autocrine/paracrine mechanisms involving TGF-β, PGE2, and PAF. *J. Clin. Invest*. 101:890–898.

138. Sugita, M., and M. B. Brenner. 1995. Association of the invariant chain with major histocompatibility complex class I molecules directs trafficking to endocytic compartments. *Journal of Biological Chemistry* 270:1443–1448.

139. Jondal, M., R. Schirmbeck, and J. Reimann. 1996. MHC class-I restricted CTL responses to exogenous antigens. *Immunity* 5:295–302.

140. Snyder, H. L., I. Bacik, J. R. Bennink, G. Kearns, T. W. Behrens, T. Bachi, M. Orlowski, and J. W. Yewdell. 1997. Two novel routes of transporter associated with antigen processing [TAP]-independent major histocompatibility complex class I antigen processing. *J. Exp. Med.* 186: 1087–1098.

141. Rubartelli, A., A. Poggi, and M. R. Zocchi. 1997. The selective engulfment of apoptotic bodies by dendritic cells is mediated by the αvβ3 integrin and requires intracellular and extracellular calcium. *Eur. J. Immunol.* 27:1893–1900.

142. Savill, J., N. Hogg, Y. Ren, and C. Hasslet. 1992. Thrombospondin cooperates with CD36 and the vitronectin receptor in macrophage recognition of neutrophils undergoing apoptosis. *Journal of Clinical Investigation* 90:1513–1522.

143. Ryeom, S. W., J. R. Sparrow, and R. L. Silverstein. 1996. CD36 participates in the phagocytosis of rod outer segments by retinal pigment epithelium. *Journal of Cell Science* 109:387–395.

144. Finnemann, S. C., V. L. Bonilha, A. D. Marmorstein, and E. Rodriguez-Boulan. 1997. Phagocytosis of rod outer segments by retinal pigment epithelial cells requires alpha (v) beta5 integrin for binding but not for internalization. *PNAS* 94:12932–12937.

145. Friedlander, M., P. C. Brooks, R. W. Shaffer, C. M. Kincaid, J. A. Varner, and D. A. Cheresh. 1995. Definition of Two Antgiogenic Pathways by Distinct $\alpha_v$ Integrins. *Science* 270:1500–1502.

146. McClean, J. W., D. J. Vestal, D. A. Cheresh, and S. C. Bodary. 1990. cDNA Sequence of the Human Integrin $\beta_5$ Subunit. *Journal of Biological Chemistry* 265: 17126–17131.

147. Albert, M. L. et al. Immature dendritic cells phogocytose apoptotic cells via $\alpha_v\beta_5$ and CD36, and cross present antigens to cytotoxic T lymphocytes. *J. Exp. Med.* 188: 1359–1368 (1998).

148. Albert, M. L. & Bhardwaj, N. Resurrecting the Dead: DCs cross-present antigen derived from apoptotic cells on MHCI. *The Immunologist* 6:194–199 (1998).

149. Platt, N., da Silva, R. P. & Gordon, S. Recognizing death: the phagocytosis of apoptotic cells. *Trends Cell Biol.* 8:365–372 (1998).

150. Saville, J. Recognition and phagacytosis of cells undergoing apoptosis. *Br. Med. Bull.* 53, 491–508.

151. Larocca, D. et. al. a Mr. 46,000 human milk fat globule protein that is highly expressed in human breast tumors contains factor VIII-like domains. *Concl. Res* 51:4994–4998 (1991).

152. Taylor, M. R. et al. Lacloodherin (formerly BA46), a membrane-associated glycoprotein expressed in human milk and breast carcinomas, promotes Arg-Gly-Asp (RGP)-dependent cell adhesion. *DNA Cell Biol.* 16:861–869 (1997).

153. Peterson, J. A. et al. Glycoproteins of the human milk fat globule in the protection of the breast-fed infant against infections. *Biol Neonate* 74:143–162 (1998).

154. Mather, I. H. et al. Membranes of mammary gland. XII. Loosely associated proteins and compositional heterogeneity of bovine milk fat globule membrane. *J. Diary Sic.* 60:394–402 (1977).

155. Patton, S. & Keenan, T. W. The milk fat globule membrane. *Biochim Biophys Acta* 415:273–309 (1975).

156. H V Arregaard, J. et. al. Characterization of glycoprotein PAS-6/7 from membranes of bovine milk fat globules *Eir. J. Biochem.* 240:628–636 (1996).

157. J. Savill, *Br. Med. Bull.* 53, 491 (1997).

158. J. J. Cohen, *Immunol. Today* 14, 126 (1993).

159. E. Duvall, A. H. Wyllie, *Immunol. Today* 7, 115 (1986).

160. J. Banchereau, R. M. Steinman, *Nature* 392, 245 (1998).

161. M. L. Albert, B. Sauter, N. Bhardwaj, *Nature* 392, 86 (1998).

162. K. Inaba, et al, *J. Exp. Med.* In Press, (1998).

163. S. E. Macatonia, S. C. Knight, A. J. Edwards, S. Griffiths, P. Fryer, *J. Exp. Med.* 166, 1654 (1987).

164. G. G. MacPherson, C. D. Jenkins, M. J. Stein, C. Edwards, *J. Immunol.* 154, 1317 (1995). 165. T. De Smedt, et al, *J. Exp. Med.* 184, 1413 (1996).

166. J. A. Roake, et al, *J. Exp. Med.* 181, 2237 (1995).

167. M. Rescigno, et al, *PNAS* 95, 5229 (1998).

168. N. Bhardwaj, et al, *J. Clin. Invest.* 94, 797 (1994).

169. A. Bender, et al, *Immunobiology* 198, 64 (1997).

170. C. Caux, et al, *J. Exp. Med.* 180, 1263 (1994).

171. M. Cella, et al, *J. Exp. Med.* 184, 747 (1996).

172. A. Bender, M. Sapp, G. Schuler, R. M. Steinman, N. Bhardwaj, *J. Immunol. Methods* 196, 121 (1996).

173. M. Cella, F. Sallusto, A. Lanzavecchia, Curr. Opin. *Immunol.* 9, 10 (1997).

174. N. Romani, et al, *J. Immunol. Meth.* 196, 137 (1996).

175. B. de Saint-Vis, et al, *Immun.* 9, 325 (1998).

176. M. L. Albert, et al, *J. Exp. Med.* 188, 1359 (1998).

177. K. L. Hess, G. F. Babcock, D. S. Askew, Cook-Mills J. M. *Cytometry* 27, 145 (1998).

178. J. A. Steinkamp, J. S. Wilson, G. C. Saunders, C. C. Stewart, *Science* 215, 64 (1981).

179. P. Rovere, et al, *J. Immunol.* 161, 4467 (1998).

180. P. S. Freudenthal, R. M. Steinman, *Proc. Natl. Acad. Sci. USA* 87, 7698 (1990).

181. N. Bhardwaj, S. M. Friedman, B. C. Cole, A. J. Nisanian, *J. Exp. Med.* 175, 267 (1992).

182. R. E. Voll, M. Herrmann, E. A. Roth, C. Stach, J. R. Kalden, *Nature* 390, 350 (1997).

183. V. A. Fadok, et al, *J. Clin. Invest.* 101, 890 (1998).

184. Y. Gao, J. M. Herndon, H. Zhang, T. S. Griffith, T. A. Ferguson, *J. Exp. Med.* 188, 887 (1998).

185. W. R. Heath, C. Kurts, J. F. A. P. Miller, F. Carbone, *J. Exp. Med.* 187, 1549 (1998).

186. C. Kurts, H. Kosaka, F. R. Carbone, J. F. A. P. Miller, W. R. Heath, *J. Exp. Med.* 186, 239 (1997).

187. C. Kurts, W. R. Heath, H. Kosaka, J. F. A. P. Miller, F. R. Carbone, *J. Exp. Med.* 188, 415 (1998).

188. J. P. Ridge, F. Di Rosa, P. Matzinger, *Nature* 393, 474 (1998).

189. S. P. Schoenberger, R. E. M. Toes, E. I. H. van der Voort, R. Offringa, C. J. M. Melief, *Nature* 393, 480 (1998).

190. S. R. M. Bennett, et al, *Nature* 393, 478 (1998).

191. C. A. Janeway, *Immunol. Today* 13, 11 (1992).

192. Andersen, M. H. et al. Bovine PAS-6/7 binds $\alpha_v\beta_5$ integrins and anionic phospholipids through two domains. *Biochemistry* 36:5441–5446 (1997).

193. Amigorena, S. Anti-tumor immunotherapy using dendritic-cell-derived exosumes [In Process Citation]. *Res Immunol.* 149:661–662 (1998).

194. Raposo, G. et al. B Lymphocytes secrete antigen-presenting vesicles. *J. Exp. Med* 183:1161–1172 (1996).

195. Hughes, P. E. & Pfaff, M. Integrin affinity modulation. *Trends Cell Biol.* 8:359–364 (1998).

We claim:

1. A method of assessing cytotoxic T lymphocyte activity comprising:
   a) providing an antigen presenting dendritic cell prepared by contacting the dendritic cell with an apoptotic cell expressing an antigen or an apoptotic cell fragment, bleb, or body containing an antigen, wherein the apoptotic cell is shown to be apoptotic by a procedure selected from the group consisting of Annexin V staining, propidium iodide staining, DNA laddering, and staining with dUTP and terminal transferase (TUNEL staining), wherein said contacting is for a time sufficient to allow said antigen to be internalized by the dendritic cell, and wherein said apoptotic cell expressing or containing said antigen has been induced in vitro to become apoptotic prior to exposure to the dendritic cell;
   b) exposing the antigen presenting dendritic cell of step a) to a population of T lymphocytes to be assayed for their ability to exhibit killer cell activity; and
   c) assaying the cytotoxic activity of the T lymphocytes exposed to said antigen presenting dendritic cell.

2. The method according to claim 1, wherein the antigen presented by the dendritic cell is a tumor antigen and the T lymphocytes are assayed for their cytotoxic activity against tumor cells.

3. The method according to claim 1, wherein the antigen presented by the dendritic cell is a viral antigen and the T lymphocytes are assayed for their cytotoxic activity against viral infected cells.

4. The method of claim 1, wherein the apoptosis is induced by irradiation with ultraviolet light, gamma irradiation, steroids, serum deprivation, cytokines, or drugs which induce apoptosis.

5. The method of claim 1, wherein said antigen is produced recombinantly.

6. The method of claim 5, wherein said apoptotic cells comprise said recombinantly produced antigen prior to becoming apoptotic.

* * * * *

SEQUENCE LISTING

<160> NUMBER OF SEQ ID NOS: 6

<210> SEQ ID NO 1
<211> LENGTH: 9
<212> TYPE: PRT
<213> ORGANISM: Influenza virus

<400> SEQUENCE: 1

Gly Ile Leu Gly Phe Val Phe Thr Leu
 1               5

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
tgagaagtgc ccctgccc                                                   18

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gttggctgtg tcccattttg ct                                              22

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttgtaggatt tgtgaacttg                                                 20

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
gggaattcat atgaaatcat aaaagcaaca aacat                                35

<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6
cggaattcta catttcactt cctcattttc tg                                   32